US008557767B2

(12) United States Patent
Anantharamaiah et al.

(10) Patent No.: US 8,557,767 B2
(45) Date of Patent: Oct. 15, 2013

(54) SYNTHETIC APOLIPOPROTEIN E MIMICKING POLYPEPTIDES AND METHODS OF USE

(75) Inventors: Gattadahalli M. Anantharamaiah, Birmingham, AL (US); David W. Garber, Birmingham, AL (US); Geeta Datta, Pelham, AL (US); Sheila P. Handattu, Vestavia Hills, AL (US); Vinod K. Mishra, Homewood, AL (US)

(73) Assignee: UAB Research Foundation, Birmingham, AL (US)

( * ) Notice: Subject to any disclaimer, the term of this patent is extended or adjusted under 35 U.S.C. 154(b) by 557 days.

(21) Appl. No.: 12/675,073

(22) PCT Filed: Aug. 27, 2008

(86) PCT No.: PCT/US2008/074485
§ 371 (c)(1),
(2), (4) Date: Mar. 22, 2010

(87) PCT Pub. No.: WO2009/032702
PCT Pub. Date: Mar. 12, 2009

(65) Prior Publication Data
US 2010/0286025 A1 Nov. 11, 2010

Related U.S. Application Data

(60) Provisional application No. 60/968,355, filed on Aug. 28, 2007.

(51) Int. Cl.
*A61K 38/00* (2006.01)
*A61P 3/06* (2006.01)

(52) U.S. Cl.
USPC .......................................................... 514/7.4

(58) Field of Classification Search
None
See application file for complete search history.

(56) References Cited

U.S. PATENT DOCUMENTS

| | | | |
|---|---|---|---|
| 3,687,808 A | 8/1972 | Englisch et al. |
| 3,767,040 A | 10/1973 | Tushaus |
| 4,155,913 A | 5/1979 | Hellerbach et al. |
| 4,342,566 A | 8/1982 | Theofilopoulos et al. |
| 4,428,938 A | 1/1984 | Kisfaludy et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,643,988 A | 2/1987 | Segrest et al. |
| 4,667,025 A | 5/1987 | Miyoshi et al. |
| 4,684,520 A | 8/1987 | Bertelli |
| 4,762,779 A | 8/1988 | Snitman |
| 4,789,737 A | 12/1988 | Miyoshi et al. |
| 4,816,567 A | 3/1989 | Cabilly et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,868,116 A | 9/1989 | Morgan et al. |
| 4,876,335 A | 10/1989 | Yamane et al. |
| 4,877,611 A | 10/1989 | Cantrell |
| 4,897,355 A | 1/1990 | Eppstein et al. |
| 4,904,582 A | 2/1990 | Tullis |
| 4,946,778 A | 8/1990 | Ladner et al. |
| 4,948,882 A | 8/1990 | Ruth |
| 4,958,013 A | 9/1990 | Letsinger |
| 4,980,286 A | 12/1990 | Morgan et al. |
| 4,981,957 A | 1/1991 | Lebleu et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,135,917 A | 8/1992 | Burch |
| 5,138,045 A | 8/1992 | Cook et al. |
| 5,166,315 A | 11/1992 | Summerton et al. |
| 5,168,053 A | 12/1992 | Altman et al. |
| 5,175,273 A | 12/1992 | Bischofberger et al. |
| 5,176,996 A | 1/1993 | Hogan et al. |
| 5,177,196 A | 1/1993 | Meyer, Jr. et al. |

(Continued)

FOREIGN PATENT DOCUMENTS

AU 2001286732 3/2002
AU 2005287004 3/2006

(Continued)

OTHER PUBLICATIONS

U.S. Appl. No. 13/429,022, filed Mar. 23, 2012, G. Anantharamaiah.
Klein R, et al. The association of atherosclerosis, vascular risk factors, and retinopathy in adults with diabetes: the atherosclerosis risk in communities study, Opthalmology 109, pp. 1225-1234 (2002).
Roscoe, et al. Lipid changes in the eye concomitant with the development of atherosclerosis in the aorta in the rabbit, Circ Res 23, pp. 633-643 (1968).
Preliminary Amendment filed Jul. 6, 2010 with the U.S. Appl. No. 12/675,089, filed Apr. 21, 2010 (1st Named Inventor—Anantharamaiah) (3 pages).
Requirement for Restriction/Election mailed Apr. 16, 2012 by the U.S. Appl. No. 12/675,089, filed Apr. 21, 2010 (1st Named Inventor—Anantharamaiah) (7 pages).

(Continued)

*Primary Examiner* — Thomas Heard
(74) *Attorney, Agent, or Firm* — Ballard Spahr, LLP

(57) ABSTRACT

The present invention provides novel synthetic apolipoprotein E (ApoE)-mimicking peptides wherein the receptor binding domain of apolipoprotein E is covalently linked to 18A, the well characterized lipid-associating model class A amphipathic helical peptide, or a modified version thereof. Such peptides enhance low density lipoprotein (LDL) and very low density lipoprotein (VLDL) binding to and degradation by fibroblast or HepG2 cells. Also provided are possible applications of the synthetic peptides in lowering human plasma LDL/VLDL cholesterol levels, thus inhibiting atherosclerosis. The present invention also relates to synthetic peptides that can improve HDL function and/or exert anti-inflammatory properties.

12 Claims, 24 Drawing Sheets

(56) References Cited

U.S. PATENT DOCUMENTS

| | | | |
|---|---|---|---|
| 5,185,444 | A | 2/1993 | Summerton et al. |
| 5,188,897 | A | 2/1993 | Suhadolnik et al. |
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,235,033 | A | 8/1993 | Summerton et al. |
| 5,245,022 | A | 9/1993 | Weis et al. |
| 5,254,469 | A | 10/1993 | Warren, III et al. |
| 5,258,506 | A | 11/1993 | Urdea et al. |
| 5,262,536 | A | 11/1993 | Hobbs, Jr. |
| 5,264,423 | A | 11/1993 | Cohen et al. |
| 5,264,562 | A | 11/1993 | Matteucci |
| 5,264,564 | A | 11/1993 | Matteucci |
| 5,272,250 | A | 12/1993 | Spielvogel et al. |
| 5,276,019 | A | 1/1994 | Cohen et al. |
| 5,278,302 | A | 1/1994 | Caruthers et al. |
| 5,286,717 | A | 2/1994 | Cohen et al. |
| 5,292,873 | A | 3/1994 | Rokita et al. |
| 5,294,533 | A | 3/1994 | Lupski et al. |
| 5,298,490 | A | 3/1994 | Heavner et al. |
| 5,317,098 | A | 5/1994 | Shizuya et al. |
| 5,319,080 | A | 6/1994 | Leumann et al. |
| 5,321,131 | A | 6/1994 | Agrawal et al. |
| 5,334,711 | A | 8/1994 | Sproat et al. |
| 5,344,822 | A | 9/1994 | Levine et al. |
| 5,358,934 | A | 10/1994 | Borovsky et al. |
| 5,359,044 | A | 10/1994 | Cook et al. |
| 5,367,066 | A | 11/1994 | Urdea et al. |
| 5,371,241 | A | 12/1994 | Brush |
| 5,391,377 | A | 2/1995 | Barnwell et al. |
| 5,391,723 | A | 2/1995 | Priest |
| 5,393,878 | A | 2/1995 | Leumann |
| 5,399,676 | A | 3/1995 | Froehler |
| 5,405,938 | A | 4/1995 | Summerton et al. |
| 5,405,939 | A | 4/1995 | Suhadolnik et al. |
| 5,414,077 | A | 5/1995 | Lin et al. |
| 5,416,203 | A | 5/1995 | Letsinger |
| 5,432,272 | A | 7/1995 | Benner |
| 5,434,257 | A | 7/1995 | Matteucci et al. |
| 5,436,330 | A | 7/1995 | Taira et al. |
| 5,446,137 | A | 8/1995 | Maag et al. |
| 5,451,463 | A | 9/1995 | Nelson et al. |
| 5,453,496 | A | 9/1995 | Caruthers et al. |
| 5,455,233 | A | 10/1995 | Spielvogel et al. |
| 5,457,135 | A | 10/1995 | Baranowitz .................. 514/725 |
| 5,457,187 | A | 10/1995 | Gmeiner et al. |
| 5,459,255 | A | 10/1995 | Cook et al. |
| 5,466,677 | A | 11/1995 | Baxter et al. |
| 5,466,786 | A | 11/1995 | Buhr et al. |
| 5,470,967 | A | 11/1995 | Huie et al. |
| 5,476,766 | A | 12/1995 | Gold et al. |
| 5,476,925 | A | 12/1995 | Letsinger et al. |
| 5,480,869 | A | 1/1996 | Wei et al. |
| 5,484,908 | A | 1/1996 | Froehler et al. |
| 5,486,603 | A | 1/1996 | Buhr |
| 5,489,677 | A | 2/1996 | Sanghvi et al. |
| 5,502,177 | A | 3/1996 | Matteucci et al. |
| 5,503,978 | A | 4/1996 | Schneider et al. |
| 5,508,060 | A | 4/1996 | Perman et al. |
| 5,510,475 | A | 4/1996 | Agrawal et al. |
| 5,512,439 | A | 4/1996 | Hornes et al. |
| 5,512,667 | A | 4/1996 | Reed et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,465 | A | 6/1996 | Haralambidis et al. |
| 5,525,711 | A | 6/1996 | Hawkins et al. |
| 5,536,821 | A | 7/1996 | Agrawal et al. |
| 5,539,082 | A | 7/1996 | Nielsen et al. |
| 5,541,306 | A | 7/1996 | Agrawal et al. |
| 5,541,307 | A | 7/1996 | Cook et al. |
| 5,541,313 | A | 7/1996 | Ruth |
| 5,543,293 | A | 8/1996 | Gold et al. |
| 5,545,730 | A | 8/1996 | Urdea et al. |
| 5,550,111 | A | 8/1996 | Suhadolnik et al. |
| 5,552,538 | A | 9/1996 | Urdea et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,332 | A | 10/1996 | Hoogenboom et al. |
| 5,565,552 | A | 10/1996 | Magda et al. |
| 5,567,810 | A | 10/1996 | Weis et al. |
| 5,567,811 | A | 10/1996 | Misiura et al. |
| 5,571,799 | A | 11/1996 | Tkachuk et al. |
| 5,574,142 | A | 11/1996 | Meyer, Jr. et al. |
| 5,576,427 | A | 11/1996 | Cook et al. |
| 5,578,717 | A | 11/1996 | Urdea et al. |
| 5,578,718 | A | 11/1996 | Cook et al. |
| 5,579,250 | A | 11/1996 | Balaji et al. |
| 5,580,731 | A | 12/1996 | Chang et al. |
| 5,580,737 | A | 12/1996 | Polisky et al. |
| 5,580,967 | A | 12/1996 | Joyce |
| 5,585,481 | A | 12/1996 | Arnold, Jr. et al. |
| 5,587,361 | A | 12/1996 | Cook et al. |
| 5,587,371 | A | 12/1996 | Sessler et al. |
| 5,587,469 | A | 12/1996 | Cook et al. |
| 5,591,584 | A | 1/1997 | Chang et al. |
| 5,591,722 | A | 1/1997 | Montgomery et al. |
| 5,594,121 | A | 1/1997 | Froehler et al. |
| 5,595,726 | A | 1/1997 | Magda et al. |
| 5,595,873 | A | 1/1997 | Joyce |
| 5,595,973 | A | 1/1997 | Bogden |
| 5,596,086 | A | 1/1997 | Matteucci et al. |
| 5,596,091 | A | 1/1997 | Switzer |
| 5,597,696 | A | 1/1997 | Linn et al. |
| 5,597,909 | A | 1/1997 | Urdea et al. |
| 5,599,923 | A | 2/1997 | Sessler et al. |
| 5,599,928 | A | 2/1997 | Hemmi et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,612,895 | A | 3/1997 | Balaji et al. |
| 5,614,617 | A | 3/1997 | Cook et al. |
| 5,616,466 | A | 4/1997 | Cantor et al. |
| 5,618,704 | A | 4/1997 | Sanghvi et al. |
| 5,623,070 | A | 4/1997 | Cook et al. |
| 5,624,824 | A | 4/1997 | Yuan et al. |
| 5,625,050 | A | 4/1997 | Beaton et al. |
| 5,627,053 | A | 5/1997 | Usman et al. |
| 5,627,158 | A | 5/1997 | Cho-Chung |
| 5,631,115 | A | 5/1997 | Ohtsuka et al. |
| 5,631,146 | A | 5/1997 | Szostak et al. |
| 5,631,280 | A | 5/1997 | Ciccarone et al. |
| 5,633,133 | A | 5/1997 | Long et al. |
| 5,633,360 | A | 5/1997 | Bischofberger et al. |
| 5,639,873 | A | 6/1997 | Barascut et al. |
| 5,641,754 | A | 6/1997 | Iversen |
| 5,645,985 | A | 7/1997 | Froehler et al. |
| 5,646,020 | A | 7/1997 | Swiggen et al. |
| 5,646,031 | A | 7/1997 | DeYoung et al. |
| 5,646,042 | A | 7/1997 | Stinchcomb et al. |
| 5,646,265 | A | 7/1997 | McGee |
| 5,650,316 | A | 7/1997 | Aggarwal et al. |
| 5,652,094 | A | 7/1997 | Usman et al. |
| 5,652,107 | A | 7/1997 | Lizardi et al. |
| 5,658,873 | A | 8/1997 | Bertsch-Frank et al. |
| 5,663,312 | A | 9/1997 | Chaturvedula |
| 5,670,633 | A | 9/1997 | Cook et al. |
| 5,677,437 | A | 10/1997 | Teng et al. |
| 5,677,439 | A | 10/1997 | Weis et al. |
| 5,681,941 | A | 10/1997 | Cook et al. |
| 5,683,873 | A | 11/1997 | George et al. |
| 5,683,874 | A | 11/1997 | Kool |
| 5,683,902 | A | 11/1997 | Hampel et al. |
| 5,688,670 | A | 11/1997 | Szostak et al. |
| 5,688,941 | A | 11/1997 | Cook et al. |
| 5,691,317 | A | 11/1997 | Cho-Chung |
| 5,693,535 | A | 12/1997 | Draper et al. |
| 5,693,773 | A | 12/1997 | Kandimalla et al. |
| 5,700,920 | A | 12/1997 | Altmann et al. |
| 5,700,922 | A | 12/1997 | Cook |
| 5,712,384 | A | 1/1998 | Symonds et al. |

(56) References Cited

U.S. PATENT DOCUMENTS

| | | | |
|---|---|---|---|
| 5,714,331 A | 2/1998 | Buchardt et al. |
| 5,719,262 A | 2/1998 | Buchardt et al. |
| 5,721,138 A | 2/1998 | Lawn |
| 5,721,367 A | 2/1998 | Kay et al. |
| 5,728,521 A | 3/1998 | Yuan et al. |
| 5,731,295 A | 3/1998 | Draper et al. |
| 5,731,424 A | 3/1998 | Toothman et al. |
| 5,733,549 A | 3/1998 | Yamada et al. |
| 5,733,879 A | 3/1998 | Rosseneu et al. |
| 5,770,576 A | 6/1998 | Morozov ......................... 514/19 |
| 5,770,715 A | 6/1998 | Sugiyama et al. |
| 5,780,228 A | 7/1998 | Parma et al. |
| 5,780,607 A | 7/1998 | Goodnow, Jr. et al. |
| 5,786,138 A | 7/1998 | Swenson |
| 5,786,462 A | 7/1998 | Schneider et al. |
| 5,792,613 A | 8/1998 | Schmidt et al. |
| 5,795,721 A | 8/1998 | Rabin et al. |
| 5,800,758 A | 9/1998 | Topolkaraev et al. |
| 5,804,440 A | 9/1998 | Burton et al. |
| 5,807,718 A | 9/1998 | Joyce et al. |
| 5,811,300 A | 9/1998 | Sullivan et al. |
| 5,814,467 A | 9/1998 | Curtiss et al. |
| 5,834,185 A | 11/1998 | Ts'o et al. |
| 5,837,243 A | 11/1998 | Deo et al. |
| 5,837,855 A | 11/1998 | Chowrira et al. |
| 5,843,708 A | 12/1998 | Hardman et al. |
| 5,846,713 A | 12/1998 | Pagratis et al. |
| 5,849,903 A | 12/1998 | Pietrzkowski et al. |
| 5,854,238 A | 12/1998 | Kempen |
| 5,856,103 A | 1/1999 | Gray et al. |
| 5,856,188 A | 1/1999 | Hampel et al. |
| 5,856,463 A | 1/1999 | Prydz et al. |
| 5,858,660 A | 1/1999 | Eaton et al. |
| 5,861,254 A | 1/1999 | Schneider et al. |
| 5,861,288 A | 1/1999 | Usman et al. |
| 5,864,026 A | 1/1999 | Jensen et al. |
| 5,866,701 A | 2/1999 | Hampel et al. |
| 5,869,246 A | 2/1999 | Matsuo et al. |
| 5,869,248 A | 2/1999 | Yuan et al. |
| 5,869,253 A | 2/1999 | Draper |
| 5,869,339 A | 2/1999 | Hampel et al. |
| 5,869,641 A | 2/1999 | Jayasena et al. |
| 5,874,566 A | 2/1999 | Veerapanane et al. |
| 5,877,021 A | 3/1999 | Stinchcomb et al. |
| 5,877,022 A | 3/1999 | Stinchcomb et al. |
| 5,877,153 A | 3/1999 | Harris et al. |
| 5,877,162 A | 3/1999 | Werner et al. |
| 5,891,683 A | 4/1999 | Usman et al. |
| 5,891,684 A | 4/1999 | Usman et al. |
| 5,910,408 A | 6/1999 | Szostak et al. |
| 5,919,772 A | 7/1999 | Szyf et al. |
| 5,939,598 A | 8/1999 | Kucherlapati et al. |
| 5,955,590 A | 9/1999 | Levina et al. |
| 5,958,691 A | 9/1999 | Pieken et al. |
| 5,962,426 A | 10/1999 | Glazer |
| 5,972,699 A | 10/1999 | Draper |
| 5,972,704 A | 10/1999 | Draper et al. |
| 5,985,621 A | 11/1999 | Usman et al. |
| 5,989,906 A | 11/1999 | Thompson |
| 5,989,908 A | 11/1999 | Scanlon |
| 5,990,081 A | 11/1999 | Ageland et al. |
| 5,990,088 A | 11/1999 | Ensoli et al. |
| 5,994,320 A | 11/1999 | Low et al. |
| 5,998,193 A | 12/1999 | Keese et al. |
| 5,998,203 A | 12/1999 | Matulic-Adamic et al. |
| 5,998,602 A | 12/1999 | Torrence et al. |
| 6,001,988 A | 12/1999 | Parma et al. |
| 6,004,925 A | 12/1999 | Dasseux et al. |
| 6,005,013 A | 12/1999 | Suh et al. |
| 6,005,095 A | 12/1999 | Capaccioli et al. |
| 6,007,995 A | 12/1999 | Baker et al. |
| 6,011,002 A | 1/2000 | Pastan et al. |
| 6,011,020 A | 1/2000 | Gold et al. |
| 6,013,443 A | 1/2000 | Heilig et al. |
| 6,013,522 A | 1/2000 | Monia et al. |
| 6,017,756 A | 1/2000 | Draper |
| 6,017,898 A | 1/2000 | Pietrzkowski et al. |
| 6,018,042 A | 1/2000 | Mett et al. |
| 6,019,739 A | 2/2000 | Rhee et al. |
| 6,020,130 A | 2/2000 | Gold et al. |
| 6,022,962 A | 2/2000 | Chowrira et al. |
| 6,025,198 A | 2/2000 | Bennett et al. |
| 6,028,186 A | 2/2000 | Tasset et al. |
| 6,030,776 A | 2/2000 | Eaton et al. |
| 6,033,910 A | 3/2000 | Monia et al. |
| 6,037,323 A | 3/2000 | Dasseux et al. |
| 6,040,147 A | 3/2000 | Ridker et al. |
| 6,040,296 A | 3/2000 | Nyce |
| 6,046,004 A | 4/2000 | Wu et al. |
| 6,046,166 A | 4/2000 | Dasseux et al. |
| 6,046,319 A | 4/2000 | Power et al. |
| 6,051,698 A | 4/2000 | Janjic et al. |
| 6,057,437 A | 5/2000 | Kamiya et al. |
| 6,086,918 A | 7/2000 | Stern et al. |
| 6,090,921 A | 7/2000 | Winge et al. |
| 6,107,457 A | 8/2000 | Arlinghaus et al. |
| 6,113,898 A | 9/2000 | Anderson et al. |
| 6,130,364 A | 10/2000 | Jakobovits et al. |
| 6,180,377 B1 | 1/2001 | Morgan et al. |
| 6,191,151 B1 | 2/2001 | Zik |
| 6,201,165 B1 | 3/2001 | Grant et al. |
| 6,228,989 B1 | 5/2001 | Traugh et al. |
| 6,265,377 B1 | 7/2001 | Dasseux et al. |
| 6,287,590 B1 | 9/2001 | Dasseux et al. |
| 6,303,619 B1 | 10/2001 | Linden |
| 6,329,341 B1 | 12/2001 | Dasseux et al. |
| 6,367,479 B1 | 4/2002 | Williams et al. |
| 6,376,464 B1 | 4/2002 | Dasseux et al. |
| 6,383,808 B1 | 5/2002 | Monia et al. |
| 6,410,802 B1 | 6/2002 | Dasseux et al. |
| 6,423,511 B1 | 7/2002 | Nakamura et al. |
| 6,423,830 B1 | 7/2002 | Winge et al. |
| 6,444,111 B1 | 9/2002 | Montgomery |
| 6,444,681 B1 | 9/2002 | Flavahan et al. |
| 6,455,088 B1 | 9/2002 | Dasseux et al. |
| 6,458,592 B1 | 10/2002 | Jakobovits et al. |
| 6,459,003 B1 | 10/2002 | Dasseux et al. |
| 6,464,975 B2 | 10/2002 | Millis |
| 6,472,184 B1 | 10/2002 | Hegemann |
| 6,498,038 B1 | 12/2002 | Ghosh et al. |
| 6,506,799 B1 | 1/2003 | Dasseux et al. |
| 6,506,879 B1 | 1/2003 | Ageland et al. |
| 6,506,880 B2 | 1/2003 | Anantharamaiah |
| 6,514,523 B1 | 2/2003 | Sparks |
| 6,518,412 B1 | 2/2003 | Dasseux et al. |
| 6,555,651 B2 | 4/2003 | Stern et al. |
| 6,559,284 B1 | 5/2003 | Ageland et al. |
| 6,573,239 B1 | 6/2003 | Dasseux et al. |
| 6,602,854 B1 | 8/2003 | Dasseux et al. |
| 6,617,134 B1 | 9/2003 | Sirtori et al. |
| 6,630,450 B1 | 10/2003 | Dasseux et al. |
| 6,635,623 B1 | 10/2003 | Hoogeveen et al. |
| 6,646,170 B2 | 11/2003 | Dasseux et al. |
| 6,664,230 B1 | 12/2003 | Fogelman et al. |
| 6,673,780 B2 | 1/2004 | Dasseux et al. |
| 6,680,203 B2 | 1/2004 | Dasseux et al. |
| 6,696,545 B1 | 2/2004 | Buelow et al. |
| 6,699,910 B2 | 3/2004 | Dasseux et al. |
| 6,703,422 B2 | 3/2004 | Dasseux et al. |
| 6,713,507 B2 | 3/2004 | Dasseux et al. |
| 6,716,816 B1 | 4/2004 | Dasseux et al. |
| 6,717,031 B2 | 4/2004 | Games et al. |
| 6,727,063 B1 | 4/2004 | Lander et al. |
| 6,734,169 B2 | 5/2004 | Dasseux et al. |
| 6,753,313 B1 | 6/2004 | Dasseux et al. |
| 6,773,719 B2 | 8/2004 | Rodrigueza et al. |
| 6,790,953 B2 | 9/2004 | Dasseux et al. |
| 6,831,105 B2 | 12/2004 | Dasseux et al. |
| 6,849,636 B2 | 2/2005 | Waddell et al. |
| 6,849,714 B1 | 2/2005 | Bridon et al. |
| 6,869,568 B2 | 3/2005 | Fogelman et al. |
| 6,887,470 B1 | 5/2005 | Bridon et al. |
| 6,909,014 B2 | 6/2005 | Dasseux et al. |
| 6,930,085 B2 | 8/2005 | Fogelman et al. |

(56) References Cited

U.S. PATENT DOCUMENTS

| | | | |
|---|---|---|---|
| 6,933,279 | B2 | 8/2005 | Fogelman et al. |
| 6,936,691 | B2 | 8/2005 | Fiscella et al. |
| 6,982,348 | B2 | 1/2006 | Kori et al. |
| 7,144,862 | B2 | 12/2006 | Fogelman et al. |
| 7,148,197 | B2 | 12/2006 | Fogelman et al. |
| 7,148,199 | B2 | 12/2006 | Neu ............................... 514/19 |
| 7,166,578 | B2 | 1/2007 | Fogelman et al. |
| 7,189,689 | B2 | 3/2007 | Dasseux et al. |
| 7,192,940 | B2 | 3/2007 | Dasseux et al. |
| 7,199,102 | B2 | 4/2007 | Fogelman et al. |
| 7,211,565 | B2 | 5/2007 | Dasseux et al. |
| 7,217,785 | B2 | 5/2007 | Bielicki |
| 7,291,590 | B2 | 11/2007 | Kisilevsky et al. |
| 7,312,190 | B2 | 12/2007 | Dasseux et al. |
| 7,427,662 | B2 | 9/2008 | Hornick et al. |
| 7,470,660 | B2 | 12/2008 | Schwartz et al. |
| 7,531,514 | B2 | 5/2009 | Fogelman et al. |
| 7,563,771 | B2 | 7/2009 | Anantharamiah et al. |
| 7,579,319 | B2 | 8/2009 | Fogelman et al. |
| 7,638,494 | B2 | 12/2009 | Fogelman et al. |
| 7,723,303 | B2 | 5/2010 | Fogelman et al. |
| 8,084,423 | B2 | 12/2011 | Anantharamiah et al. |
| 2001/0005714 | A1 | 6/2001 | Boffelli et al. |
| 2002/0042441 | A1 | 4/2002 | Acton et al. |
| 2002/0071862 | A1 | 6/2002 | Williams et al. |
| 2002/0142369 | A1 | 10/2002 | Fersht |
| 2003/0027769 | A1 | 2/2003 | Scialdone et al. |
| 2003/0040505 | A1 | 2/2003 | Fogelman et al. |
| 2003/0045460 | A1 | 3/2003 | Fogelman et al. |
| 2003/0077641 | A1 | 4/2003 | Laskowitz et al. |
| 2003/0087819 | A1 | 5/2003 | Bielicki |
| 2003/0109442 | A1 | 6/2003 | Bisgaier et al. |
| 2003/0125260 | A1 | 7/2003 | Haviv et al. |
| 2003/0203842 | A1 | 10/2003 | Dasseux et al. |
| 2003/0229015 | A1 | 12/2003 | Fogelman et al. |
| 2004/0059110 | A1 | 3/2004 | Nakano et al. |
| 2004/0122091 | A1 | 6/2004 | Dasseux et al. |
| 2004/0136989 | A1 | 7/2004 | Banerjee et al. |
| 2004/0152623 | A1 | 8/2004 | Varadhachary et al. |
| 2004/0186057 | A1 | 9/2004 | Anantharamiah et al. |
| 2004/0224011 | A1 | 11/2004 | Rodrigueza et al. |
| 2004/0266663 | A1 | 12/2004 | Schwartz et al. |
| 2004/0266671 | A1 | 12/2004 | Fogelman et al. |
| 2005/0070996 | A1 | 3/2005 | Dinh et al. |
| 2005/0154046 | A1 | 7/2005 | Wang et al. |
| 2005/0164950 | A1 | 7/2005 | Fogelman et al. |
| 2005/0197381 | A1 | 9/2005 | Wang et al. |
| 2005/0239136 | A1 | 10/2005 | Hazen et al. |
| 2006/0069030 | A1 | 3/2006 | Bachovechin |
| 2006/0172919 | A1 | 8/2006 | Hornick et al. |
| 2006/0173067 | A1 | 8/2006 | Fogelman et al. |
| 2006/0205634 | A1 | 9/2006 | Varadhachary et al. |
| 2006/0205669 | A1 | 9/2006 | Fogelman et al. |
| 2006/0217298 | A1 | 9/2006 | Srivastava |
| 2006/0217307 | A1 | 9/2006 | Takashi et al. |
| 2006/0234908 | A1 | 10/2006 | Fogelman et al. |
| 2007/0032430 | A1 | 2/2007 | Fogelman et al. |
| 2007/0060527 | A1 | 3/2007 | Fogelman et al. |
| 2007/0071756 | A1 | 3/2007 | Peyman |
| 2007/0101448 | A1 | 5/2007 | Anantharamiah et al. |
| 2007/0254839 | A1 | 11/2007 | Fogelman et al. |
| 2008/0045459 | A1 | 2/2008 | Fogelman et al. |
| 2008/0095821 | A1 | 4/2008 | Fogelman et al. |
| 2008/0096814 | A1 | 4/2008 | Fogelman et al. |
| 2008/0096815 | A1 | 4/2008 | Fogelman et al. |
| 2008/0096816 | A1 | 4/2008 | Fogelman et al. |
| 2008/0293639 | A1 | 11/2008 | Fogelman et al. |
| 2009/0163408 | A1 | 6/2009 | Fogelman et al. |
| 2009/0286741 | A1 | 11/2009 | Fogelman |

FOREIGN PATENT DOCUMENTS

| | | |
|---|---|---|
| CA | 2420222 | 2/2002 |
| CA | 2580501 | 3/2006 |
| CN | 1739787 A | 3/2006 |
| CN | 1469754 | 4/2007 |
| CN | 1943781 | 4/2007 |
| EP | 1186299 | 3/2002 |
| EP | 1318828 | 6/2003 |
| EP | 1562624 | 8/2005 |
| EP | 1799242 | 6/2007 |
| JP | 2000-136202 | 6/1905 |
| JP | 61-126099 | 6/1986 |
| JP | 7-507554 | 8/1995 |
| JP | 2006-312650 | 11/2006 |
| WO | WO 93/25581 | 12/1993 |
| WO | WO 97/36927 | 10/1997 |
| WO | WO 98/09602 | 3/1998 |
| WO | WO 99/16408 | 4/1999 |
| WO | WO 99/16409 | 4/1999 |
| WO | WO 99/47566 | 9/1999 |
| WO | WO 01/75168 | 10/2001 |
| WO | WO 01/75170 | 10/2001 |
| WO | WO 02/15923 | 2/2002 |
| WO | WO 02/098446 | 12/2002 |
| WO | WO 03/086326 | 10/2003 |
| WO | WO 03/089612 | 10/2003 |
| WO | WO 2004/027027 | 4/2004 |
| WO | WO 2004/034977 | 4/2004 |
| WO | WO 2004/043396 | 5/2004 |
| WO | WO 01/75067 | 10/2004 |
| WO | WO 2005/016280 | 2/2005 |
| WO | WO 2006/020652 | 2/2006 |
| WO | WO 2006/063132 | 6/2006 |
| WO | WO 2006/118805 | 11/2006 |
| WO | WO 2008/021088 | 2/2008 |
| WO | WO 2008/143679 | * 11/2008 |
| WO | WO 2009/073725 | 6/2009 |

OTHER PUBLICATIONS

Requirement for Restriction/Election filed May 16, 2012 with the U.S. Appl. No. 12/675,089, filed Apr. 21, 2010 (1st Named Inventor—Anantharamaiah) (9 pages).
Non-final Rejection mailed Jun. 29, 2012 by the U.S. Appl. No. 12/675,089, filed Apr. 21, 2010 (1st Named Inventor—Anantharamaiah) (12 pages).
Non-final Rejection mailed Jan. 13, 2012 by the U.S. Appl. No. 12/027,728, filed Feb. 7, 2008 (1st Named Inventor—Anantharamaiah) (14 pages).
Response to Non-final Rejection filed Apr. 10, 2012 with the U.S. Appl. No. 12/027,728, filed Feb. 7, 2008 (1st Named Inventor—Anantharamaiah) (15 pages).
Non-Final Rejection mailed Jun. 14, 2012 by the U.S. Appl. No. 12/027,728, filed Feb. 7, 2008 (Inventor—Anantharamaiah) (10 pages).
U.S. Appl. No. 10/269,755, filed Oct. 11, 2002, Fogelman et al.
U.S. Appl. No. 11/541,481, filed Sep. 29, 2006, Fogelman et al.
U.S. Appl. No. 11/541,482, filed Sep. 29, 2006, Fogelman et al.
U.S. Appl. No. 11/541,494, filed Sep. 29, 2006, Fogelman et al.
Abrahmsen et al. (1991) Biochemistry 30: 4151 (1991).
Acsadi G et al. (1991) Human dystrophin expression in mdx mice after intramuscular injection of DNA constructs. Nature, 352(6338): 815-8.
Adachi, T., et al., (2003) Biochemical J. 289(2):523-527.
Aikawa, M., et al., Lipid Lowering Reduces Oxidative Stress and Endothelial Cell Activation in Rabbit Atheroma. Circulation (2002) 106:1390-1396.
Ajees et al. (2006) Crystal structure of human apolipoprotein A-1: Insights into its protective effect against cariodvascular diseases. PNAS 103:2126-2131.
Ali, et al. (2005). Apolipoprotein E suppresses the Type I inflammatory response in vivo. Circ. Res. 97:922-927.
Ambati, J. et al. (2003) Age-related macular degeneration: etiology, pathogenesis, and therapeutic strategies. SurV Ophthalmol. 48(3): 257-293.
Anantharamaiah et al. (1985) Studies of Synthetic Peptide of the Amphipathic Helix. The Journal of Biological Chemistry 260:10248-10255.
Anantharamaiah et al. (1988) Effect of Oxidation on the Properties of Apolipoproteins A-I and A-II. J. Lipid Res. 29:309-318.

(56) References Cited

OTHER PUBLICATIONS

Anantharamaiah et al. (1990) Use of Synthetic Peptide Analogues to Localize Lecithin: Cholseterol Acyltransferase Activating Domain in Apolipoprotein A-I. Arteriosclerosis 10: 95-105.
Anantharamaiah G et al., (2006) Synthetic peptides: managing lipid disorders. Curr Opin Lipidol. 17(3): 233-237.
Anantharamaiah et al. (2007) Structural requirements for antioxidative and a enti-inflammatory properties of apolipoprotein A-I mimetic peptides. J Lipid Res. 48(9): 1915-1923.
Anantharamaiah, G.M. et al., (2001) Toward the design of peptide mimics of antiatherogenic apolipoproteins A-I and E., Current Science 81:53-65.
Aoyagi H et al. (1988) Synthesis of antibacterial peptides-gramicidin S analogs and designed amphiphilic oligopeptides. Tetrahedron; 44:877-886.
Aravinda, S. et al., (2003) Aromatic-Aromatic Interactions in Crystal Structures of Helical Peptide Scaffolds Containing Projecting Phenylalinine Residues, J. Am Chem Soc.; 125:5308 5315.
Arisaph Pharmaceuticals Reports on Promising Results Presented At American Heart Association: Novel Apo A-I Mimetic Peptide Significantly Inhibits Atherosclerosis in Preclinical Animal Study, http://www.biospace.com/news_print.aspx?NewsEntityID=2610, 2012.
Armitage et al., (1997) Peptide nucleic acid—DNA duplexes: Long range hole migration from an internally linked anthraquinone. Proc Natl Acad Sci USA.; 94(23):12320-5.
Ashby D, (2001) Lack of effect of serum amyloid A (SAA) on the ability of high-density lipoproteins to inhibit endothelial cell adhesion molecule expression. Atherosclerosis. 154:113-121.
Ashby et al., (1998) Factors influencing the ability of HDL to inhibit expression of vascular cell adhesion molecule-1 in endothelial cells. Arteriosclerosis. Thrombosis and Vascular Biology, 18:1450-1455.
Badimon et al., (1990) Regression of Atherosclerotic Lesions by High Density Lipoprotein lasma Fraction in the Cholesterol-fed Rabbit. J. Clinical Investigation 85:1234-1241.
Baggiolini et al. Interleukin-8, a chemotactic and inflammatory cytokine. FEBS Lett. 307: 97-101, (1992).
Bailey et al. (2001) Clusterin, a binding protein with a molten globule-like region. Biochemistry. 40(39): 11828-11840.
Baker et al. (1999) Ability of reconstituted high density lipoproteins to inhibit cytokine-induced expression of vascular cell adhesion molecule-I in human umbilical cell endothelial cells. J Lipid Res, 1999, 40:345-353.
Baker et al. (2000) Phospholipid composition of reconstituted high density lipoproteins influences their ability to inhibit endothelial cell adhesion molecule expression. J Lipid Res, 2000;41:1261-1267.
Barengolts et al. (1998) Osteoporosis and coronary atherosclerosis in asymptomatic postmenopausal women. Calcif Tissue Int. 62(3): 209-213.
Barter, P.J. and Rye, K-A. High density lipoproteins and coronary heart disease. Atherosclerosis, 1996, 121:1-12.
Baumbach et al. (2002) Structure of Cerebral Arterioles in Cystathionine B-SynthaseDeficient Mice, Circulation Res., 91: 931-937.
Baumbach et al. (2003) Cerebral Arteruikar Structure in Mice Overexpressing Human Renin and Angiotensinogen, Hypertension, 41: 50-55.
Beatty S, Koh H, Phil M, Henson D, Boulton M. (2000) The role of oxidative stress in the pathogenesis of age-related macular degeneration. Surv Ophthalmol. 45(2): 115-134.
Bechinger B. (2000) Understanding peptide interactions with the lipid bilayer: a guide to membrane protein engineering. Curr Opin Chem Biol. 4(6):639-644.
Beisiegel, U. et al. The LDL-receptor-related protein, LRP, is an apolipoprotein E-binding protein. Nature 341: 162-164 (1989).
Berkner et al. (1987) Abundant Expression of Polyomavirus Middle T Antigen and Dihydrofolate Reductase in an Adenovirus Recombinant. J. Virology 61:1213-1220.
Besiegel, U. et al. (1991) Lipoprotein lipase enhances the binding of chylomicrons to low density lipoprotein receptor-related protein Proc. Natl. Acad. Sci. U.S.A. 88:8342-8346.
Betteridge, D.J., Long-term risk reduction: Who needs treatment?, Diabetes Research and Clinical Practice. (2005) 68S2:S15-2.
Bisoendial et al. (2003) Restoration of Endothelial Function by Increasing High-Density Lipoprotein in Subjects With Isolated Low High-Density Lipoprotein Circulation 107: 2944-2948.
Blackburn WD Jr, et al. (1991) Apolipoprotein A-I decreases neutrophil degranulation and superoxide production. J Lipid Res. 32(12): 1911-1918.
Blankenberg et al. (2001) Circulating cell adhesion molecules and death in patients with coronary artery disease. Circulation 2001;104:1336-1342.
Boerner et al. (1991) Production of Antigen-Specific Human Monoclonal Antibodies from In Vitro-Primed Human Splenocytes. J. Immunol., 147(1):86-95.
Boffa et al., Isolation of active genes containing CAG repeats by DNA strand invasion by a peptide nucleic acid. Proc Natl Acad Sci USA. Mar. 14, 1995; 92(6):1901-5.
Boffelli et al. (1997) Reconstitution and Further Characterization of the Cholesterol Transport Activity of the Small-Intestinal Brush Border Membrane Biochemistry 36:10784-10792.
Boffelli et al., (1997) The uptake of cholesterol at the small-intestinal brush border membrane is inhibited by apolipoproteins. FEBS Letters, 411: 7-11.
Borhani et al. (1999) Crystal structure of truncated human apolipoprotein A-1 suggests a lipid bound conformation. Proc. Natl. Acad. Sci. USA. 94:12291-12296.
Bourdillon et al. (2000) ICAM 1 deficiency reduces atherosclerotic lesions in double-knockout mice (ApoE(−/ ) IICAM-1(−/−)) fed a fat or a chow diet. Arterioscler Thromb Vasc Biol 2000;20:2630-2635.
Bowry et al. (1992) High density lipoprotein is the major carrier of lipid hydroperoxides in human blood plasma from fasting donors. Proc Natl Acad Sci USA. 1992;89:10316-10320.
Braddock. D. T., et al., (1996) Conformationally Specific Enhancement of Receptor-ediated LDL Binding and Internalization by Peptide Models of a Conserved Anionic N-Termina Domain of Human Apolipoprotein E. Biochemistry 35. 13975-13984.
Bradley, W.A., et al., (1986) ApoE is necessary and sufficient for the binding of large triglyceride-rich lipoproteins to the LDL receptor; apoB is unnecessary. J. Lipid Res. 27, 40-48.
Bradley et al. (1982) Apolipoprotein E degradation in human very low density lipoproteins by protease(s): chemical and biological consequences. Biochim. Biophys. Res. Commun. 109:1360-1367.
Brigham et al. (1989) Expression of a prokaryotic gene in cultured lung endothelial cells after lipofection with a plasmid vector. Am. J. Resp. Cell. Mol. Biol. I: 95-100.
Brousseau, M.E. (2005) Emerging role of high-density lipoprotein in the prevention of cardiovascular disease. Drug Discovery Today. 10:1095-1099.
Brousseau, M.E., and Hoeg, J.M. (1999) Transgenic rabbits as models for atherosclerosis research. J. lipid Res. 40:365-375.
Brown, D.T. and Burlingham, B.T., (1973) Penetration of Host Cell Membranes by Adenovirus 2 J. Virology 12:386-396.
Brown, B.G. et al. (2001) Simvastatin and Niacin, Antioxidant Vitamins, or the Combination for the Prevention of Coronary Disease. N Engl J Med. 345(22):1583-92.
Brown M.L., et al. (2000) A Macrophage Receptor for Apolipoprotein B48: Clining, Expression, and Atherosclerosis. Proc. Natl. Acad. Sci. USA 97:7488-7493.
Burger et al. (2002) High-density lipoprotein-associated apolipoprotein A-I: the missing link between infection and chronic inflammation? Autoimmunity Reviews 2002;1:111-117.
Burnett, J.R. and Vasikaran, S.D. (2002) Cardiovascular disease and osteoporosis: is there a link between lipids and bone? Ann Clin Biochem. 39(Pt 3): 203-210.
Calabresi L, et al. (2002) Elevated cellular adhesion molecules in subjects with low ML—cholesterol. Arterioscler Thromb Vasc Biol.;22:656-661.
Calabresi L, Franceschini G, Sirtoh CR, De Palma A, Saresella M, Ferrante P, Taramelli D. Inhibition of VCAM-1 expression in endothelial cells by reconstituted high density lipoproteins. Biochem Biophys Res Commun. (1997) 238:61-65.
Calabresi, L., et al., (2003) Entothelial Protection by High-Denisty Lipoproteins. Athero. Thromb. Vasc. Biol. 23:1724-1731.

(56) References Cited

OTHER PUBLICATIONS

Campbell, E.J. Human leukocyte elastase, cathepesin G and lactoferrin: family of neutrophil granule glycoproteins that bind to an alveolar macrophage receptor. Proc Natl Acad Sci USA (1982) 79:6941-6945.
Cardillo, C. et al., (1997) Xanthine Oxidase Inhibition With Oxypurinol Improves Endothelial Vasodilator Function in Hypercholesterolemic but Not in Hypertensive Patients. Hypertension 30:57-63.
Carlos TM, et al. (1990) Vascular cell adhesion molecule-1 mediates lymphocyte adherence to cytokine-activated cultured human endothelial cells. Blood;76:965-970.
Carr, A.C. et al. (2000) Oxidation of LDL by myeloperoxidase and reactive nitrogen species oxidation of LdL by myeloperoxidase and reactive nitrogen species. Arterioscler Thromb Vasc Biol; 20:1716-1723.
Carrara et al., Two helices plus a linker: A small model substrate for eukaryotic RNase P. Proc. Natl. Acad. Sci. (USA) 92:2627-2631 (1995).
Casserly, I. and Topol, E. (2004) Convergence of atherosclerosis and Alzheimer's disease: inflammation, cholesterol, and misfolded proteins Lancet 363:1139-1146.
Castelli, W.P. et al., Incidence of coronary heart disease and lipoprotein cholesterol levels. The Framingham study. JAMA. 1986; 256:2835-2838. Abstract.
Catapano, A.L. et al. Suppression of 3-hydroxy-3-methylglutaryl-CoA reductase by low density lipoproteins produced in vitro by lipoprotein lipase action on nonsuppressive very low density lipoproteins. J. Biol. Chem. 254: 1007-1009 (1979).
Charles-Schoeman C, Banquerigo ML, Hama S, Navab M, Park GS, Van Lenten BJ, Wagner AC, Fogelman AM, Brahn E. (2008) Treatment with an apolipoprotein A-1 mimetic peptide in combination with pravastatin inhibits collagen-induced arthritis. Clin Immunol. 127(2): 234-244.
Chiesa G, et al., Recombinant apolipoprotein A-I(Milano) infusion into rabbit carotid artery rapidly removes lipid from fatty streaks. Circ Res. 2002;90:974-980.
Chillon, J. and Baumbach, G.L. (1999) Effects of an Angiotensin-Converting Enzyme Inhibitor and a b-Blocker on Cerebral Arterioles in Rats Hypertension, 33: 856-861.
Chorev, M. and Goodman, M. (1995) Recent developments in retro peptides and proteins—an ongoing topochemical exploration. Trends Biotechnol. 13(10): 438-445.
Christison J, (1996) Rapid reduction and removal of HDL—but not LDL—associated cholesteryl ester hydroperoxides by rat liver in situ. Biochem J.; 314:739-742.
Chung, B.H. et al. Liposome-like Particles Isolated From Human Atherosclerotic Plaques Are Structurally and Compositionally Similar to Surface Remnants of Triglyceride-Rich Lipoproteins. Arterio. Thromb. 14:622-635 (1994).
Chung et al., (1985) Studies of Synthetic Peptide Analogs of the Amphipathic Helix. J. Biol. Chem. 60(18): 10256-10262.
Chung, B.H., et al. (1996) Probing structure and function of VLDL by synthetic amphipathic helical peptides. J. Lipid Res. 37:1099-1112.
Clark-Lewis et al. (1991) Chemical Synthesis, Purification, and Characterization of Two Inflammatory Proteins, Neutrophil Activating Peptide I (Interleukin-8) and Neutrophil Activating Peptide 2. Biochemistry 30: 3128-3135.
Clark-Lewis I, et al. (1994) Structural requirements for interleukin-8 function identified by design of analogs and CXC chemokine hybrids. J Biol Chem. 269(23): 16075-16081.
Clay, M.A. (2001) Time sequence of the inhibition of endothelial adhesion molecule expression by reconstituted high density liproteins, Atherosclerosis 157: 23-29.
Clay, M.A. et al. (1995) Localization of a domain in apolipoprotein E with both cytostatic and cytotoxic activity. Biochemistry. 34:11142-11151.
Clee, S.M., et al. (2000) Age and residual cholesterol efflux affect HDL cholesterol levels and coronary artery disease in ABCA1 hetrozygotes. J. Clin. Invest. 106:1263-1270.
Clubb, F.J., et al. (2001) Development of atherosclerotic plaque with endothelial disruption in Watanabe heritable hyperlipidemic rabbit aortas. Cardiovasc. Pathol. 9:1-11.
Cockerill, G.W. et al. (2001) Elevation of plasma high-density lipoprotein concentration reduces interleukin-I induced expression of E-selectin in an in vivo model of acute inflammation. Rculation;103:108-112.
Cockerill, G.W. et al. (1999) High-density lipoproteins differentially modulate cytokine induced expression of E-selectin and cyclooxygenase-2. Arterioscler Thromb Vasc Biol.;19:910-917.
Cockerill, G.W. et al. (1995) High-density lipoproteins inhibit crone-induced expression of endothelial cell adhesion molecules. Arterioscler Thromb Vasc Biol. 15:1987-1994.
Collard, M.W. and Griswold, M.D. (1987) Biosynthesis and molecular cloning of sulfated glycoprotein 2 secreted by rat Sertoli cells. Biochemistry. 26(12): 3297-3303.
Colles, S.M., Masson, J.M., Carlson, S.G., and Chisom, G.M., Oxidized LDL-induced injury and apoptosis in atherosclerosis. Potential roles for oxysterols. Trends Cardiovasc. Med. 11:131-138 (2001).
Berg, C. et al., (2004) The myeloperoxidase product hypochlorous acid oxidizes HDL in the human artery wall and impairs ABCA1-dependent cholesterol transport Natl.. Acad. Sci. U.S.A. 101:13032-13037.
Corey, D.R. Peptide nucleic acids: expanding the scope of nucleic acid recognition. Trends Biotechnol Jun. 1997; 15(6):224-9.
Coyne, E.F. et al. (2002) Methods for isolation and characterization of intracerebral arterioles in the C57/13L6 wild-type mouse, J. Neurosci. Meth., 120: 145-153.
Curcio, C.A. et al. (2001) Accumulation of cholesterol with age in human Bruch's membrane. Invest Ophthalmol Vis Sci. 42(1): 265-274.
Curcio CA, et al. (2005) Esterified and unesterified cholesterol in drusen and basal deposits of eyes with age-related maculopathy. Exp Eye Res. 81(6): 731-741.
Cybulsky MI, et al., (2001) A major role for VCAM-1, but not ICAM-I, in early atherosclerosis. Journal of Clinical Investigation;107:1255-1262.
Cyrus, et al., (2001) Absence of 12/15-lipoxygenase expression decreases lipid peroxidation and atherogenesis in apolipoprotein E-deficient mice. Circulation;103 :2277-2282.
Dai et al. (2004) Implantation of Immature Neonatal Cardiac Cells Into the Wall of the Aorta in Rats: A Novel Model for Studying Morphological and Functional Development of Heart Cells in an Extracardiac Environment. Circulation. 110(3): 324-329.
Dai et al. (2005) Allogeneic mesenchymal stem cell transplantation in postinfarcted rat myocardium: short- and long-term effects. Circulation 112(2): 214-223.
Dansky HM, et al., Adhesion of monocytes to arterial endothelium and initiation of atherosclerosis are critically dependent on vascular cell adhesion molecule-1 gene dosage. Arterioscler Thromb Vasc Biol 2001; 21:1662-1667.
Dansky HM, et al. (1999), Apo A-1 inhibits foam cell formation in Apo E-deficient mice after monocyte adherence to endothelium. J Clin Invest.;104:31-39.
Dashti et al. (2004) Model class A and class L peptides increase the production of apoA-I-containing lipoproteins in HepG2 cells. Journal of Lipid Res. 45: 1919-1928.
Datta et al. (2001) Effects of Increasing Hydrophobicity on the Physical-Chemical and Biological Properties of a Class A Amphipathic Helical Peptide. J Lipid Research 42:1096-1104.
Datta et al. The Receptor Binding Domain of Apolipoprotein E, Linked to a Model Class A Amphipathic Helix, Enhances Internalization and Degradation of LDL by Fibroblasts. Biochemistry 30: 213-220 (2000).
Datta et al., (2001) Cationic Domain (141-150) of Apo E Linked to a Class A Amphipathic Helix Enhances the Metabolism of Apo a-Containing Lipoproteins in Hepatocytes. Arterio. Thromb. Vasc. Biol. 21:651.
Datta et al. (2001) Cationic domain 141-150 of apoE covalently linked to a class A amphipathic helix enhances atherogenic lipoprotein metabolism in vitro and in vivo. Journal of Lipid Research 42:959-966.

(56) References Cited

OTHER PUBLICATIONS

Datta G, et al. (2009) Anti-inflammatory and recycling properties of an apolipoprotein mimetic peptide, Ac-hE18A-NH(2). Atherosclerosis Epub ahead of print. Volume and p. TBA.

Datta, G. et al. (2004) Aromatic Residue Position on the Nonpolar Face of Class A Amphipathic Helical Peptides Determines Biological Activity. J. Biol. Chem. 279:26509-26517.

Davenport, P. and Tipping, P.G. (2003) The role of interleukin-4 and interleukin-12 in the progression of atherosclerosis in apolipoprotein E-deficient mice. Am J Pathol 163:1117-1125.

Davidson, D. et al. Overproduction of Polyomavirus Middle T Antigen in Mammalian Cells through the Use of an Adenovirus Vector. J. Virology 61:1226-1239 (1987).

Davidson, et al. (1994) The Influence of Apolipoprotein Structure on the Efflux of Cellular Free Cholesterol to High Density Lipoprotein. J. Biol. Chem. 269(37): 22975-22982.

Dawson, P.E. et al. Synthesis of Proteins by Native Chemical Ligations. Science 266: 776-779 (1994).

De Caterina R, et al., (1998) Structural requirements for inhibition of cytokine-induced endothelial activation by unsaturated fatty acids. J. Lipid Res.;39:1062-1070.

Diederich et al. (2001) Apolipoprotein AI and HDL3 Inhibit Spreading of Primary Human Monocytes through a Mechanism that Involves Cholesterol Depletion and Regulation of CD42, Atherosclerosis. 159:313-324.

Dimayuga, P. et al., Reconstituted HDL containing human apolipoprotein A-1 reduces VCAM-1 expression and neointima formation following periadventitial cuffinduced carotid injury in apoE null mice. Biochem Biophys Res Commun. 1999;264:465-468.

Dithmar S, et al. (2000) Ultrastructural changes in Bruch's membrane of apolipoprotein E-deficient mice. Invest Ophthalmol Vis Sci. 41(8): 2035-2042.

Dooley, C.T. et al. (1994) An All D-Amino Acid Opioid Peptide with Central Analgesic Activity from a Combinatorial Library. Science. 2019-2022.

Dunlop, D.S. And Neidle, A. (1997) The Origin and Turnover of D-Serine in Brain. Biochemical and Biophysical Research Communication 235:26-30.

Duong, P. T., et al. (2006). Characterization of nascent HDL particles and macroparticles formed by ABC A1-mediated cholesterol efflux of cellular lipids to apo A-I. J. Lipid Res. 47:832-843.

Dyer, C. A., et al., (1991) Only multimers of a synthetic peptide of human apolipoprotein E are biologically active. J. Biol. Chem. 266, 15009-15015.

Dyer, C. A., et al., (1991) Only Multimers of a Synthetic Peptide of Human Apolipoprotein E Are Biologically Active J. Biol. Chem. 296, 22803-22806.

Dyer, C. A., et al., (1995) Structural features of synthetic peptides of apolipoprotein E that bind the LDL receptor. J. Lipid Res. 36, 80-8.

Ehara et al. (2001) Elevated Levels of Oxidized Low Density Lipoprotein Show a Positive Relationship With the Severity of Acute Coronary Syndromes. Circulation. 103:1955-1960.

Eisenberg et al. Lipoprotein lipase enhances binding of lipoproteins to heparan sulfate on cell surfaces and extracellular matrix. J. Clin Invest. 90: 2013-2021 (1992).

Epand et al. (1987) Studies Synthetic Peptide Analog of the Amphipathic Helix J. Biol. Chem. 262(19): 9389-9396.

Epand RM, Stafford A, Leon B, Lock PE, Tytler EM, Segrest JP, Anantharamaiah GM. (1994) HDL and apolipoprotein A-I protect erythrocytes against the generation of procoagulant activity. Arterioscler Thromb. 14(11): 1775-1783.

Epand, et al. (2004) an Apolipoprotein AI Mimetic Peptide: Membrane Interactions and the Role of Cholesterol. Biochemistry. 43:5073-5083.

Epand, et al. (2004) Two Homologous Apolipoprotein AI Mimetic Peptides: Relationship Between Membrane Interactions and Biological Activity. J. of Biol. Chem. 279:51404-51415.

Farkas, M.H. et al., (2004) The recycling of apolipoprotein E and its amino-terminal 22kDA fragment: evidence for multiple redundant pathways. J. Lipid Res. 45:1546-1554.

Felgner et al. Lipofection: a highly efficient, lipid-mediated DNA-transfection procedure. PNAS, 84: 7413-7417 (1987).

Field et al. (2001) Gene expression of sterol regulatory element-binding proteins in hamster small intestine, Journal of Lipid Research. 42:1-9.

Keech, A. et al. Effects of long-term fenofibrate therapy on cardiovascular events in 9795 people with type 2 diabetes (the FIELD study): randomised controlled trial. Lancet. (2005) 366: 1849-1861.

Fielding and Fielding (1995) Molecular physiology of reverse cholesterol transport. J. Lipid Res. 36: 211-228.

Fleisher et al., Stimulation of arterial endothelial cell prostacyclin synthesis by high density lipoproteins. J Biol. Chem. 1982; 257:6653-6655.

Fogelman et al., Malondialdehyde alteration of low density lipoproteins leads to cholesteryl ester accumulation in human monocyte-macrophages. Proc Natl Acad Sci USA. 1980; 77:2214-2218.

Fogelman, A.M., When good cholesterol goes bad. Nat Med. 2004; 10:902-903.

Folch, J. et al., (1957) A simple method for isolation and purification of total lipides from animal tissues. J. Biol. Chem. 226:497-509.

Footer et al. (1996) Biochemical evidence that a D-Loop is part of a four-strandedPNA-DNA bundle. Nickel-mediated cleavage of duplex DNA by a Gly-Gly-His-Bis-PNA, Biochemistry. 35(33): 10673-9.

Forte et al., Altered activities of anti-atherogenic enzymes LCAT, paraoxonase, and platelet-activating factor acetylhydrolase in atherosclerosis susceptible mice. J. Lipid Res., 2002; 43:477-485.

Fritz, I.B. (1992) What is clusterin? Clin Exp Immunol. 88(3): 375.

Fukuda, et al., Bilayer forming ion-pair amphi-philes from single chain surfactants. J Am Chem Soc., 1990, 112:1635-1637.

Futterman, L.G and Lemberg, L. (2004) Statin pleiotropy: fact or fiction? Am J Crit Care. 13(3): 244-249.

Gabay C. and Kushner I., Acute-phase proteins and other systemic responses to inflammation, N. Engl. I Med. 1999; 340; 448-454.

Gambacorti-Passerini et al., In Vitro Transcription and Translation Inhibition by Anti-PromyelocyticLeukemia (PML)/Retinoic Acid Receptor $\alpha$ and Anti-PML Peptide Nucleic Acid. Blood. 1996; 88(4):1411-7.

Garber DW, Handattu S, Aslan I, Datta G, Chaddha M, Anantharamaiah GM. (2003) Effect of an arginine-rich amphipathic helical peptide on plasma cholesterol in dyslipidemic mice. Atherosclerosis 168(2):229-237.

Garber et al. (1992) Turnover of synthetic class A amphipathic peptide analogues of exchangeable apolipoproteins in rats. Correlation with physical properties. Arteriosclerosis and Thrombosis, 12(8): 886-894.

Garber et al. (2001) A new synthetic class A amphipathic peptide analogue protects from diet-induced atherosclerosis. Journal of Lipid Research 42:-545-552.

Garber et al. (2001) An Arginine-rich amphipathic helical peptide mediates rapid clearance of plasma cholesterol is dyslipidemic mice. Arterio. Thromb. Vasc. Biol. 21:650.

Garber et al. (2006) Atherosclerosis and vascular disease: effects of peptide mimetics of apolipoproteins. Curr. Pharm. Biotechnol. 7:235-240.

Garber, D.W., Kulkarni, K.R., and Anantharamaiah, G.M. A sensitive and convenient method for lipoprotein profile analysis of individual mouse plasma samples. J. Lipid Res. 41:1020-1026, (2000).

Garner et al. (1998) Oxidation of high density lipoproteins. I. Formation of methionine sulfoxide in apolipoproteins AI and AII is an early event that accompanies lipid peroxidation and can be enhanced by alpha-tocopherol. J Biol Chem. 1998; 273:6080-6087.

Garner et al. (1998) Oxidation of high density lipoproteins. II. Evidence for direct reduction of lipid hydroperoxides by methionine residues of apolipoproteins AI and AII. J Biol Chem. 1998; 273:6088-6095.

Gaut, et al. (2002) Myeloperoxidase produces nitrating oxidants in vivo. J Clin Invest 2002; 109: 1311-1319.

Geetanjali, B. et al. Changes in heat shock protein 70 localization and its content in rabbit aorta at various stages of experimental atherosclerosis Cardiovascular Pathology 11: 97-103 (2002).

(56) References Cited

OTHER PUBLICATIONS

Gehrs KM, Anderson DH, Johnson LV, Hageman GS. (2006) Age-related macular degeneration—emerging pathogenetic and therapeutic concepts. Ann Med. 38(7): 450-471.

George et al. (2001) 12/15-lipoxygenase gene disruption attenuates atherogenesis in LDL, receptor-deficient mice. Circulation, 2001: 104:1646-1650.

Geysen HM, Mason TJ, Rodda SJ. (1988) Cognitive features of continuous antigenic determinants. J Mol Recognit. 1(1): 32-41.

Ghandi et al. (2004) Apolipoprotein B-containing Lipoprotein Particle Assembly: Lipid Capacity of the Nascent Lipoprotein Particle. J. Biol. Chem. 279:39757-39766.

Ghersi-Egea et al. (1996) Fate of Cerebrospinal Bluid-Borne Amyloid B-Peptide: Rapid Clearance into Blood and Appreciable Accumulation by Cerebral Arteries, J. Neurochem., 67: 880-883.

Gianturco et al., Receptor-mediated uptake of hypertriglyceridemic very low density lipoproteins by normal human fibroblasts. Journal of Lipid Research. 23: 984-993 (1982).

Gianturco, S.H. et al. Apolipoprotein E mediates uptake of Sf 100-400 hypertriglyceridemic very low density lipoproteins by the low density lipoprotein receptor pathway in normal human fibroblasts. J. Biol. Chem. 258:4526-4533 (1983).

Gianturco, S.H. et al. Control of 3-hydroxy 3-methylglutaryl CoA reductase activity in cultured human fibroblasts by VLDL of subjects with hypertriglyceredemia. J. Clin Invest. 61:320-328 (1978).

Gillote et al. (1999) Apolipoprotein-mediated plasma membrane microsolubilization. Role of lipid affinity and membrane penetration in the efflux of cellular cholesterol and phospholipid. J Biol. Chem. 274(4):2021-8.

Glomset, J.A. (1968) The Plasma lecithin: cholesterol acytransferase reaction. J. Lipid Res. 9:155-167.

Gomez-Foix, A.M. et al. Adenovirus-mediated Transfer of the Muscle Glycogen Phosphorylase Gene into Hepatocytes Confers Altered Regulation of Glycogen Metabolism. J. Biol. Chem. 267:25129-25134 (1992).

Gong et al., (1994) Structural and functional properties of human and mouse apolipoprotein A-I. Biochim. Biophys. Acta. 1213:335-342; Abstract.

Graf R, Schachman HK. (1996) Random circular permutation of genes and expressed polypeptide chains: application of the method to the catalytic chains of aspartate transcarbamoylase. Proc Natl Acad Sci U S A. 93(21): 11591-11596.

Greenway, P.J. et al. Human cytomegalovirus DNA: BumHI, EcoRI and Pst I restriction endonuclease cleavage maps Gene 18: 355-360 (1982).

Greten FR, Eckmann L, Greten TF, Park JM, Li ZW, Egan LJ, Kagnoff MF, Karin M. IKKbeta links inflammation and tumorigenesis in a mouse model of colitis-associated cancer. Cell. Aug. 6, 2004;118(3):285-96.

Griendling, K.K. et al. (2000) NAD(P)H Oxidase : Role in Cardiovascular Biology and Disease Circulation Research. 86:494-501.

Grundy S.M., et al. Implications of Recent Clinical Trials for the National Cholesterol Education Program Adult Treatment Panel III Guidelines Circulation. 110:227-239 (2004).

Gupta et al. (2004) Calculation of Creatinine Clearance Based on Unadjusted Body Weight Leads to Errors in Renal and Heart Failure Patients Circulation 110:III-243.

Gupta H, et al. (2005) Inhibition of lipopolysaccharide-induced inflammatory responses by an apolipoprotein AI mimetic peptide. Circ Res. 97(3): 236-243.

Gupta H, et al. (2005) Apolipoprotein E mimetic Peptide dramatically lowers plasma cholesterol and restores endothelial function in watanabe heritable hyperlipidemic rabbits. Circulation. 111(23): 3112-3118.

Gurfinkel et al (2002) Influenza Vaccine Pilot Study in Acute Coronary Syndromes and Planned Percutaneous Coronary Interventions. The FLU Vaccination Acute Coronary Syndromes (FLUVACS) Study. Circulation 105 :2143-2147.

Guzman, R.J. et al. Efficient Gene Transfer Into Myocardium by Direct Injection of Adenovirus Vectors Circulation Research 73:1201-1207 (1993).

Haimovici R, Gantz DL, Rumelt S, Freddo TF, Small DM. (2001) The lipid composition of drusen, Bruch's membrane, and sclera by hot stage polarizing light microscopy. Invest Ophthalmol Vis Sci. 42(7): 1592-1599.

Haj-Ahmad et al. Development of a Helper-Independent Human Adenovirus Vector and Its Use in the Transfer of the Herpes Simplex Virus Thymidine Kinase Gene. J. Virology. 57:267-274 (1986).

Halcox, J.P. et al. (2002) Prognostic Value of Coronary Vascular Endothelial Dysfunction. Circulation. 106:653-658.

Hamase et al. (2001) Determination of Free D-Proline and D-Leucine in the Brains of Mutant Mice Lacking D-Amino Acid Oxidase Activity. Analytical Biochemistry. 298:253-258.

Handattu et al. (2006) Physical, Chemical, and Structural Studies of Apolipoprotein A-I Mimetics Correlate Well with the Efficacy for Inhibiting Atherosclerosis Atheroscler. Thromb. Vasc. Biol. 26(5):e64.

Handattu, S., P.,Garber, D.W., Beno, B., Bain, A.D., Mishra, V.K., Palgunachari, M.N., Datta, G., Anantharamaiah, G.M., and Epand, R.M. ApoA-I Mimetic Peptides with Differing Ability to Inhibit Atherosclerosis Also Exhibit Differences in Their Interactions with Membrane Bilayers. J. Biol. Chem. 282:1980-1988 (2007).

Handwerger, et al. (1999) Pre-β-HDL stimulates placental lactogen release from human trophoblast cells. Am. J. Physiol. 276:E384-E389.

Hanvey et al. Antisense and Antigene properties of Peptide Nucleic Acids. Science. 1992; 258(5087):1481-5.

Harats, et al., Overexpression of 15-lipoxygenase in vascular endothelium accelerates early atherosclerosis in LDL receptor-deficient mice. Arterioscler Thromb Vasc Biol. 2000; 20:2100-2105.

Hardy et al. (2001) An Automated High-Performance Liquid Chromatography Procedure for the Quantitation of L- and D-Amino Acids by Means of Stepwise Precolumn Derivatization Analytical Biochemistry 291:297-299.

Harkin et al. (1997) The Effects of hyper-and hypocarbia on intraparenchymal arterioles in rat brian slices, Neuroreport, 8: 1841-1844.

Hashimoto (2000) Improvement of intestinal absorption of peptides: absorption of BI-Phe monoglucosylated insulin to rat intestinal brush-border membrane vesicles. J. Pharmaceutics & Therapeutics 50(2): 197-204.

Hasty, A.H., Linton, M.R., Sanan, D., Swift, L.L., and Fazio, S. Determination of lower threshold of apolipoprotein E resulting in lipoprotein remnant clearance. J. Lipid Res. 40:1529-1538 (1999).

Hauser et al.. (1998) Identification of a Receptor Mediating Absorption of Dietary Cholesterol in the Intestine Biochemistry 178423-17850.

Havel, R. J. George Lyman Duff memorial lecture. Role of the liver in atherosclerosis. Arteriosclerosis 5: 569-580 (1985).

Hayry et al., Stabile D peptide analog of insulin-like growth factor-1 inhibits smooth muscle cell proliferation after carotid balooning injury in the rat. FASEB J. 9(13): 1336-1344, 1995.

Hein TW, Platts SH, Waitkus-Edwards KR, Kuo L, Mousa SA, Meininger GA. (2001) Integrin-binding peptides containing RGD produce coronary arteriolar dilation via cyclooxygenase activation. Am J Physiol Heart Circ Physiol. 281(6): H2378-H2384.

Henricksen et al., Enhanced macrophage degradation of low density lipoprotein previously incubated with cultured endolelial cells; recognition by receptor for acetylated low density lipoproteins. Proc Natl Acad Sci USA., 1981; 78:6499-6503.

Hermanowski-Vosatka A, Balkovec JM, Cheng K, Chen HY, Hernandez M, Koo GC, Le Grand CB, Li Z, Metzger JM, Mundt SS, Noonan H, Nunes CN, Olson SH, Pikounis B, Ren N, Robertson N, Schaeffer JM, Shah K, Springer MS, Strack AM, Strowski M, Wu K, Wu T, Xiao J, Zhang BB, Wright SD, Thieringer R.11beta-HSD1 inhibition ameliorates metabolic syndrome and prevents progression of atherosclerosis in mice., J Exp Med. Aug. 15, 2005;202(4):517-27.

Hessler et al. (1979) LDL-induced cytotoxicity and its inhibition by 1-DL in human vascular smooth muscle and endothelial cells in culture. Atherosclerosis, 32:213-229, Abstract.

(56) References Cited

OTHER PUBLICATIONS

Hoffman et al. (1997) Isoprostanes: Free Radical-Generated Prostaglandins with constrictor Effects on cerebral Arterioles, Stroke, 28: 844-849.

Holvoet, P. et al. (1997)β-VLDL Hypercholesterolemia Relative to LDL Hypercholesterolemia Is Associated With Higher Levels of Oxidized Lipoproteins and a More Rapid Progression of Coronary Atherosclerosis in Rabbits Arterioscl. Thromb. Vasc. Biol. 17:2376-2382.

Hoogenboom et al. By-passing immunisation: Human antibodies from synthetic repertoires of germline VH gene segments rearranged in vitro J. Mol. Biol., 227:381-388, 1992.

Houstis, N., Rosen, E.D., and Lander E.S. Reactive oxygen species have a causal role in multiple forms of insulin resistance. Nature 440:944-948 (2006).

Hristova et al. (1999) An Amphipathic α-Helix at a Membrane Interface: A Structural Study using a Novel X-ray Diffraction Method. J. Mol. Biol. 290:99-117.

Huber MA, Azoitei N, Baumann B, Grünert S, Sommer A, Pehamberger H, Kraut N, Beug H, Wirth T. (2004) NF-kappaB is essential for epithelial-mesenchymal transition and metastasis in a model of breast cancer progression. J Clin Invest. 114(4): 569-581.

Hussain et al. High affinity binding between lipoprotein lipase and lipoproteins involves multiple ionic and hydrophobic interactions, does not require enzyme activity, and is modulated by glycosaminoglycans. J. Biol. Chem. 275: 29324-29330 (2000).

Hwang SJ, Ballantyne CM, Sharrett AR, Smith LC, Davis CE, Gotto AM Jr, Boerwinkle E. Circulating adhesion molecules VCAM-I, ICAM-I, and E-selectin in carotid therosclerosis and incident coronary heart disease cases. The atherosclerosis risk in communities (AMC) study. Circulation 1997;96:4219-4225.

Hyka et al. (2001) Apolipoprotein A-I Inhibits the Production of Interleukin-10 and Tumor Necrosis Factor-a by Blocking Contact-Mediated Activation of Monocytes by T Lymphocytes Blood 97:2381-2389.

Hyrup, B. and Nielsen, P.E. Peptide Nucleic Acids (PNA): Synthesis, Properties and Potential Applications Bioorg Med Chem. Jan. 1996; 4(1):5-23.

Ishigami, M., Swertfeger, D.K., Hui, M.S., Granholm, N. A. and Hui, D.Y. Apolipoprotein E inhibition of vascular smooth muscle cell proliferation but not the inhibition of migration is mediated through activation of inducible nitric oxide synthase. Arterio. Thromb. Vasc. Biol. 20:1020-1026 (2000).

Jaeger et al. Improved predictions of secondary structures for RNA Proc. Natl. Acad. Sci. USA 86:7706-7710, 1989.

Jakobovits et al. Germ-line transmission and expression of a human-derived yeast artificial chromosome. Nature, 362:255-258 (1993).

Jakobovits et al. Analysis of homozygous mutant chimeric mice: Deletion of the immunoglobulin heavy-chain joining region blocks B-cell development and antibody production Proc. Natl. Acad. Sci. USA, 90:2551-255 (1993).

Jamaluddin, et al. (1987) Aggregatory reactions of blood platelets in ustirred dilute suspensions and their monitoring by spectrophotometry. Curr Sci; 56:254-256.

Jamieson et al. (2001) Detection of Lipoprotein(a) in Intraparenchymal Cerebral Vessels: Correlation with Vascular Pathology and Clinical History, Exp. Mol Pathol., 71: 99-105.

Jensen et al. Kinetics for Hybridization of Peptide Nucleic Acids (PNA) with DNA and RNA Studied with the BIAcore Technique Biochemistry. 1997; 36(16):5072-7.

Jin et al. (2003) Inhibition of endothelial lipase causes increased ML cholesterol levels in vivo. J Clin Invest 2003; 111:357-362.

Jones. et al. Computer programs to identify and classify amphipathic of domains. J. Lipid. Res. 33: 287-296 (1992).

Jong, M.C., Dahlmans, V.E., van Gorp, P. J., Brewer, M. L. Mol, M. J., van der Ze, A., Frants, R. R., Hofker, M. H., and Havekes, L. M. Both lipolysis and hepatic uptake of VLDL are impaired in transgenic mice coexpressing human apolipoprotein E*3Leiden human apolipoprotein C-I. Arteriosc. Thromb. Vasc. Biol. 16:934-940 (1996).

Kabanov et al. A new class of antivirals: antisense oligonucleotides combined with a hydrophobic substituent effectively inhibit influenza virus reproduction and synthesis of virus-specific proteins in MDCK cells. FEBS Lett., 1990, 259, 327-330.

Kaler et al (1989) Spontaneous vesicle formation in aqueous mixtures of single-tailed surfactants, Science, 245:1371-1374.

Kandel ER, Schwartz JH, Jessell TM (Eds.) (1991) Principles of Neural Science, Third Edition. Elsevier: New York, pp. 188-189.

Karle et al. (2004) A combined extented and helical backbone for Boc-(Ala-Leu-Ac7C)2-OME, Peptides Res., 63:174-180.

Karle, et al. (1998) Crystal structure of the channel-forming polypeptide antiamoebin in a membrane-mimetic environment. Proc. Natl. Acad. Sci. 95 :5501-5504.

Karle, et al. (2003) Crystal structure of hydrophobic 19-residue peptide helix containing three centrally located D amino acids, PNAS, 100:24:13946-13951.

Kaul, S., et al. (2004) Rapid Reversal of Endothelial Dysfunction in Hypercholesterolemic Apolipoprotein E-Null Mice by Recombinant Apolipoprotein A-I$_{milano}$-Phospholipid Complex. J. Am. Coll. Cardiol. 44:1311-1319.

Kirshenbaum, L.A. et al. Highly Efficient Gene Transfer into Adult Ventricular Myocytes by Recombinant Adenovirus. J Clin. Invest. 92:381-387 (1993).

Kissinger C, Skinner MK, Griswold MD. (1982) Analysis of Sertoli cell-secreted proteins by two-dimensional gel electrophoresis. Biol Reprod. 27(1): 233-240.

Kita, T., Brown, M.S., Watanabe, Y., and Goldstein, J.L. Deficiency of low density lipoprotein receptors in liver and adrenal gland of the WHHL rabbit, an animal model of familial hypercholesterolemia. Proc Natl. Acad. Sci, USA 78: 2268-2272 (1981).

Knowler, W.C. et al. Reduction in the incidence of type 2 diabetes with lifestyle intervention or metformin. N. Engl J Med. (2002) 346(6):393-403.

Ko, et al. (1993) A. Highdensity lipoprotein reduces epidermal growth factor-induced DNA synthesis in vascular smooth muscle cells. Atherosclerosis, 99: 253-259, Abstract.

Kockx, et al. (2004) Apolipoprotein A-I-stimulated Apolipoprotein E Secretion from Human Macrophages Is Independent of Cholesterol Efflux. J. Biol. Chem. 279:25966-25970.

Kolodgie, F.D., Katocs, A.S., Largis, E.E., Wrenn, S.M., Cornhill, J.F., Herdrick, E.E., Lee, S.J., and Virmani, R. Hypercholesterolemia in the rabbit induced by feeding graded amounts of low-level cholesterol. Arterioscler. Thromb. Vasc. Biol. 16:1454-1464 (1996).

Kontos, H.A. and Wei, E.P. (1998) Cerebral arteriolar dilations by KATP channelactivators need L-lysine or L-arginine Am. J. Physiol. 274 (Heart Circ. Physiol. 43): H974-H981, 1998.

Kowal, R.C., Herz, J., Goldstein, J.L., Esser, V., and Brown, M.S. Low density lipoprotein receptor related protein mediates uptake of cholesteryl ester derived from apolipoprotein E enriched lipoproteins. Proc. Natl. Acad. Sci. U.S.A. 86:5810-5814 (1989).

Kozbor D, Lagarde AE, Roder JC. (1982) Human hybridomas constructed with antigen-specific Epstein-Barr virus-transformed cell lines. Proc Natl Acad Sci USA, 79(21): 6651-55.

Kreiger (1999) Charting the Fate of the Good Cholesterol: Identifcation and Characterization of the High-Density Lipoprotein Receptor Sr-Bi. Ann Rev. Biochem. 68: 523-558.

Kullman et al. (1999) Evaluation of the Enantiomeric Composition of Amino Acids in Tobacco, Chirality, 11:669-673.

Kumar et al. (2002) A novel peptide derivative exhibits anti inflammatory and antioxidant activity in adjuvant induced arthritis in rats. Mol Cell Biochem, Jan; 229 (1-2):9-17.

Kume et al. (1992) Lysophosphatidylcholine, a component of atherogenic lipoproteins, induces mononuclear leukocyte adhesion molecules in cultured human and rabbit arterial endothelial cells. J Clin Invest. 90:1138-1144.

Kwiterovich, P.O. State-of-the-art update and review: clinical trials of lipid-lowering agents. Am. J. Cardiol. 82: 3U-17U (1998).

La Salle, G. et al, An adenovirus vector for gene transfer into neurons and glia in the brain. Science. 259:988-990 (1993).

Lalazar, a. et al. (1988) Site-specific Mutagenesis of Human Apolipoprotein E: Receptor Binding Activity of Variants With Single Amino Acid Substitutions. J. Biol. Chem. 263, 3542-2545.

(56) References Cited

OTHER PUBLICATIONS

Lawrence, M.B. and Springer, T.A. (1991) Leukocytes roll on a selectin at physiologic flow rates: distinction from and prerequisite for adhesion through integrins. Cell. 65:859-873.

Lee, S. et al. (2001) Vitamin C-induced decomposition of lipid hydroperoxides to endogenous genotoxins. Science. 292:2083-2086.

Legrand et al. (1992) Molecular Interactions between Human Lactotransferrin and the Phytohemagglutinin-Activated Human Lymphocyte Lactotransferrin Receptor Lie in Two Loop-Containing Regions of the N-Terminal Domain I of Human Lactotransferrin, Biochemistry, 31, 9243-9251.

Letsinger et al. Cholesteryl-conjugated oligonucleotides: Synthesis, properties, and activity as inhibitors of replication of human immunodeficiency virus in cell culture. Proc. Natl. Acad. Sci. USA. 1989. 86. 6553-6556.

Levine, et al. (1993) In vivo protection against endotoxin by plasma high density lipoprotein. Proc. Natl. Acad. Sci. USA, 90:12040-12044.

Li et al. (1993) An atherogenic diet rapidly induces VCAM-1, a cytokine-regulatable mononuclear leukocyte adhesion molecule, in rabbit aortic endothelium. Arteriosclerosis and Thrombosis, 13:197-204.

Li, et al. (2004) Double Belt Structure of Discoidal High Density Lipoproteins: Molecular Basis for Size Heterogeneity. J. Mol. Biol. 343:1293-1311.

Libby et al. (2002) Inflammation and atherosclerosis. Circulation. 105:1135-1143.

Linsel-Nitschke, P. et al. HDL as a target in the treatment of atherosclerotic cardiovascular disease. Nat Rev Drug Discov. (2005) 4(3):193-205.

Mach et al. (1998) Reduction of atherosclerosis in mice by inhibition of CD40 signalling. Nature, 394:200-203.

Mahley et al. Remnant lipoprotein metabolism: key pathways involving cell-surface heparan sulfate proteoglycans and apolipoprotein E. J. Lipid Res. 40: 1-16. (1999).

Mahley et al. Pathogenesis of type III hyperlipoproteinemia (dysbetalipoproteinemia): questions, quandaries, and paradoxes. J. Lipid Res. 40: 1933-1949. (1999).

Mahley, R.W., Weisgraber, K.H., Hussain, M.M., Greenman, B., Fishe, M., Vogel, T., and Gorecki, M. Intravenous infusion of apolipoprotein E accelerates clearance of plasma lipoproteins in rabbits. J. Clin. Invest. 83: 2125-2130 (1989).

Mala, John Geraldine Sandana et al., (Aug. 2001) "Strain improvement of Aspergillus niger for enhanced lipase production", J Gen Appl Microbiol, 47(4):181-186.

Manikandan et al. (2002) Antioxidant potential of a novel tetrapeptide derivative in isoproterenol-induced myocardial. Pharmacology, 65:105-109.

Manoharan et al. Cholic acid-oligonucleotide conjugates for antisense applications Bioorg. Med. Chem. Let., 1994, 4, 1053-1060.

Manoharan et al. Lipidic nucleic acids. Tetrahedron Lett., 1995, 36, 3651-3654.

Marks et al. By-passing immunization. Human antibodies from V-gene libraries displayed on phage. J. Mol. Biol., 222:581, 1991.

Massie et al. Construction of a Helper-Free Recombinant Adenovirus That Expresses Polyomavirus Large T Antigen Mol. Cell. Biol. 6:2872-2883 (1986).

Mato et al. (1996) Involvement of specific macrophage-lineage cells surrounding arterioles in barrier and scavenger function in brain cortex, Proc. Natl. Acad. Sci. USA, vol. 93, pp. 3269-3274, Apr. 1996.

Mazoyer E, Levy-Toledano S, Rendu F, Hermant L, Lu H, Fiat AM, Jolles P, Caen J. KRDS, a new peptide derived from human lactotransferrin, inhibits platelet aggregation and release reaction. Eur J Biochem 1990;194:43-49.

McGarry JD.Banting lecture 2001: dysregulation of fatty acid metabolism in the etiology of type 2 diabetes.Diabetes. Jan. 2002;51(1):7-18.

Meera et al. (1999) Inhibition of neutrophil derived lysosomal enzymes and reactive oxygen species by a novel tetrapeptide. Inflamm Res. Sep. 1999, 48(9):479-84.

Mehrabian et al. (2002) Identification of 5-lipoxygenase as a major gene contributing to atherosclerosis susceptibility in mice. Circ Res. 91:120-126.

Mendez et al. (1994) Synthetic Amphipathic Helical Peptides that Mimic Apolipoprotein A-I in Clearing Cellular Cholesterol. J Clin Invest 94: 1698-1705.

Merrifield et al. (1995) Retro and Retroenantio Analogs of Cecropin-Melittin Hybrids Proc Natl Acad Sci USA 92: 3449-3453.

Mertens, A., et al. (2003) Increased Low-Density Lipoprotein Oxidation and Impaired High-Density Lipoprotein Antioxidant Defense Are Associated With Increased Macrophage Homing and Atherosclerosis in Dyslipidemic Obese Mice: LCAT Gene Transfer Decreases Atherosclerosis. Circulation. 107:1640-1646.

Miller et al. Redesign of Retrovirus Packaging Cell Lines to Avoid Recombination Leading to Helper Virus Production Mol. Cell. Biol. 6: 2895 (1986).

Mims, M. P., et al. (1994) a Nonexchangeable Apolipoprotein E Peptide That Mediates Binding to the Low Density Lipoprotein Receptor. J. Biol. Chem. 269, 20539-20647.

Mishra et al. (1994) Interaction of Synthetic Peptide Analogs of the Class A Amphipathic Helix with Lipids: Evidence for the Snorkel Hypothesis. J Biol. Chem. 269: 7185-7191.

Mishra et al. (1995) Effect of the Arrangement of Tandem Repeating Units of Class A Amphipathic a-Helixes on Lipid Interaction. J. Biol. Chem. 270: 1602-1611.

Mishra et al. (1996) Interaction of Model Class A1, Class A2, and Class Y Amphipathic Helical Peptides with Membranes. Biochemistry 35:11210-11220.

Mishra et al. (1998) Studies of Synthetic Peptides of Human Apolipoprotein A-I Containing Tandem Amphipathic a-Helixes Biochemistry 37: 10313-10324.

Mishra et al. (2001) Solution NMR structure of a model class A (apolipoprotein) amphipathic a helical nentide Pentides 22:567-573.

Mishra et al. (2006) Association of a model class A (apolipoprotein) amphipathic alpha helical peptide with lipid: high resolution NMR studies of peptide.lipid discoidal complexes. J. Biol. Chem. 281:6511-6519.

Miyazaki et al. (1995) Intravenous Injection of Rabbit Apolipoprotein A-I Inhibits the Progression of Atherosclerosis in Cholesterol-Fed Rabbits Arterioscler. Thromb. Vasc. Biol. 15:1882-1888.

Chiesa, G., Monteggia, E., Marchesi, M., Lorenson, L., Laucello, M., Loruso, V., DiMario, C., Karvouni, E., Newton, R.S., Bisgaier, C.L., Franceshini, G. and Sirtori, C.R. Recombinant apolipoprotein A-I(Milano) infusion into rabbit carotid artery rapidly removes lipid from fatty streaks. Circ. Res. 90:974-980, 2002.

Moore DJ, Hussain Aa, Marshall J. (1995) Age-related variation in the hydraulic conductivity of Bruch's membrane. Invest Ophthalmol Vis Sci. 36(7): 1290-1297.

Morrison et al. Chimeric human antibody molecules: Mouse antigen-binding domains with human constant region domains Proc. Natl. Acad. Sci. USA, 81:6851-6855 (1984).

Morsy et al. Efficient Adenoviral-mediated Ornithine Transcarbamylase Expression in Deficient Mouse and Human Hepatocytes. J. Clin. Invest. 92:1580-1586 (1993).

Moullier et al. Correction of lysosomal storage in the liver and spleen of MPS VII mice by implantation of genetically modified skin fibroblast. Nature Genetics. 4:154-159 (1993).

Mulder et al. (2004) Low-density lipoprotein receptor-knockout mice display impaired spatial memory associated with a decreased synaptic density in the hippocampus, Neurobiology of Disease 16: 212-219.

Mulligan, R.C. The basic science of gene therapy. Science. 260:926-932 (1993).

Murugesan et al. (1994) High-density lipoprotein stimulates endothelial cell movement by a mechanism distinct from basic fibroblast growth factor. Circ. Res. 74 : 1149-1156.

Nag et al. (1997) Cerebrovascular Changes in Chronic Hypertension Protective Effects of Enalapril in Rats, Stroke, 28: 1028-1034.

(56) References Cited

OTHER PUBLICATIONS

Nagata et al. (1994) Distribution of free D-serine in vertebrate brains, Brain Res., 634: 291-295.
Nagata et al. (1995) Free D-serine concentration in normai and Alzheimer human brain, Brain Res. Bull., 38(2): 181-183.
Nagata et al. (2002) Hemodynamic Aspects of Alzheimer's Disease, Ann. N. Acad. Sci., 977: 391-402.
Naghavi M, Wyde P, Litovsky S, Madjid M, Akhtar A, Naguib S, Siadaty MS, Sanati S, Casscells W. (2003) Influenza infection exerts prominent inflammatory and thrombotic effects on the atherosclerotic plaques of apolipoprotein E-deficient mice. Circulation. 107(5): 762-768.
Nakamura et al. (1997) Deposition of amyloid B protein (AB) subtypes [AB40 and AB42(43)] in canine senile plaques and cerebral amyoloid angiopathy Acta Neuropathot 94: 323-328.
Nanjee et al. (1999) Acute effects of intravenous infusion of apoA-Uphosphos-phatidycholine discs on plasma lipoproteins in humans. Arterioscler Thromb Vase Biol, 19:979-989.
Nanjee et al. (2001) Intravenous apoA-1/lecithin discs increase preconcentration in tissue fluid and stimulate reverse cholesterol transport in humans. J Lipid Res, 42:1586-1593.
Navab et al. (1991) Monocyte transmigration induced by modification of low density lipoprotein in cocultures of human aortic wall cells is due to induction of monocyte chemotactic protein 1 synthesis and is abolished by high density lipoprotein. Journal of Clinical Investigation 1991;88:2039-2046.
Navab et al. (1997) Mildly oxidized LDL induces an increased apolipoprotein J/paraoxonase ratio. J Clin.Invest. 99: 2005-2019.
Navab et al. (2000) Normal high density lipoprotein inhibits three steps in the formation of midly oxidized low density lipoprotein: step 1. J Lipid Res. 41: 1481-1494.
Navab et al. (2000) Normal high density lipoprotein inhibits three steps in the formation of mildly oxidized low density lipoprotein: steps 2 and 3. J. Lipid Res. 41:1495-1508.
Navab et al. (2001) A cell-free assay for detecting HDL that is dysfunctional in preventing the formation of or inactivating oxidized phospholipids. J Lipid Res 2001; 42:1308-1317.
Navab et al. (2001) HDL and the inflammatory response induced by LDL-derived oxidized phospholipids. Arterioscler Thromb Vasc Bio. 21:481-488.
Navab et al. (2003) Oral synthetic phospholipids (DMPC) raises high- density lipoprotein cholesterol levels, improves high-density lipoprotein function, and markedly reduces atherosclerosis in apolipoprotein E-null mice. Circulation 2003; 108:1735-1739.
Navab et al. (2004) Oral D-4F causes formation of pre-high-density lipoprotein and improves high-density lipoprotein-mediated cholesterol efflux and reverse cholesterol transport from macrophages in apoE-null mice, Circulation 109:r120-r125.
Navab et al. (2004) The oxidation hypothesis of atherogenesis: the role of oxidized phospholipids and L. J. Lipid Res. 45: 993-1007.
Navab et al. (2005) The double jeopardy of HDL. Annals of Medicine 37:173-178.
Navab et al. (2005) Apolipoprotein A-I Mimetic Peptides. Arterioscler Thromb Vasc Biol 25:1325-1331.
Navab et al. (2005) D-4F and Statins Synergize to Render HDL Antiinflammatory in Mice and Monkeys and Cause Lesion Regression in Old Apolipoprotein E—Null Mice. Arterioscler Thromb Vasc Biol 25:1426-1432.
Navab et al. (2005) An oral ApoJ peptide renders HDL anti-inflammatory in Mice and Monkeys and dramatically reduces atherosclerosis in Apolipoprotein E-null mice. Arterioscler Thromb Vasc Biol 25:1932-1937.
Navab et al. (2005) The Role of High-Density Lipoprotein in Inflammation Cardiovascular Medicine 15:158-161.
Navab et al. (2005) An Apolipoprotein A-I Mimetic Works Best in the Presence of Apolipoprotein A-I Circ. Res. 25:1085-1086.
Navab et al. (2005) Oral Small Peptides render HDL antiinflammatory in mice, and monkeys and reduce atherosclerosis in ApoE null mice. Circ Res. 2005, 97:524-532.
Navab M, et al. (2002) Oral administration of an Apo A-I mimetic Peptide synthesized from D-amino acids dramatically reduces atherosclerosis in mice independent of plasma cholesterol. Circulation. 105(3): 290-292.
Navab, M., et al. (2004) Oral D-4F causes formation of pre-beta high-density lipoprotein and improves high-density lipoprotein-mediated cholesterol efflux and reverse cholesterol transport from macrophages in apolipoprotein E-null mice. Circulation 109:3215-3220.
Navab, M., et al., (2004) Apparent Paradox of Low-Fat "Healthy" Diets Increasing Plasma Levels of Oxidized Low-Density Lipoprotein and Lipoprotein(a). Arterioscler Thromb Vasc Biol 24:392-393.
Nguyen et al. (2006) Apolipoprotein A-I-mimetic peptides with antioxidant actions Arch Biochem. Biophys. 451:34-42.
Houstis, N. et al. (2006) Reactive oxygen species have a causal role in multiple forms of insulin resistance. Nature. 440:944-948 (2006).
Nicholls, S.J. et al. Relationship Between Atheroma Regression and Change in Lumen Size After Infusion of Apolipoprotein A-I Milano. J Am Coll Cardiol. (2006) 47(5):992-7.
Nicholls, S.J., Zeng, L., and Hazen, S.L. Formation of dusfunctional high-density lipoprotein by myeloperoxidase. Trrends Crdiovasc. Med. 15: 212-219 (2005).
Nikoulin, I.R. et al. (1998) An Apolipoprotein E Synthetic Peptide Targets to Lipoproteins in Plasma and Mediates Both Cellular Lipoprotein Interactions in Vitro and Acute Clearance of Cholesterol-rich Lipoproteins in Vivo. J. Clin Invest. 101, 223-234.
Nielsen et al., Sequence-Selective Recognition of DNA by Strand Displacement with a Thvmine-Substituted Polvamide Science. 254. 1497-1500 (1991).
Nievelstein et al. (1991) Lipid accumulation in rabbit aortic intima two hours after bolus infusion of low density lipoprotein: a deep-etch and immunolocalization study of ultra-rapidly frozen tissue. Arteriosclerosis and Thrombosis, 11: 1795-1805.
Nirmala, C. and Puvanakrishnan, R. (1996) Effect of curcumin on certain lysosomal hydrolases in isoproterenol-induced myocardial infarction in rats. Biochem Pharmacol. Jan. 12, 1996;51(1):47-51.
Nirmala et al. (1999) Curcumin treatment modulates collagen metabolism in isoproterenol induced myocardial necrosis in rats. Mol Cell Bioche, Jul. 1999; 197 (1-2):31-37.
Nissen, S.E., et al. Effect of Recombinant ApoA-I Milano on Coronary Atherosclerosis in Patients With Acute Coronary Syndromes: A Randomized Controlled Trial. (2003) JAMA 290:2292-2300.
Nofer, J.R., van der Giet, M., Tolle, M., Wolinska, I., von Wnuck Lipinski, K., Baba, H. A., Tietge, U.J., Godecke, A., Ishii, I., Kleuser, B., Schafers, M., Fobker, M., Zidek, W., Assmann, G., Chun, J., and Levkau, B. HDL induces NO-dependent vasorelaxation via the lysophosphoreceptor S1P3. J. Clin. Invest. 113:569-581 (2004).
Nomoto et al. (1998) Improvement of Intestinal Absorption of Peptide Drugs by Glycosylation: Transport of Tetrapeptide by the Sodium Ion-Dependent D-Glucose Transporter, Jrnl of Phar, Sci, vol. 87, No. 3, Mar. 1998, pp. 326-332.
Norton et al., Targeting Peptide Nucleic Acid-Protein Conjugates to Structural Features Within Duplex DNA Bioorg Med Chem. Apr. 1995; 3(4):437-45.
Nuttall ME, Gimble JM. (2000) Is there a therapeutic opportunity to either prevent or treat osteopenic disorders by inhibiting marrow adipogenesis? Bone. 27(2): 177-184.
Oberhauser et al., Effective incorporation of 2'-O-methyl-oligoribonucleotides into liposomes and enhanced cell association through modification with thiocholesterol. Nucl. Acids Res., 1992, 20, 533-538.
O'Brien et al. (1996) Neovascular expression of E-selectin, intercellular adhesion molecule-1, and vascular cell adhesion molecule- 1 in human atherosclerosis and their relation to intimal leukocyte content. Circulation 1996; 93: 672-82.
Obunike, J.C., Pillarasetti, S., Paka, L., Kako, Y., Butteri, M.J., Ho, Y-Y., Wagner, W.D., Yamada, N., Mazzone, T., Deckelbaum, R.J., and Goldberg, I. (2000) The heparin-binding proteins apolipoprotein E and lipoprotein lipase enhance cellular proteoglycan production. Arterio. Thromb. Vasc. Biol. 20:111-118 (2000).
0'Connell BJ, Genest J Jr. High-density lipoproteins and endothelial function. Circulation. 2001;104:1978-1983.

(56) References Cited

OTHER PUBLICATIONS

Oguchi et al. (2000) Monoclonal antibody against vascular cell adhesion molecule-1 inhibits neointimal formation after periadventitial carotid artery injury in genetically hypercholesterolemic mice. Arterioscler Thromb Vasc Biol; 20:1729-1736.
Oram and Heinecke (2005) ATP-Binding Cassette Transporter A1: A Cell Cholesterol Exporter That Protects Against Cardiovascular Disease. Physiol Rev. 85: 1343-1372.
Oram and Yokoyama (1996) Apolipoprotein mediated removal of cellular cholesterol and phospholipids. J Lipid Res. 37: 2473-2491.
Otvos, J.D. et al. Low-density lipoprotein and high-density lipoprotein particle subclasses predict coronary events and are favorably changed by gemfibrozil therapy in the Veterans Affairs High-Density Lipoprotein Intervention Trial. Circulation. (2006);113(12):1556-63.
Ou et al. (2003) AP-4F, antennapedia peptide linked to an amphipathic a helical peptide, increases the efficiency of lipofectamine-mediated gene transfection in endothelial cells. Biochem Biophys Res Commun 2003;305:605-610.
Ou et al. (2003) L-4F, an apolipoprotein A-1 mimetic, dramatically improves vasodilation in hypercholesterolemic and sickle cell disease. Circulation 2003; 107:2337-2341.
Ou et al. (2005) Effects of D-4F on Vasodilation and Vessel Wall Thickness in Hyperholesterolemic LDL Receptor—Null and LDL Receptor/Apolipoprotein A-I Double-Knockout Mice on Western Diet. Circ. Res. 97;1190-1197.
Ou et al., L-4F, an apolipoprotein A-I mimetic, restores nitric oxide and superoxide anion balance in low-density lipoprotein-treated endothelial cells. Circulation 2003; 107:1520-1524.
Owens BJ, Anantharamaiah GM, Kahlon JB, Srinivas RV, Compans RW, Segrest JP. (1990) Apolipoprotein A-I and its amphipathic helix peptide analogues inhibit human immunodeficiency virus-induced syncytium formation. J Clin Invest. 86(4): 1142-1150.
Paigen et al. (1990) Atherosclerosis Susceptibility Differences among Progenitors of Recombinant Inbred Strains of Mice. Arteriosclerosis 10: 316-323.
Paka et al. Apolipoprotein E Containing High Density Lipoprotein Stimulates Endothelial Production of Heparan Sulfate Rich in Biologically Active Heparin-like Domains J. Biol. Chem. 274: 4816-4823 (1999).
Palgunachari et al. (1996) Only the Two End Xelises of Eight Tandem Amphipathic Helical Domaine of Human Apo A-I Have Significant Lipid Affinity. Arteriosclerosis, Thrombosis, & Vascular Biology 16: 328-338.
Palinski et al. (1994) ApoE-Deficient Mice Are a Model of Lipoprotein Oxidation in Atherogenesis: Demonstration of Oxidation-Specific Epitopes in Lesions and High Titers of Autoantibodies to Malondialdehyde-Lysine in Serum. Arteriosclerosis & Thrombosis. 14(4):605-616.
Pan, T.C., et al. Rabbit apolipoprotein A-I mRNA and gene: Evidence that rabbit apolipoprotein A-I is synthesized in the intestine but not in the liver. Eur. J. Biochem. 30:99-104, 1987.
Panizzutti et al. (2001) A New Strategy to Decrease N-methyl-D-aspartate (NMDA) Receptor Coactivation. Inhibition of D-serine Synthesis by Converting Serine Racemase into an Eliminase PNAS 98:5294-5299.
Papo et al. (2002) The consequence of sequence alteration of an amphipathic a-helical antimicrobial peptide and its diastereomers. J. Biol. Chem.2002;277(37): 33913-33921.
Pappenheimer et al. (1994) Intestinal Absorption and Excretion of Octapeptides Composed of D Amino Acids Proc Nail Acad Sci USA 91: 1942-1945.
Pappenheimer et al. (1997) Absorption and Excretion of Undegradable Peptides: Rols of Lipid Solubility and Net Charge. J. Pharmacology & Experimental Therapeutics 280(1):292-300.
Pardridge et al., Vector-mediated delivery of a polyamide ("peptide") nucleic acid analogue through the blood-brain barrier in vivo. Proc Natl Acad Sci USA. 1995; 92(12):5592-6.
Parhami F, Morrow AD, Balucan J, Leitinger N, Watson AD, Tintut Y, Berliner JA, Demer LL. (1997) Lipid oxidation products have opposite effects on calcifying vascular cell and bone cell differentiation. A possible explanation for the paradox of arterial calcification in osteoporotic patients. Arterioscler Thromb Vasc Biol. 17(4): 680-687.
Pasceri et al. Direct proinflammatory effect of C-reactive protein on human endothelial cells. Circulation. 2000;102:2165-2168.
Pasceri etl al. (2001) Modulation of Creactive protein-mediated monocyte chemoattractant protein-1 induction in human endothelial cells by anti-atherosclerosis drugs, Circulation. 2001;103:2531-2534.
Pasqui AL, Puccetti L, Di Renzo M, Bruni F, Camarri A, Palazzuoli A, Biagi F, Servi M, Bischeri D, Auteri A, Pastorelli M. (2005) Structural and functional abnormality of systemic microvessels in cardiac syndrome X. Nutr Metab Cardiovasc Dis. 15(1): 56-64.
Pastan et al. A retrovirus carrying an MDR1 cDNA confers multidrug resistance and polarized expression of P-glycoprotein in MDCK cells. PNAS, 85: 4486 (1988).
Patszty et al., (1994) Apolipoprotein A1 Transgene Corrects Apolipoprotein E Deficiency-induced Atherosclerosis in Mice. J. Clinical Investigation 94:899-903.
Pilone (2000) D-amino acid oxidase: new findings. CMLS, Cell. Mol Life Sci, 57: 1732-1747.
Plump et al. (1994) Human apolipoprotein A-I gene expression increases high density lipoprotein and suppresses stherosclerosis in the apolipoprotein E-deficient mouse. Proc. Natl. Acad. Sci. USA 91:9607-9611.
Pohle K, Maffert R, Ropers D, Moshage W, Stilianakis N, Daniel WG, Achenbach S. (2001) Progression of aortic valve calcification: association with coronary atherosclerosis and cardiovascular risk factors. Circulation. 104(16): 1927-1932.
Presta, Antibody engineering. Curr. Opin. Struct. Biol., 2:593-596 (1992).
Purdue News (Oct. 2000) 'Microspheres' Offer Promise for Oral Drug Delivery (3 pages).
Purdue News (Sep. 12, 1997) New Oral Insulin Delivery System Shows Promise (3 pages).
Quyyumi, A.A. (1998) Endothelial Function in Health and Disease: New Insights into the Genesis of Cardiovascular Disease Am. J. Med. 105:32S-39S.
Rader, D.J. (2003) Regulation of Reverse Cholesterol Transport and Clinical Implications. Am. J. Cardiology. 92:42J-49J.
Ragot, T. et al. Replication-defective recombinant adenovirus expressing the Epstein-Barr virus (EBV) envelope glycoprotein gp340 220 induces protective immunity against EBV-induced lymphomas in the cottontop tamarin. J Gen. Virology 74:501-507 (1993).
Raha et al. (1988) KRDS a tetra peptide derived from lactotransferrin inhibits binding of monoclonal antibody against glycoprotein Iib-IIIa on ADP-stimulated platelets and megakaryocytes. Blood 1988;72: 172-178.
Rajarathnam et al. 1H NMR studies of interleukin 8 analogs: characterization of the domains essential for function. Biochemistry 33: 6623-6630 (1994).
Rajashree, S. and Puvanakrishnan, R. (1999) Dexamethasone induced alterations in the levels of proteases involved in blood pressure homeostasis and blood coagulation in rats. Mol Cell Biochem. Jul. 1999;197(1-2):203-8.
Rajashree, S. and Puvanakrishnan, R. (1996) Alterations in certain lysosomal glycohydrolases and cathepsins in rats on dexamethasone administration. Mol Cell Biochem. Jan. 26, 1996;154(2):165-70.
Rajashree, S. and Puvanakrishnan, R. (1998) Dexamethasone induced alterations in enzymatic and nonenzymatic antioxidant status in heart and kidney of rats, Mo! Cell Biochem. Apr. 1998;181(1-2):77-85.
Rall, S. C., Jr., et al. (1982) Structural basis for receptor binding heterogeneity of apolipoprotein E from type III hyperlipoproteinemic subjects. PNAS USA. 79, 4696-4700.
Ram et al. In Situ Retroviral-mediated Gene Transfer for the Treatment of Brain Tumors in Rats Cancer Res. 53:83-88, (1993).
Ramesh et al. (1998) A novel surface-active peptide derivative exhibits in vitro inhibition of platelet aggregation. Peptides 1998;19:1695-1702.

(56) References Cited

OTHER PUBLICATIONS

Ramesh et al. (1998) Effect of a novel tetrapeptide derivative in a model of isoproterenol induced myocardial necrosis. Mol Cell Biochem. Oct. 1998;187(1- 2):173-82.

Ramprasad et al. Sustained-delivery of an apolipoproteinE—peptidomimetic using multivesicular liposomes lowers serum cholesterol levels. J. Controlled Release, 79: 207-218 (2002).

Ranganathan et al. (2000) Channel—forming, self-assembling, bishelical amphiphilic peptides: design, synthesis and crystal structure of Py(Aibn)21 n=2, 3, 4. J Peptide Res. 2000 56:416-426.

Rapp, J.H., Lespine, A., Hamilton, R.L., Colyvas, N., Chaumenton, A.H., Tweedie-Hardman, J. Kotite, L., Kunitake, S.T., Havel, R.J., and Kane, J.P. Triglyceride rich lipoproteins isolated by selected affinity antiapolipoprotein B immunosorption from human atherosclerotic plaque. Athero. Thromb. 14:1767-1774 (1994).

Reape and Groot (1999) Chemokines and atherosclerosis. Atherosclerosis 1999;147:213-225.

Reddy et al. (2001) Human paraoxonase-3 is an HDLassociated enzyme with biological activity similar to paraoxonase-1 protein but is not regulated by oxidized lipids. Arterioscler Thromb Vasc Biol 2001;21:542-547.

Reddy et al. (2004) Potential role for mitogen-activated protein kinase phosphatase-1 in the development of atherosclerotic lesions in mouse models. Arterioscler Thromb Vasc Biol 2004;24:1676-1681.

Remaley et al. (2003) Synthetic amphipathic helical peptides promote lipid efflux from cells by an ABCA1-dependent and an ABCA1-independent pathway. J. Lipid. Res. 44:828-836.

Rencurel, F., Foretz, M., Kaufmann, M. R., Stroka, D., Looser, R., Leclerc, I., de Silva G., Rutter, G.A., Viollet, B., and Meyer, S.A. Stimulation of AMP-activated protein kinase is essential for the induction of drug metabolizing enzymes by Phenobarbital in human and mouse liver. Molecular Pharmacol. 70:1925-1934, (2006).

Rensen, P.C., and van Berkel, T.J. Apolipoprotein E effectively inhibits lipoprotein lipase-mediated lipolysis of chylomicron-like triglyceride-rich lipid emulsions in vitro and in vivo. J. Biol. Chem. 271:14791-14799 (1996).

Ridker, P. M. (2002) On evolutionary biology, inflammation, infection, and the causes of atherosclerosis. Circulation 2002;105:2-4.

Roessler, J. et al. Adenoviral-mediated gene transfer to rabbit synovium in vivo. Clin. Invest. 92:1085-1092 (1993).

Rogers, et al. The lipid-free structure of apolipoprotein A-I: effects of amino-terminal deletions. (1998) Biochemistry 37:11714-11725.

Roher et al. (1993) 18-Amyloid-(142) is a major component of cerebrovascular amyloid deposits: Implications for the pathology of Alzheimer disease Proc. Natl. Acad. Sci., USA, 90: 10836-10840.

Rohlmann, A., Gotthardt, M., Hammer, R.E., and Herz, J. Inducible activation of hepatic LRP gene by cell mediated recombination confirms role of LRP in clearance of chylomicron remnants. J. Clin. Invest. 101:689-695 (1998).

Roman et al. (2002) Subcortical ischaemic vascular dementia, Lancet Neurol., 1: 426-436.

Rong et al. (2001) Elevating high-density lipoprotein cholesterol in apolipoprotein E- eficient mice remodels advanced atherosclerotic lesions by decreasing macrophage and increasing smooth muscle cell content, Circulation, 2001;104:2447-2452.

Rose, D.J. Characterization of antisense binding properties of peptide nucleic acids by capillary gel electrophoresis. Anal Chem. Dec. 15, 1993; 65(24):3545-9.

Rubin et al. (1991) Inhibition of early atherogenesis in transgenic mice by human apolipoprotein AI. Nature 353:265-267.

Sabbatini et al. (2001) Microanatomical changes of intracerebral arteries in spontaneously hypertensive rats: a model of cerebrovascular disease of the elderly Mech. Aging & Dev., 122: 1257-1268.

Saison-Behmoaras et al., Short modified antisense oligonucleotides directed against Ha-ras point mutation induce selective cleavage of the mRNA and inhibit T24 cells proliferation. Embo J., 1991, 10, 1111-1118.

Sandana Mala JG, Kamini NR, Puvanakrishnan R. Strain improvement of *Aspergillus niger* for enhanced lipase production. J Gen Appl Microbiol. Aug. 2001; 47 (4):181-186.

Sattler W, Stocker R. Greater selective uptake by Hep G2 cells of highdensity lipoprotein cholesteryl ester hydroperoxides than of unoxidized cholesterylesters. Biochem J. 1993;294:771-778.

Schmitz-Peiffer C. Signaling aspects of insulin resistance in skeletal muscle: mechanisms induced by lipid oversupply. Cell Signal. Oct. 2000;12(9-10):583-94. Review.

Schnolzer et al. Constructing proteins by dovetailing unprotected synthetic peptides: backbone-engineered HIV protease. Science 256: 221 (1992).

Schonbeck, U. and Libby, P. (2004) Inflamation, Immunity, and HMG-COA Reductase Inhibitors, Statins as Anti inflammatory Agents? Circulation 109(21 Suppl 1): II18-II26.

Schonfeld et al. Lipolysis produces changes in the immunoreactivity and cell reactivity of very low density lipoproteins. J. Clin. Invest. 64: 1288-1297 (1979).

Segrest et al, (1974) A Molecular Theory of Lipid-Protein Interaction in the Plasma Lipoproteins. FEBS Left. 38: 247-253.

Segrest et al. (1992) The Amphipathic Helix in the Exchangeable Apolipoproteins: A Review of Secondary Structure and Function J Lipid Research 33:141-166.

Segrest et al. (1990) Proteins: Structure, Function and Genetics, 8: 103-117.

Segrest et al., Apolipoprotein B-100: conservation of lipid-associating amphipathic secondary structural motifs in nine species of vertebrates. J. Lipid. Res. 39:85-102 (1998).

Segrest et al., Structure of apolipoprotein B-100 in low density lipoproteins. J. Lipid. Res. 42, pp. 1346-1367 (2001).

Segrest et al. apoB-100 has a pentapartite structure composed of three amphipathic alpha-helical domains alternating with two amphipathic beta-strand domains. Detection by the computer program LOCATE. (1994) Arteriosclerosis and Thrombosis 14:1674-1685.

Senior (1999) New options developed for needle-free drug delivery. Lancet, 1998:354:1102.

Seth, et al., Role of a low-pH environment in adenovirus enhancement of the toxicity of a Pseudomonas exotoxin-epidermal growth factor conjugate. J. Virol. 51:650-655 (1984).

Seth, et al., Evidence that the Penton Base of Adenovirus Is Involved in Potentiation of Toxicity of Pseudomonas Exotoxin Conjugated to Epidermal Growth Factor. Mol. Cell. Biol. 4:1528-1533 (1984).

Shah et al. (1998) Effects of recombinant apolipoprotein A-I(Milano) on aortic atherosclerosis in apolipoprotein E-deficient mice. Circulation, 1998:97(8): 780-785.

Shah et al. (2001) High-dose recombinant apolipoproteins A-Imilano mobilizes tissue cholesterol and rapidly reduces plaque lipid and macrophase content in apolipoprotein Edeficient mice: potential implications ofr acute plaque stabilization. Circulation. 2001; 103:3047-3050.

Shah, P.K. et al. Apolipoprotein A-I mimetic peptides: potential role in atherosclerosis management. . (2005) Trends Cardiovasc. Med. 15:291-296.

Shea et al., Synthesis, hybridization properties and antiviral activity of lipid-oligodeoxynucleotide conjugates. Nucl. Acids Res., 1990, 18, 3777-3783.

Shen, B.W., Scanu, A.M., and Kezdy, F.J. Structure of human serum lipoproteins inferred from compositional analysis. Proc. Natl. Acad. Sci. U.S.A. 74:837-841 (1977).

Shih et al. (1999) Minimally modified low-density lipoprotein induces monocyte adhesion to endothelial connecting segment-1 by activating beta integrin. J Clin Invest 1999; 103:613-625.

Shih et al. (2000) Combined serum paraoxonase/apolipoprotein E knockout mice exhibit increased lipoprotein oxidation and atherosclerosis. I Biol. Chem., 2000; 275:17527-17535.

Shimono, H. N., et al., Plasma lipoprotein metabolism in transgenic mice overexpressing apolipoprotein E. Accelerated clearance of lipoproteins containing apolipoprotein B. (1992) Eur. J. Clin. Invest. 90, 2084-2991.

Shishehbor et al. (2003) Association of nitrotyrosine levels with cardiovascular disease and modulation by statin therapy. JA 2003:289:1675-1680.

(56) References Cited

OTHER PUBLICATIONS

Silkensen et al., Identification of clusterin sequences mediating renal tubular cell interactions; J Peptide Res., 1999,54:449-547.

Singh et al. (2000) Innate defences against viremia, Rev Med Virol 2000, 10:395-403.

Sonntag et al. (1997) Decreases in Cerebral Microvasculature with Age Are Associated with the Decline in Growth Hormone and insulin-Like Growth Factorl, Endocrinol 138(8): 3515-3520.

Sorescu et al. NAD(P)H oxidases and their relevance to atherosclerosis. Trends Cardiovas Med 2001;11:124-131.

Sparrow, C.P., Baffle, J., Lam, M.H., Lund, E.G., Adams, A.D., Fu, X, Haynes, N., Jones, A.B., Macnaul, K.L., Ordeyka, J., Singh, S., Wang, J., Zhou, G., Moller, D.E., Wright, S.D., and Menke, J.G. A potent synthetic LXR agonist is more effective than cholesterol loading at inducing ABC A1-mRNA and stimulating cholesterol efflux. J. Biol. Chem. 277:10021-10027 (2002).

Spieker et al. (2002) High-density lipoprotein restores endothelial function in hypercholesterolemic men. Circulation. 2002;105:1399-1402.

Sprecher et al. (1993) The Low HDL Cholesterol/ High Triglyceride Trait Arterioscler. Thromb. 13: 495-504.

Springer, T.A. (1990) Adhesion receptors of the immune system. Nature 1990; 346:425-434.

Srinivas et al. (1990) Antivrial Effects of Apolipoprotein A-I and Its Synthetic Amphipathic Peptide Analogs. Virology. 176:48-57.

Stannard et al. (2001) Inability of plasma high-density lipoproteins to inhibit cell adhesion molecule expression in human coronary artery endothelial cells. Atherosclerosis. 2001;154:31-38.

Steplewski et al. Isolation and characterization of anti-monosialoganglioside monoclonal antibody 19-9 class-switch variants. PNAS 82: 8653 (1985).

Sugatani et al. (1996) High-density lipoprotein inhibits the synthesis of platelet-activating factor in human vascular endothelial cells. J Lipid Mediators Cell Signal. 1996:13:73-88.

Sumitra et al. (2001) Experimental myocardial necrosis in rats: role of arjunolic acid on platelet aggregation, coagulation and antioxidant status. Mol Cell Biochem. 2001; 224(1-2).

Suresh, R. et al. (1992) Alterations in human gingival glycosaminoglycan pattern in inflammation and in phenytoin induced overgrowth. Mol Cell Biochem. Oct. 7, 1992; 115(2):149-54.

Svensson, U. Role of vesicles during adenovirus 2 internalization into HeLa cells. J. Virology 55:442-449 (1985).

Swain, J. et al. Prooxidant iron and copper, with ferroxidase and xanthine oxidase activities in human atherosclerotic material. (1995) FEBS Lett. 368(3):513-515.

Swarnakar et al. The apolipoprotein E-dependent low density lipoprotein cholesteryl ester selective uptake pathway in murine adrenocortical cells involves chondroitin sulfate proteoglycans and an alpha 2-macroglobulin receptor. J. Biol. Chem. 276: 21121-21126 (2001).

Swift, L.L. et al., A recycling pathway for resecretion of internalized apolipoprotein E in liver cells. (2001) J. Biol. Chem. 276:22965-22970.

Takahashi, S.Y., Kawarabayasi, T., Nakai, J., Sakai and Yamamoto, T. Rabbit very low density lipoprotein receptor-a low density receptor like protein with distinct ligand specificity. Proc. Natl. Acad. Sci. U.S.A. 89: 9252-9256 (1992).

Tan et al. (1997) A Novel, highly Efficient Peptide-HLA Class TH:ca Binding Assay using unfolded heavy change molecules: Identification of HIV-1 Derived Peptides that Bind to FILA-A* 0201 and HLA-A* 0301, J Immunol Methods, 205:201-209.

Thomas, Eric C. (1999) Brain macrophages: on the role of pericytes and perivascular cells, Brain Res. Rev., 31: 42-57.

Throngate, F.E. et al., Low levels of extrahepatic nonmacrophage ApoE inhibit atherosclerosis without correcting hypercholesterolemia in ApoE-deficient mice. (2000) Arterio. Thromb. Vasc. Biol. 20:1939-1945.

Tian et al. (2002) Structure-affinity relationships in the gp4l Eldkwa epitope for the HIV-1 neutralizing monoclonal antibody 2F5: effects of side-chain and backbone modifications and conformational constraints, J. Peptide Res. 59, 2002, 264-276.

Toyoda, Kazunori et al (1997) Effect of Aging on Regulation of Brain Stem Circulation During hypotension, J. Cerebral Blood Flow & Metab., 17(6): 680-685.

Triaggiai et al., An efficient method to make human monoclonal antibodies from memory B cells: potent neutralization of SARS coronavirus, Nat Med. Aug. 2004;10(8):871-5 (2004).

Tsai et al. (1998) D-serine added to antipsychotics for the treatment of schizophrenia. Biol. Psychiatry, 44: 1081-1089.

Tsao et al. (2001) Hibernation-induction Peptide and Cell Death: D-Ala2, D-Leulenkephalin Blocks Bax-related Apoptotic Processes. European Journal of Pharmacology 428:149-151.

Tsimikas et al. (2001) Measuring Circulating Oxidized Low-Density Lipoprotein to Evaluate Coronary Risk. Circulation 103:1930-1932.

Tward et al. (2002) Decreased atherosclerotic lesion formation in human serum paraoxonase transgenic mice, Circulation 2002;106:484-490.

Tytler et al. Reciprocal effects of apolipoprotein and lytic peptide analogs on membranes. Cross-sectional molecular shapes of amphipathic alpha helices control membrane stability. J. Biol. Chem. 268: 2212-2218 (1993).

Valabhji, J., et al., (2001) High-density lipoprotein composition and paraoxonase activity in Type I diabetes. Clinical Science. 101:659-670.

Van Leeuwen R, Klaver CC, Vingerling JR, Hofman A, de Jong PT. (2003) Epidemiology of age-related maculopathy: a review. Eur J Epidemiol. (9): 845-854.

Van Lenten et al. (2002) Influenza infection promotes macrophage traffic into arteries of mice that is prevented by D-4F, an apolipoprotein A-I mimetic peptide. Cir 2002, 106:1127-1132.

Van Lenten, BJ. et al. (2001) High-density lipoprotein loses its anti-inflammatory properties during acute influenza A infection, Circulation 2001; 103:2283-2288.

Van Lenten, et al. (1995) Anti-inflammatory HDL Becomes Pro-inflammatory during the Acute Phase Response, J. Clin. Invest., vol. 96, Dec. 1995, 2758-2767.

Van Lenton et al. (2004). D-4F an ApoA-I mimetic peptide inhibits the inflammatory response induced by influenza A infection of human type II pneumocytes, Circulation: 110:3252-3258.

Varga et al., Infectious entry pathway of adenovirus type 2. J. Virology 65:6061-6070 (1991).

Venugopal et al. (2002) Demonstration that C-reactive protein decreases eNOS expression and bioactivity in human aortic endothelial cells. Circulation. 2002; 106:1439-41.

Verhoeyen et al., Reshaping human antibodies: grafting an antilysozyme activity. Science, 239:1534-1536 (1988).

Vinters et al. (1998) Secondary microvascular degeneration in amyloid angiopathy of patients with hereditary cerebral hemorrhage with amyloidosis, Dutch type (HCHWA-D), Acta Neuropathol. 95: 235-244.

Vovenko, Eugene (1999) Distribution of oxygen tension on the surface of arterioles, capillaries and venules of brain cortex and in tissue in normoxia; an experimental study on rats. Eur. J. Physiol., 437: 617-623.

Wake AK, Datta G, Palgunachari MN, Mishra VK, Anatharamaiah GM, White RG. Apolipoprotein A-1 mimetic peptide retains function after oxidant exposure. Proc ASME 2008 Summer Bioenginerring Conference (Marco Island, Florida), Jun. 25-29, 2008, SBC2008-189660.

Walpola et al. (1995) Expression of ICAM-1 and VCAM-1 and monocyte adherence in arteries exposed to altered shear stress. Arterioscler Thromb Vasc Biol, 15:2-10.

Watson et al. (1995) Effect of platelet activating factor-acetylhydrolase on the formation and action of minimally oxidized-low gensitylipoprotein. J Clin Invest. 1995; 95:774-782.

Watson et al. (1995) Protective effect of high density lipoprotein associated paraoxonase Inhibition of the biological activity of minimally oxidized low density lipoprotein. J Clin Invest 1995;96:2882-2891.

Watts et al. Dyslipoproteinaemia and hyperoxidative stress in the pathogenesis of endothelial dysfunction in non-insulin dependent diabetes mellitus: an hypothesis. Atherosclerosis 141: 17-30 (1998).

(56) References Cited

OTHER PUBLICATIONS

Weers PM, Narayanaswami V, Ryan RO. (2001) Modulation of the lipid binding properties of the N-terminal domain of human apolipoprotein E3. Eur J Biochem. 268(13): 3728-3735.

Wei et al. (1998) Antioxidants Inhibit ATP-Sensitive Potassium Channels in Cerebral Arterioles, Stroke, 29: 817-823.

White, C. R., et al., Superoxide and peroxynitrite in atherosclerosis. (1994) Proc. Natl. Acad. Sci. USA. 91:1044-1048.

White, C.R., et al., Circulating plasma xanthine oxidase contributes to vascular dysfunction in hypercholesterolemic rabbits. (1996) Proc. Natl. Acad. Sci. (USA) 93: 8745-8749.

Wickham et al., Integrins alpha v beta 3 and alpha v beta 5 promote adenovirus internalization but not virus attachment. Cell 73:309-319 (1993).

Wilson et al. Three-dimensional structure of the LDL receptor-binding domain of human apolipoprotein E. Science 252: 1817-1822 (1991).

Witztum, J.L. et al. Role of oxidized low density lipoprotein in atherogenesis. J. Clin Invest. 88:1785-1792 (1991).

Wolff JA, Malone RW, Williams P, Chong W, Acsadi G, Jani A, Felgner PL. (1990) Direct gene transfer into mouse muscle in vivo. Science, 247(4949 Pt 1): 1465-8.

Wool GD, Reardon CA, Getz GS. (2008) Apolipoprotein A-I mimetic peptide helix Number and helix linker influence potentially anti-atherogenic properties. J Lipid Res. 49(6): 1268-1283.

Wool Gd, Vaisar T, Reardon CA, Getz GS. (2009) An apoA-I mimetic peptide containing a proline residue has greater in vivo HDL binding and anti-inflammatory ability than the 4F peptide. J Lipid Res. 50(9): 1889-1900.

Wu, G., Yuan, J., and Hunninghake, D.B. Effect of human apolipoprotein E isoforms on plasma lipids, lipoproteins and apolipoproteins in apolipoprotein E deficient mice. Atherosclerosis. 141:287-296 (1998).

Xia et al. (1999) High density lipoproteins (HDL) interrupt the sphingosine kinase signaling pathway. A possible mechanism for protection against atherosclerosis by HDL. JBiol Chem. 1999; 274:33143-33147.

Yamada, et al., Increased clearance of plasma cholesterol after injection of apolipoprotein E into Watanabe heritable hyperlipidemic rabbits. (1989) Proc. Natl. Acad. Sci. U.S.A. 86, 665-669.

Yamashita et al. (2000) Molecular mechanisms, lipoprotein abnormalities and atherogenicity of hyperalphalipoproteinemia. Atherosclerosis. 152:271-285.

Yan et al. (2004) PLTP deficiency improves the anti-inflammatory properties of HDL and reduces the ability of LDL to induce monocyte chemotactic activity. J Lipid Res 2004; 45:1852-1858.

Yancey et al. (1995) Efflux of Cellular Cholesterol and Phospholipid to Lipid-free Apolipoproteins and Class A Amphipathic Peptides. Biochemistry, 34: 7955-7965.

Yip KP, Marsh DJ. (1997) An Arg-Gly-Asp peptide stimulates constriction in rat afferent arteriole. Am J Physiol. 273(5 Pt 2): F768-F776.

Yla-Herttuala, S. et al. Macrophages and smooth muscle cells express lipoprotein lipase in human and rabbit atherosclerotic lesions. (1991) Proc. Natl. Acad. Sci. U.S.A. 88:10143-10147.

Yokoyama, et al. The mechanism of activation of lecithin:cholesterol acyltransferase by apolipoprotein A-I and an amphiphilic peptide. J. Biol. Chem. 255:7333-7339, 1980.

Yu et al. Tissue Doppler imaging is superior to strain rate imaging and postsystolic shortening on the prediction of reverse remodeling in both ischemic and nonischemic heart failure after cardiac resynchronization therapy. (2004) Circulation 110:III-243.

Yuan and Altman, Substrate recognition by human RNase P: identification of small, model substrates for the enzyme. EMBO J 14:159-168 (1995).

Yuan et al., Targeted cleavage of mRNA by human RNase P. Proc. Natl. Acad. Sci. USA 89:8006-8010 (1992).

Yui et al. (1988) Serum prostacyclin stabilizing factor is identical to apolipoprotein A-I (Apo A-I). A novel function of Apo A-1, J. Clin. Invest. 1988; 82: 803-807.

Zabner et al., Adenovirus-mediated gene transfer transiently corrects the chloride transport defect in nasal epithelia of patients with cystic fibrosis. Cell 75:207-216 (1993).

Zabner et al., Safety and efficacy of repetitive adenovirus-mediated transfer of CFTR cDNA to airway epithelia of primates and cotton rats. Nature Genetics 6:75-83 (1994).

Zaiou et al., Apolipoprotein E;-low density lipoprotein receptor interaction. Influences of basic residue and amphipathic alpha-helix organization in the ligand. Journal of Lipid Research 41: 1087-1095 (2000).

Zeiher at al. (1994) Coronary atherosclerotic wall thickening and vascular reactivity in humans. Elevated high-density lipoprotein levels ameliorate abnormal vasoconstriction in early atherosclerosis. Circulation 1994;89;2525-2532.

Zhang Z, et al. (2007) D-4F, an Apolipoprotein A-I Mimetic Peptide, Prevents Endothelial Dysfunction Induced by Myeloperoxidase-Derived Hypochlorous Acid. Meeting Abstract 21: 706.11, FASEB J.

Zhang, C., et al. L-arginine chlorination products inhibit endothelial nitric oxide production. J. Biol. Chem. 276: 27159-27165 (2001).

Zhang, Renliang et al (2002) Myeloperoxidase functions as a major enzymatic catalyst for initiation of lipid peroxidation at sites of inflammation. J Biol Chem 2002;277:46116-46122.

Zhang, S. H., et al., Spontaneous hypercholesterolemia and arterial lesions in mice lacking apolipoprotein E. Science, 1992, 258, 468-471.

Zhang, Wei-Jian et al. (2002) Lack of inhibitory effect of HDL on TNFalpha-induced adhesion molecule expression in human aortic endothelial cells. Atherosclerosis 2002; 165:241-249.

Zhao et al. (2002) Selective interleukin-12 synthesis defect in 12/15-lipoxygenase deficient macrophages associated with reduced atherosclerosis in a mouse model of familial hypercholesterolemia. J Biol Chem 2002; 277:35350-35356.

Zhu, B., Kubel, D.G., Witte, D.P., and Hui, D.Y. Apolipoprotein E inhibits neointimal hyperplasia after arterial injury in mice. Am. J. Pathol. 157:1839-48 (2000).

Zhu, Y., and Hui, D.Y. Apolipoprotein E binding to low density lipoprotein receptor related protein-1 inhibits cell migration via activation of cAMP dependent protein kinase A. J. Biol. Chem. 278:36257-63 (2003).

Zilversmit, D.E. (1979) Atherogenesis: a postprandial phenomenon.. Circulation 60:473-485.

Zuker, M. On finding all suboptimal foldings of an RNA molecule. Science 244:48-52, 1989.

Restriction Requirement issued Sep. 12, 2002 for U.S. Appl. No. 09/645,454.

Response to Restriction Requirement filed Dec. 12, 2002 for U.S. Appl. No. 09/645,454.

Non-Final Office Action issued Jan. 22, 2003, for U.S. Appl. No. 09/645,454.

Response to Non-Final Office Action filed May 27, 2003 for U.S. Appl. No. 09/645,454.

Notice of Allowance issued Jun. 25, 2003 for U.S. Appl. No. 09/645,454.

Restriction Requirement issued Feb. 20, 2003 for U.S. Appl. No. 09/896,841.

Response to Restriction Requirement filed Aug. 25, 2003 for U.S. Appl. No. 09/896,841.

Non-Final Office Action issued Oct. 21, 2003 for U.S. Appl. No. 09/896,841.

Response to Non-Final Office Action filed Apr. 23, 2004 for U.S. Appl. No. 09/896,841 .

Final Office Action issued May 7, 2004 for U.S. Appl. No. 09/896,841.

RCE/Response to Final Office Action filed Nov. 15, 2004 for U.S. Appl. No. 09/896,841.

Notice of Allowance issued Dec. 20, 2004 for U.S. Appl. No. 09/896,841.

International Search Report issued May 17, 2002 for PCT App. No. PCT/US01/26457.

International Preliminary Examination Report issued Mar. 4, 2003 for PCT App. No. PCT/US01/26457.

Restriction Requirement issued Jul. 15, 2003 for U.S. Appl. No. 10/187,215.

(56) References Cited

OTHER PUBLICATIONS

Response to Restriction Reqirement filed Nov. 19, 2003 for U.S. Appl. No. 10/187,215.
Non-Final Office Action issued Jan. 8, 2004 for U.S. Appl. No. 10/187,215.
Response to Non-Final Office Action filed Jul. 12, 2004 for U.S. Appl. No. 10/187,215.
Non-Final Office Action issued Aug. 26, 2004 for U.S. Appl. No. 10/187,215.
Response to Non-Final Office Action filed Feb. 28, 2005 for U.S. Appl. No. 10/187,215.
Final Office Action issued Apr. 11, 2005 for U.S. Appl. No. 10/187,215.
RCE/Response to Final Office Action filed Oct. 7, 2005 for U.S. Appl. No. 10/187,215.
Non-Final Office Action issued Oct. 28, 2005 for U.S. Appl. No. 10/187,215.
Response to Non-Final Office Action filed Mar. 20, 2006 for U.S. Appl. No. 10/187,215.
Notice of Allowance issued May 1, 2006 for U.S. Appl. No. 10/187,215.
Restriction Requirement issued Feb. 19, 2004 for U.S. Appl. No. 10/273,386.
Response to Restriction Requirement filed May 3, 2004 for U.S. Appl. No. 10/273,386.
Non-Final Office Action issued JUn. 21, 2004 for U.S. Appl. No. 10/273,386.
Response to Non-Final Office Action filed Dec. 21, 2004 for U.S. Appl. No. 10/273,386.
Final Office Action issued Feb. 2, 2005 for U.S. Appl. No. 10/273,386.
RCE/Response to Final Office Action filed Aug. 15, 2005 for U.S. Appl. No. 10/273,386.
Non-Final Office Action issued Sep. 7, 2005 for U.S. Appl. No. 10/273,386.
Response to Non-Final Office Action filed Jan. 20, 2006 for U.S. Appl. No. 10/273,386.
Final Office Action issued Mar. 31, 2006 for U.S. Appl. No. 10/273,386.
Response to Final Office Action filed Jul. 3, 2006 for U.S. Appl. No. 10/273,386.
Notice of Allowance issued Aug. 20, 2006 for U.S. Appl. No. 10/273,386.
Restriction Requirement issued Nov. 9, 2004 for U.S. Appl. No. 10/423,830.
Response to Restriction Requirement filed Mar. 1, 2005 for U.S. Appl. No. 10/423,830.
Non-Final Office Action issued Apr. 18, 2005 for U.S. Appl. No. 10/423,830.
Response to Non-Final Office Action filed Oct. 19, 2005 for U.S. Appl. No. 10/423,830.
Final Office Action issued Nov. 15, 2005 for U.S. Appl. No. 10/423,830.
RCE/Response to Final Office Action filed Oct. 18, 2006 for U.S. Appl. No. 10/423,830.
Notice of Allowance issued Nov. 21, 2006 for U.S. Appl. No. 10/423,830.
Restriction Requirement issued Aug. 21, 2007 for U.S. Appl. No. 11/407,390.
Response to Restriction Requirement filed Nov. 23, 2007 for U.S. Appl. No. 11/407,390.
Non-Final Office Action issued Jan. 17, 2008 for U.S. Appl. No. 11/407,390.
Response to Non-Final Office Action filed Jul. 17, 2008 for U.S. Appl. No. 11/407,390.
Final Office Action issued Sep. 11, 2008 for U.S. Appl. No. 11/407,390.
RCE/Response to Final Office Action filed Jul. 13, 2009 for U.S. Appl. No. 11/407,390.
Ex Parte Quayle Action issued Aug. 14, 2009 for U.S. Appl. No. 11/407,390.
Response to Ex Parte Quayle Action filed Oct. 14, 2009 for U.S. Appl. No. 11/407,390.
Notice of Allowance issued Dec. 2, 2009 for U.S. Appl. No. 11/407,390.
Restriction Requirement issued Aug. 12, 2010 for U.S. Appl. No. 12/027,728.
Response to Restriction Requirement filed Sep. 27, 2010 for U.S. Appl. No. 12/027,728.
Non-Final Rejection issued May 27, 2011 for U.S. App. No. 12/027,728.
Response to Non-Final Rejection filed Nov. 1, 2011 for U.S. Appl. No. 12/027,728.
International Search Report and Written Opinion issued Sep. 1, 2009 for PCT App. No. PCT/US2009/033415.
International Preliminary Opinion on Patentability issued Aug. 19, 2010 for PCT App. No. PCT/US2009/033415.
Preliminary Amendment filed Nov. 13, 2003 for U.S. Appl. No. 10/712,447.
Preliminary Amendment filed May 14, 2004 for U.S. Appl. No. 10/712,447.
Restriction Requirement issued Oct. 14, 2005 for U.S. Appl. No. 10/712,447.
Restriction Requirement issued Feb. 16, 2006 for U.S. Appl. No. 10/712,447.
Response to Restriction Requirement filed Apr. 16, 2006 for U.S. Appl. No. 10/712,447.
Non-Final Office Action issued May 31, 2006 for U.S. Appl. No. 10/712,447.
Response to Non-Final Office Action filed Nov. 29, 2006 for U.S. Appl. No. 10/712,447.
Final Office Action issued Mar. 2, 2007 for U.S. Appl. No. 10/712,447.
Response to Final Office Action filed Jul. 31, 2007 for U.S. Appl. No. 10/712,447.
Advisory Action issued Aug. 13, 2007 for U.S. Appl. No. 10/712,447.
Response to Advisory Action and Final Office Action filed Sep. 4, 2007 for U.S. Appl. No. 10/712,447.
Non-Final Office Action issued Nov. 19, 2007 for U.S. Appl. No. 10/712,447.
Response after Non-Final Office Action filed Mar. 12, 2008 for U.S. Appl. No. 10/712,447.
Non-Final Office Action issued Jun. 13, 2008 for U.S. Appl. No. 10/712,447.
Response to Non-Final Office Action filed Sep. 3, 2008 for U.S. Appl. No. 10/712,447.
Terminal Disclaimer filed Sep. 3, 2008 for U.S. Appl. No. 10/712,447.
Terminal Disclaimer accepted Feb. 12, 2009 for U.S. Appl. No. 10/712,447.
Notice of Allowance with Interview Summary and Examiner's Amendment issued Feb. 24, 2009 for U.S. Appl. No. 10/712,447.
Issue Notification issued Jul. 1, 2009 for U.S. Appl. No. 10/712,447.
Request for Certificate of Correction filed Aug. 8, 3, 2009 for U.S. Appl. No. 10/712,447.
Certificate of Correction issued Sep. 8, 2009 for U.S. Appl. No. 10/712,447.
Restriction Requirement issued Jun. 26, 2008 for U.S. Appl. No. 11/405,601.
Response to Restriction Requirement filed Jul. 25, 2008 for U.S. Appl. No. 11/405,601.
Miscellaneous Action issued Oct. 24, 2008 for U.S. Appl. No. 11/405,601.
Response to Restriction Requirement filed Mar. 17, 2009 for U.S. Appl. No. 11/405,601.
Non-Final Office Action issued Jun. 10, 2009 for U.S. Appl. No. 11/405,601.
Response to Non-Final Rejection filed Oct. 9, 2009 for U.S. Appl. No. 11/405,601.
Final Office Action issued Jan. 29, 2010 for U.S. Appl. No. 11/405,601.

(56) References Cited

OTHER PUBLICATIONS

Response to Final Office Action filed Sep. 28, 2010 for U.S. Appl. No. 11/405,601.
Notice of Allowance issued Sep. 9, 2011 for U.S. Appl. No. 11/405,601.
International Search Report issued Nov. 17, 2005 for PCT Application No. PCT/US2003/036268.
Examiner's First Report issued Apr. 30, 2008 for Australian Application No. 200390825.
First Statement of Proposed Amendments filed Sep. 18, 2008 for Australian Application No. 200390825.
Notice of Acceptance issued Oct. 14, 2008 for Australian Application No. 200390825.
Grant of Request for Leave to Amend issued Jul. 3, 2009 for Australian Application No. 200390825.
First Examination Report issued Sep. 18, 2007 for New Zealand Application No. 541504.
Response to Examination Report filed Jul. 16, 2008 for New Zealand Application No. 541504.
Examination Report issued for Aug. 5, 2008 New Zealand Application No. 541504.
Response to Examination Report filed Dec. 23, 2008 for New Zealand Application No. 541504.
Examination Report issued Jan. 22, 2009 for New Zealand Application No. 541504.
Response to Examination Report filed Mar. 18, 2009 for New Zealand Application No. 541504.
Examination Report and Notice of Acceptance of Completed Specification issued Apr. 7, 2009 for New Zealand Application No. 541504.
Letters Patent issued Aug. 13, 2009 for New Zealand Application No. 541504.
Office Action issued Aug. 10, 2009 for Canadian Application No. 2,514,303.
Response to Office Action filed Feb. 10, 2010 for Canadian Application No. 2,514,303.
Office Action issued Oct. 6, 2010 for Canadian Application No. 2,514,303.
Response to Office Action filed Mar. 29, 2011 for Canadian Application No. 2,514,303.
Preliminary Amendment filed Mar. 12, 2010 for U.S. Appl. No. 12/675,089.

* cited by examiner

LRLLRKLKRRDWLKAFYDKVEKLKEAF
Sc-hE-18A

FIGURE 9

| Gene | Fold increase | |
|---|---|---|
| | 5h | O/N |
| ABCA1 | 2.32 | 1.10 |
| LDLR | 1.88 | 1.42 |
| CD36 | 1.25 | 1.30 |
| PPARδ | 1.9 | 1.30 |

Turn over experiments in NZW rabbits fed 1% diet shows initial decreases in plasma cholesterol (_____) and the disappearance of peptide (-----) from plasma. Despite the loss of peptide from the plasma, effect of the peptide lasts for 14 days (see Fig.7 and 8)

FIGURE 18

| Effect on plasma cholesterol (mg/dl) | | |
|---|---|---|
| | 0 min | 6 weeks |
| Control | 455±10 | 454±16 |
| 18L-2Y | 514±8 | 520±24 |
| R18L-2Y | 539±12 | 471±20 |

Timeline of hE-4F, hE-Sc2F, L-4F administration to ZDF rats

Dose of Peptides: 5mg/Kg i.v.

A sequence that is scrambled as α-helix but is a perfect amphipathic π-helix

LRKLRKRLLRKAFEEVLAKKFYDKALWD

Sc-hE-18A plotted as either α helix or π helix does not show amphipathicity

LRLLRKLKRR-DWLKAFYDKVEKLKEAF

LRKLRKRLLRKAFEEVLAKKFYDKALWD
hE-Sc-18A

SEQUENCE LISTING

<160> NUMBER OF SEQ ID NOS: 104

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 1

Leu Arg Lys Leu Arg Lys Arg Leu Leu Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 2

```
Leu Arg Lys Met Arg Lys Arg Leu Met Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 3

Leu Arg Arg Leu Arg Arg Arg Leu Leu Arg
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 4

Asp Trp Leu Lys Ala Phe Tyr Asp Lys Val Ala Glu Lys Leu Lys Gly
1               5                   10                  15

Ala Phe

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 5

Leu Arg Lys Leu Arg Lys Arg Leu Leu Arg
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 6

Leu Arg Lys Leu Arg Lys Arg Leu Leu Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 7

Leu Arg Lys Met Arg Lys Arg Leu Met Arg
1               5                   10

<210> SEQ ID NO 8
<211> LENGTH: 10
<212> TYPE: PRT
<213> ORGANISM: Artificial Sequence
```

-continued

```
<220> FEATURE:
<223> OTHER INFORMATION: Description of Artificial Sequence:  note =
      Synthetic Construct

<400> SEQUENCE: 8

Leu Arg Lys Leu Pro Lys Arg Leu Leu Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 9

Leu Arg Asn Val Arg Lys Arg Leu Val Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 10

Met Arg Lys Leu Arg Lys Arg Val Leu Arg
1               5                   10

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 11

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 12

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct
```

```
<400> SEQUENCE: 13

Leu Arg Arg Leu Arg Arg Arg Leu Leu Arg Asp Trp Leu Lys Ala Phe
 1               5                  10                  15

Tyr Asp Lys Val Ala Glu Lys Leu Lys Glu Ala Phe
             20                  25

<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 14

Leu Arg Lys Met Arg Lys Arg Leu Met Arg Asp Trp Leu Lys Ala Phe
 1               5                  10                  15

Tyr Asp Lys Val Ala Glu Lys Leu Lys Glu Ala Phe
             20                  25

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 15

Leu Arg Lys Leu Arg Lys Arg Phe Phe Arg
 1               5                  10

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 16

Asp Trp Leu Lys Ala Phe Tyr Asp Lys Val Ala Glu Lys Leu Lys Glu
 1               5                  10                  15

Ala Phe

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 17

Asp Trp Phe Lys Ala Phe Tyr Asp Lys Val Ala Glu Lys Phe Lys Glu
 1               5                  10                  15

Ala Phe

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct
```

-continued

```
<400> SEQUENCE: 18

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 19

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 20

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 21

Leu Arg Lys Met Arg Lys Arg Leu Met Arg Asp Trp Leu Lys Ala Phe
1               5                   10                  15

Tyr Asp Lys Val Ala Glu Lys Leu Lys Glu Ala Phe
            20                  25

<210> SEQ ID NO 22
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 22

Leu Arg Lys Met Arg Lys Arg Leu Met Arg Asp Trp Leu Lys Ala Phe
1               5                   10                  15

Tyr Asp Lys Val Ala Glu Lys Leu Lys Glu Ala Phe
            20                  25

<210> SEQ ID NO 23
<211> LENGTH: 28
<212> TYPE: PRT
```

```
<213> ORGANISM: Artificial Sequence
<220> FEATURE:
<223> OTHER INFORMATION: Description of Artificial Sequence:  note =
      Synthetic Construct

<400> SEQUENCE: 23

Leu Arg Lys Leu Pro Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 24
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 24

Leu Arg Asn Val Arg Lys Arg Leu Val Arg Asp Trp Leu Lys Ala Phe
1               5                   10                  15

Tyr Asp Lys Val Ala Glu Lys Leu Lys Glu Ala Phe
            20                  25

<210> SEQ ID NO 25
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 25

Met Arg Lys Leu Arg Lys Arg Val Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 26
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 26

Leu Arg Arg Leu Arg Arg Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 27
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 27

Leu Arg Lys Leu Arg Lys Arg Phe Phe Arg Asp Trp Leu Lys Ala Phe
1               5                   10                  15

Tyr Asp Lys Val Ala Glu Lys Leu Lys Glu Ala Phe
            20                  25
```

```
<210> SEQ ID NO 28
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 28

Leu Arg Lys Leu Arg Lys Arg Leu Leu Arg Asp Trp Phe Lys Ala Phe
 1               5                  10                  15

Tyr Asp Lys Val Ala Glu Lys Phe Lys Glu Ala Phe
            20                  25

<210> SEQ ID NO 29
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 29

Leu Arg Lys Leu Arg Lys Arg Leu Leu Arg Asp Trp Phe Lys Ala Phe
 1               5                  10                  15

Tyr Asp Lys Val Ala Glu Lys Phe Lys Glu Ala Phe
            20                  25

<210> SEQ ID NO 30
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 30

Leu Arg Lys Leu Arg Lys Arg Leu Leu Arg Asp Trp Phe Lys Ala Phe
 1               5                  10                  15

Tyr Asp Lys Val Ala Glu Lys Phe Lys Glu Ala Phe
            20                  25

<210> SEQ ID NO 31
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 31

Leu Arg Lys Met Arg Lys Arg Leu Met Arg Asp Trp Phe Lys Ala Phe
 1               5                  10                  15

Tyr Asp Lys Val Ala Glu Lys Phe Lys Glu Ala Phe
            20                  25

<210> SEQ ID NO 32
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 32
```

```
Leu Arg Lys Met Arg Lys Arg Leu Met Arg Asp Trp Phe Lys Ala Phe
1               5                   10                  15

Tyr Asp Lys Val Ala Glu Lys Phe Lys Glu Ala Phe
            20                  25
```

<210> SEQ ID NO 33
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 33

```
Leu Arg Lys Leu Pro Lys Arg Leu Leu Arg Asp Trp Phe Lys Ala Phe
1               5                   10                  15

Tyr Asp Lys Val Ala Glu Lys Phe Lys Glu Ala Phe
            20                  25
```

<210> SEQ ID NO 34
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 34

```
Leu Arg Asn Val Arg Lys Arg Leu Val Arg Asp Trp Phe Lys Ala Phe
1               5                   10                  15

Tyr Asp Lys Val Ala Glu Lys Phe Lys Glu Ala Phe
            20                  25
```

<210> SEQ ID NO 35
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 35

```
Met Arg Lys Leu Arg Lys Arg Val Leu Arg Asp Trp Phe Lys Ala Phe
1               5                   10                  15

Tyr Asp Lys Val Ala Glu Lys Phe Lys Glu Ala Phe
            20                  25
```

<210> SEQ ID NO 36
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 36

```
Leu Arg Arg Leu Arg Arg Arg Leu Leu Arg Asp Trp Phe Lys Ala Phe
1               5                   10                  15

Tyr Asp Lys Val Ala Glu Lys Phe Lys Glu Ala Phe
            20                  25
```

<210> SEQ ID NO 37
<211> LENGTH: 28
<212> TYPE: PRT
<213> ORGANISM: Artificial Sequence
<220> FEATURE:

<223> OTHER INFORMATION: Description of Artificial Sequence: note =
      Synthetic Construct

<400> SEQUENCE: 37

Leu Arg Lys Leu Arg Lys Arg Phe Phe Arg Asp Trp Phe Lys Ala Phe
1               5                   10                  15

Tyr Asp Lys Val Ala Glu Lys Phe Lys Glu Ala Phe
            20                  25

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 38

Asp Trp Leu Lys Ala Phe Tyr Asp Lys Val Ala Glu Lys Leu Lys Glu
1               5                   10                  15

Ala Phe Leu Arg Lys Leu Arg Lys Arg Leu Leu Arg
            20                  25

<210> SEQ ID NO 39
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 39

Asp Trp Leu Lys Ala Phe Tyr Asp Lys Val Ala Glu Lys Leu Lys Glu
1               5                   10                  15

Ala Phe Leu Arg Lys Leu Arg Lys Arg Leu Leu Arg
            20                  25

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 40

Asp Trp Leu Lys Ala Phe Tyr Asp Lys Val Ala Glu Lys Leu Lys Glu
1               5                   10                  15

Ala Phe Leu Arg Lys Leu Arg Lys Arg Leu Leu Arg
            20                  25

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 41

Asp Trp Leu Lys Ala Phe Tyr Asp Lys Val Ala Glu Lys Leu Lys Glu
1               5                   10                  15

Ala Phe Leu Arg Lys Met Arg Lys Arg Leu Met Arg
            20                  25

```
<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 42

Asp Trp Leu Lys Ala Phe Tyr Asp Lys Val Ala Glu Lys Leu Lys Glu
1               5                   10                  15

Ala Phe Leu Arg Lys Met Arg Lys Arg Leu Met Arg
            20                  25

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 43

Asp Trp Leu Lys Ala Phe Tyr Asp Lys Val Ala Glu Lys Leu Lys Glu
1               5                   10                  15

Ala Phe Leu Arg Lys Leu Pro Lys Arg Leu Leu Arg
            20                  25

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 44

Asp Trp Leu Lys Ala Phe Tyr Asp Lys Val Ala Glu Lys Leu Lys Glu
1               5                   10                  15

Ala Phe Leu Arg Asn Val Arg Lys Arg Leu Val Arg
            20                  25

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 45

Asp Trp Leu Lys Ala Phe Tyr Asp Lys Val Ala Glu Lys Leu Lys Glu
1               5                   10                  15

Ala Phe Met Arg Lys Leu Arg Lys Arg Val Leu Arg
            20                  25

<210> SEQ ID NO 46
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 46

Asp Trp Leu Lys Ala Phe Tyr Asp Lys Val Ala Glu Lys Leu Lys Glu
1               5                   10                  15
```

Ala Phe Leu Arg Arg Leu Arg Arg Leu Leu Arg
            20                  25

<210> SEQ ID NO 47
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 47

Asp Trp Leu Lys Ala Phe Tyr Asp Lys Val Ala Glu Lys Leu Lys Glu
1               5                   10                  15

Ala Phe Leu Arg Lys Leu Arg Lys Arg Phe Phe Arg
            20                  25

<210> SEQ ID NO 48
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 48

Asp Trp Phe Lys Ala Phe Tyr Asp Lys Val Ala Glu Lys Phe Lys Glu
1               5                   10                  15

Ala Phe Leu Arg Lys Leu Arg Lys Arg Leu Leu Arg
            20                  25

<210> SEQ ID NO 49
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 49

Asp Trp Phe Lys Ala Phe Tyr Asp Lys Val Ala Glu Lys Phe Lys Glu
1               5                   10                  15

Ala Phe Leu Arg Lys Leu Arg Lys Arg Leu Leu Arg
            20                  25

<210> SEQ ID NO 50
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 50

Asp Trp Phe Lys Ala Phe Tyr Asp Lys Val Ala Glu Lys Phe Lys Glu
1               5                   10                  15

Ala Phe Leu Arg Lys Leu Arg Lys Arg Leu Leu Arg
            20                  25

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

```
<400> SEQUENCE: 51

Asp Trp Phe Lys Ala Phe Tyr Asp Lys Val Ala Glu Lys Phe Lys Glu
1               5                   10                  15

Ala Phe Leu Arg Lys Met Arg Lys Arg Leu Met Arg
            20                  25

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 52

Asp Trp Phe Lys Ala Phe Tyr Asp Lys Val Ala Glu Lys Phe Lys Glu
1               5                   10                  15

Ala Phe Leu Arg Lys Met Arg Lys Arg Leu Met Arg
            20                  25

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 53

Asp Trp Phe Lys Ala Phe Tyr Asp Lys Val Ala Glu Lys Phe Lys Glu
1               5                   10                  15

Ala Phe Leu Arg Lys Leu Pro Lys Arg Leu Leu Arg
            20                  25

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 54

Asp Trp Phe Lys Ala Phe Tyr Asp Lys Val Ala Glu Lys Phe Lys Glu
1               5                   10                  15

Ala Phe Leu Arg Asn Val Arg Lys Arg Leu Val Arg
            20                  25

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 55

Asp Trp Phe Lys Ala Phe Tyr Asp Lys Val Ala Glu Lys Phe Lys Glu
1               5                   10                  15

Ala Phe Met Arg Lys Leu Arg Lys Arg Val Leu Arg
            20                  25

<210> SEQ ID NO 56
<211> LENGTH: 28
```

```
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 56

Asp Trp Phe Lys Ala Phe Tyr Asp Lys Val Ala Glu Lys Phe Lys Glu
 1               5                  10                  15

Ala Phe Leu Arg Arg Leu Arg Arg Leu Leu Arg
             20                  25

<210> SEQ ID NO 57
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 57

Asp Trp Phe Lys Ala Phe Tyr Asp Lys Val Ala Glu Lys Phe Lys Glu
 1               5                  10                  15

Ala Phe Leu Arg Lys Leu Arg Lys Arg Phe Phe Arg
             20                  25

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 58

Leu Arg Leu Leu Arg Lys Leu Lys Arg Arg
 1               5                  10

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 59

Lys Ala Phe Glu Glu Val Leu Ala Lys Lys Phe Tyr Asp Lys Ala Leu
 1               5                  10                  15

Trp Asp

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 60

Leu Arg Lys Leu Arg Lys Arg Leu Leu Arg Lys Ala Phe Glu Glu Val
 1               5                  10                  15

Leu Ala Lys Lys Phe Tyr Asp Lys Ala Leu Trp Asp
             20                  25

<210> SEQ ID NO 61
```

```
<211> LENGTH: 27
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 61

Leu Arg Leu Leu Arg Lys Leu Lys Arg Arg Asp Trp Leu Lys Ala Phe
1               5                   10                  15

Tyr Asp Lys Val Glu Lys Leu Lys Glu Ala Phe
            20                  25

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 62

Gly Phe Arg Arg Phe Leu Gly Ser Trp Ala Arg Ile Tyr Arg Ala Phe
1               5                   10                  15

Val Gly

<210> SEQ ID NO 63
<211> LENGTH: 28
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 63

Leu Arg Lys Leu Arg Lys Arg Leu Leu Arg Asp Trp Phe Lys Ala Phe
1               5                   10                  15

Tyr Asp Lys Val Ala Glu Lys Phe Lys Glu Ala Phe
            20                  25

<210> SEQ ID NO 64
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 64

Arg Leu Leu Arg Lys Arg Leu Lys Arg Leu Asp Trp Leu Lys Ala Phe
1               5                   10                  15

Tyr Asp Lys Val Ala Glu Lys Leu Lys Glu Ala Phe
            20                  25

<210> SEQ ID NO 65
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 65

Arg Leu Leu Arg Lys Arg Leu Lys Arg Leu Asp Trp Leu Lys Ala Phe
1               5                   10                  15

Tyr Asp Lys Val Ala Glu Lys Leu Lys Glu Ala Phe
```

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 66

Arg Leu Leu Arg Lys Arg Leu Lys Arg Leu Asp Trp Leu Lys Ala Phe
1               5                   10                  15

Tyr Asp Lys Val Ala Glu Lys Leu Lys Glu Ala Phe
            20                  25

<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 67

Arg Met Leu Arg Lys Arg Met Lys Arg Leu Asp Trp Leu Lys Ala Phe
1               5                   10                  15

Tyr Asp Lys Val Ala Glu Lys Leu Lys Glu Ala Phe
            20                  25

<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 68

Arg Met Leu Arg Lys Arg Met Lys Arg Leu Asp Trp Leu Lys Ala Phe
1               5                   10                  15

Tyr Asp Lys Val Ala Glu Lys Leu Lys Glu Ala Phe
            20                  25

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 69

Arg Leu Leu Arg Lys Pro Leu Lys Arg Leu Asp Trp Leu Lys Ala Phe
1               5                   10                  15

Tyr Asp Lys Val Ala Glu Lys Leu Lys Glu Ala Phe
            20                  25

<210> SEQ ID NO 70
<211> LENGTH: 28
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 70

```
Arg Val Leu Arg Lys Arg Val Asn Arg Leu Asp Trp Leu Lys Ala Phe
1               5                   10                  15

Tyr Asp Lys Val Ala Glu Lys Leu Lys Glu Ala Phe
            20                  25

<210> SEQ ID NO 71
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 71

Arg Leu Val Arg Lys Arg Leu Lys Arg Met Asp Trp Leu Lys Ala Phe
1               5                   10                  15

Tyr Asp Lys Val Ala Glu Lys Leu Lys Glu Ala Phe
            20                  25

<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 72

Arg Leu Leu Arg Arg Arg Leu Arg Arg Leu Asp Trp Leu Lys Ala Phe
1               5                   10                  15

Tyr Asp Lys Val Ala Glu Lys Leu Lys Glu Ala Phe
            20                  25

<210> SEQ ID NO 73
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 73

Arg Phe Phe Arg Lys Arg Leu Lys Arg Leu Asp Trp Leu Lys Ala Phe
1               5                   10                  15

Tyr Asp Lys Val Ala Glu Lys Leu Lys Glu Ala Phe
            20                  25

<210> SEQ ID NO 74
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 74

Arg Leu Leu Arg Lys Arg Leu Lys Arg Leu Asp Trp Phe Lys Ala Phe
1               5                   10                  15

Tyr Asp Lys Val Ala Glu Lys Phe Lys Glu Ala Phe
            20                  25

<210> SEQ ID NO 75
<211> LENGTH: 28
<212> TYPE: PRT
<213> ORGANISM: Artificial Sequence
```

```
<220> FEATURE:
<223> OTHER INFORMATION: Description of Artificial Sequence:  note =
      Synthetic Construct

<400> SEQUENCE: 75

Arg Leu Leu Arg Lys Arg Leu Lys Arg Leu Asp Trp Phe Lys Ala Phe
1               5                   10                  15

Tyr Asp Lys Val Ala Glu Lys Phe Lys Glu Ala Phe
            20                  25

<210> SEQ ID NO 76
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 76

Arg Leu Leu Arg Lys Arg Leu Lys Arg Leu Asp Trp Phe Lys Ala Phe
1               5                   10                  15

Tyr Asp Lys Val Ala Glu Lys Phe Lys Glu Ala Phe
            20                  25

<210> SEQ ID NO 77
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 77

Arg Met Leu Arg Lys Arg Met Lys Arg Leu Asp Trp Phe Lys Ala Phe
1               5                   10                  15

Tyr Asp Lys Val Ala Glu Lys Phe Lys Glu Ala Phe
            20                  25

<210> SEQ ID NO 78
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 78

Arg Met Leu Arg Lys Arg Met Lys Arg Leu Asp Trp Phe Lys Ala Phe
1               5                   10                  15

Tyr Asp Lys Val Ala Glu Lys Phe Lys Glu Ala Phe
            20                  25

<210> SEQ ID NO 79
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 79

Arg Leu Leu Arg Lys Pro Leu Lys Arg Leu Asp Trp Phe Lys Ala Phe
1               5                   10                  15

Tyr Asp Lys Val Ala Glu Lys Phe Lys Glu Ala Phe
            20                  25
```

-continued

```
<210> SEQ ID NO 80
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 80

Arg Val Leu Arg Lys Arg Val Asn Arg Leu Asp Trp Phe Lys Ala Phe
  1               5                  10                  15

Tyr Asp Lys Val Ala Glu Lys Phe Lys Glu Ala Phe
             20                  25

<210> SEQ ID NO 81
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 81

Arg Leu Val Arg Lys Arg Leu Lys Arg Met Asp Trp Phe Lys Ala Phe
  1               5                  10                  15

Tyr Asp Lys Val Ala Glu Lys Phe Lys Glu Ala Phe
             20                  25

<210> SEQ ID NO 82
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 82

Arg Leu Leu Arg Arg Arg Leu Arg Arg Leu Asp Trp Phe Lys Ala Phe
  1               5                  10                  15

Tyr Asp Lys Val Ala Glu Lys Phe Lys Glu Ala Phe
             20                  25

<210> SEQ ID NO 83
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 83

Arg Phe Phe Arg Lys Arg Leu Lys Arg Leu Asp Trp Phe Lys Ala Phe
  1               5                  10                  15

Tyr Asp Lys Val Ala Glu Lys Phe Lys Glu Ala Phe
             20                  25

<210> SEQ ID NO 84
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 84

Leu Arg Lys Leu Arg Lys Arg Leu Leu Arg Phe Ala Glu Lys Leu Lys
```

-continued

```
                1               5                   10                  15
Glu Ala Val Lys Asp Tyr Phe Ala Lys Leu Trp Asp
            20                  25

<210> SEQ ID NO 85
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 85

Leu Arg Lys Leu Arg Lys Arg Leu Leu Arg Phe Ala Glu Lys Leu Lys
1               5                   10                  15

Glu Ala Val Lys Asp Tyr Phe Ala Lys Leu Trp Asp
            20                  25

<210> SEQ ID NO 86
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 86

Leu Arg Lys Leu Arg Lys Arg Leu Leu Arg Phe Ala Glu Lys Leu Lys
1               5                   10                  15

Glu Ala Val Lys Asp Tyr Phe Ala Lys Leu Trp Asp
            20                  25

<210> SEQ ID NO 87
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 87

Leu Arg Lys Met Arg Lys Arg Leu Met Arg Phe Ala Glu Lys Leu Lys
1               5                   10                  15

Glu Ala Val Lys Asp Tyr Phe Ala Lys Leu Trp Asp
            20                  25

<210> SEQ ID NO 88
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 88

Leu Arg Lys Met Arg Lys Arg Leu Met Arg Phe Ala Glu Lys Leu Lys
1               5                   10                  15

Glu Ala Val Lys Asp Tyr Phe Ala Lys Leu Trp Asp
            20                  25

<210> SEQ ID NO 89
<211> LENGTH: 28
<212> TYPE: PRT
<213> ORGANISM: Artificial Sequence
<220> FEATURE:
<223> OTHER INFORMATION: Description of Artificial Sequence:  note =
```

-continued

Synthetic Construct

<400> SEQUENCE: 89

Leu Arg Lys Leu Pro Lys Arg Leu Leu Arg Phe Ala Glu Lys Leu Lys
1               5                   10                  15

Glu Ala Val Lys Asp Tyr Phe Ala Lys Leu Trp Asp
            20                  25

<210> SEQ ID NO 90
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 90

Leu Arg Asn Val Arg Lys Arg Leu Val Arg Phe Ala Glu Lys Leu Lys
1               5                   10                  15

Glu Ala Val Lys Asp Tyr Phe Ala Lys Leu Trp Asp
            20                  25

<210> SEQ ID NO 91
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 91

Met Arg Lys Leu Arg Lys Arg Val Leu Arg Phe Ala Glu Lys Leu Lys
1               5                   10                  15

Glu Ala Val Lys Asp Tyr Phe Ala Lys Leu Trp Asp
            20                  25

<210> SEQ ID NO 92
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 92

Leu Arg Arg Leu Arg Arg Arg Leu Leu Arg Phe Ala Glu Lys Leu Lys
1               5                   10                  15

Glu Ala Val Lys Asp Tyr Phe Ala Lys Leu Trp Asp
            20                  25

<210> SEQ ID NO 93
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 93

Leu Arg Lys Leu Arg Lys Arg Phe Phe Arg Phe Ala Glu Lys Leu Lys
1               5                   10                  15

Glu Ala Val Lys Asp Tyr Phe Ala Lys Leu Trp Asp
            20                  25

<210> SEQ ID NO 94

<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 94

Leu Arg Lys Leu Arg Lys Arg Leu Leu Arg Phe Ala Glu Lys Phe Lys
1               5                   10                  15

Glu Ala Val Lys Asp Tyr Phe Ala Lys Phe Trp Asp
            20                  25

<210> SEQ ID NO 95
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 95

Leu Arg Lys Leu Arg Lys Arg Leu Leu Arg Phe Ala Glu Lys Phe Lys
1               5                   10                  15

Glu Ala Val Lys Asp Tyr Phe Ala Lys Phe Trp Asp
            20                  25

<210> SEQ ID NO 96
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 96

Leu Arg Lys Leu Arg Lys Arg Leu Leu Arg Phe Ala Glu Lys Phe Lys
1               5                   10                  15

Glu Ala Val Lys Asp Tyr Phe Ala Lys Phe Trp Asp
            20                  25

<210> SEQ ID NO 97
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 97

Leu Arg Lys Met Arg Lys Arg Leu Met Arg Phe Ala Glu Lys Phe Lys
1               5                   10                  15

Glu Ala Val Lys Asp Tyr Phe Ala Lys Phe Trp Asp
            20                  25

<210> SEQ ID NO 98
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 98

Leu Arg Lys Met Arg Lys Arg Leu Met Arg Phe Ala Glu Lys Phe Lys
1               5                   10                  15

```
Glu Ala Val Lys Asp Tyr Phe Ala Lys Phe Trp Asp
            20                  25

<210> SEQ ID NO 99
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 99

Leu Arg Lys Leu Pro Lys Arg Leu Leu Arg Phe Ala Glu Lys Phe Lys
1               5                   10                  15

Glu Ala Val Lys Asp Tyr Phe Ala Lys Phe Trp Asp
            20                  25

<210> SEQ ID NO 100
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 100

Leu Arg Asn Val Arg Lys Arg Leu Val Arg Phe Ala Glu Lys Phe Lys
1               5                   10                  15

Glu Ala Val Lys Asp Tyr Phe Ala Lys Phe Trp Asp
            20                  25

<210> SEQ ID NO 101
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 101

Met Arg Lys Leu Arg Lys Arg Val Leu Arg Phe Ala Glu Lys Phe Lys
1               5                   10                  15

Glu Ala Val Lys Asp Tyr Phe Ala Lys Phe Trp Asp
            20                  25

<210> SEQ ID NO 102
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 102

Leu Arg Arg Leu Arg Arg Arg Leu Leu Arg Phe Ala Glu Lys Phe Lys
1               5                   10                  15

Glu Ala Val Lys Asp Tyr Phe Ala Lys Phe Trp Asp
            20                  25

<210> SEQ ID NO 103
<211> LENGTH: 28
<212> TYPE: PRT
<213> ORGANISM: Artificial Sequence
<220> FEATURE:
<223> OTHER INFORMATION: Description of Artificial Sequence:  note =
      Synthetic Construct
```

-continued

```
<400> SEQUENCE: 103

Leu Arg Lys Leu Arg Lys Arg Phe Phe Arg Phe Ala Glu Lys Phe Lys
 1               5                  10                  15

Glu Ala Val Lys Asp Tyr Phe Ala Lys Phe Trp Asp
            20                  25

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 104

Arg Leu Thr Arg Lys Arg Gly Leu Lys
 1               5
```

SYNTHETIC APOLIPOPROTEIN E MIMICKING POLYPEPTIDES AND METHODS OF USE

CROSS-REFERENCE TO RELATED PATENT APPLICATIONS

The present application is a National Phase Application of International Application No. PCT/US2008/074485, filed Aug. 27, 2008, which claims priority to U.S. Provisional Application No. 60/968,355, titled Synthetic Apolipoprotein E Mimicking Polypeptides and Methods of Use, filed on Aug. 28, 2007, which is hereby incorporated herein by reference in its entirety.

STATEMENT REGARDING FEDERALLY SPONSORED RESEARCH

This invention is made with Government support under HL034343 and HL065663 awarded by National Institute of Health. The United States Government has certain rights to this invention.

FIELD OF THE INVENTION

This invention relates to the field of molecular biology and protein biology including polypeptides and polypeptide mimics This application also relates to the field of cholesterol metabolism, catabolism, and the treatment and management of cholesterol associated disorders. The present invention also relates generally to the field of cardiovascular medicine. More specifically, the present invention relates to synthetic peptides that can rapidly lower plasma cholesterol through enhanced LDL and VLDL uptake and degradation by cells. The present invention also relates to synthetic peptides that can improve HDL function and/or exert anti-inflammatory properties.

BACKGROUND OF THE INVENTION

Epidemiological studies indicate that increased plasma cholesterol levels increase the risk for atherosclerosis. Five completed major trials have provided conclusive evidence of a benefit from treatment aimed primarily at reducing low-density lipoprotein (LDL)-cholesterol (Illingworth R D., et al. *Current Opini. Lipidol.* 1999, 10:383-386). Among other lipoprotein risk factors is familial dysbetalipoproteinemia, which results in the accumulation of remnant atherogenic lipoproteins derived from the catabolism of chylomicron and VLDL (Kwiterovich, P. O., Jr. *Am. J. Cardiol.* 1998, 82:3U-7U). It has been shown that a 1% decrease in the plasma cholesterol level decreases the risk of coronary artery disease by 2% (Deedwania, P. C. *Med. Clin. North Am.* 1995, 79:973-998). The focus of angiographic trials has been on LDL reduction and these studies have demonstrated that decreases in LDL-cholesterol of more than 30% to 35% are associated with lower rates of coronary events (Watts, G. W., et al. *Atherosclerosis* 1998, 414:17-30). There is also growing evidence that triglyceride-rich lipoproteins may adversely affect endothelial function and increase oxidative stress by promoting the production of small, dense LDL and by reducing high-density lipoprotein (HDL) levels (Marais, D., *Curr. Opin. Lipidol.* 2000, 11:597-602).

Apolipoprotein E (apo E) plays an important role in the metabolism of triglyceride-rich lipoproteins, such as very low density lipoprotein (VLDL) and chylomicrons. Apolipoprotein E mediates the high affinity binding of apo E-containing lipoproteins to the low density lipoprotein (LDL) receptor (apo B, E receptor) and the members of its gene family, including LDL receptor related protein (LRP), very low density lipoprotein receptor (VLDLR) and the apoE2 receptor (apoE2R) (Mahley, R. W., (1988) Science 240, 622-630). The putative and complex role of apo E in atherosclerosis has been emphasized by several observations: (i) mice that overexpress human apo E have lower levels of total plasma cholesterol levels (Shimono, H. N., et al., (1992) Eur. J. Clin. Invest. 90, 2084-2991), (ii) intravenous injection of human apo E into cholesterol-fed rabbits protects these animals from atherosclerosis (Yamada, et al., (1989) Proc. Natl. Acad. Sci. U.S.A. 86, 665-669), and (iii) loss of the apo E gene in mice produces spontaneous atherosclerosis (Zhang, S. H., et al., (1992) Science 258, 468-471) which is ameliorated when macrophage-specific apo E expression is initiated in apo E-deficient mice (Spangenberg, J., et al., (1997) Biochem. Biophys. Acta 1349, 109-121).

Apolipoprotein E is a protein that binds lipid and has two major domains (Mahley, R. W., et al. J. Lipid Res. 1999, 40:622-630). The 22 kDa amino terminal domain has been shown by X-ray crystallographic studies to be a 4-helix bundle (Wilson, C., et al. Science 1991; 252:1817-1822) and to contain a positively-charged receptor binding domain. For this region to mediate very low-density lipoprotein (VLDL) binding to its receptors, the apolipoprotein must associate with the lipoprotein surface; this is enabled by the C-terminal amphipathic helical region. If the 4-helix bundle that contains the positively charged receptor-binding domain does not open up on the lipoprotein surface, then the VLDL is defective in binding to receptors. Thus, the positively charged arginine (Arg)-rich cluster domain of the Apo E and the C-terminal amphipathic helical domain, are both required for the enhanced uptake of atherogenic Apo E-containing lipoproteins.

Apo E is secreted as a 299 amino acid residue protein with a molecular weight of 34,200. Based on thrombin cleavage of apo E into two fragments, a two-domain hypothesis was initially suggested to explain the fact that the C-terminal region of apo E (192-299) is essential for its binding to hypertriglyceridemic VLDL and the N-terminal 22 kDa domain (1-191), binds to the LDL-R (Bradley, W. A., et al., (1986) J. Lipid Res. 27, 40-48). Additional physical-chemical characterization of the protein and its mutants have extended this concept and have shown that the region 192-211 binds to phospholipid while the amino terminal domain (1-191) is a globular structure that contains the LDL receptor binding domain in the 4-helix bundle (Wilson, C., et al., (1991) Science 252, 1817-1822). Studies with synthetic peptides (Sparrow et al.) and monoclonal antibodies pinpointed the LDL receptor binding domain of apo E between residues 129-169, a domain enriched in positively charged amino acids, Arg and Lys (Rall, S. C., Jr., et al., (1982) PNAS USA 79, 4696-4700; Lalazar, A., et al., (1988) J. Biol. Chem. 263, 3542-2545; Dyer, C. A., et al., (1991) J. Biol. Chem. 296, 22803-22806; and Dyer, C. A., et al., (1991) J. Biol. Chem. 266, 15009-15015).

Further studies with synthetic peptides were used to characterize the structural features of the domain of apo E that mediates its interaction with the LDL receptor (Dyer, C. A., et al., (1991) J. Biol. Chem. 296, 22803-22806; Dyer, C. A., et al., (1991) J. Biol. Chem. 266, 15009-15015; and Dyer, C. A., et al., (1995) J. Lipid Res. 36, 80-8). Residues 15. 141-155 of apo E, although containing the positively charged residues, did not compete for binding of LDL in a human skin fibroblast assay, but did so only as tandem covalent repeats [i.e. (141-155)₂]. N-acetylation of the (141-155)₂ peptide, on the other hand, enhanced LDL binding to fibroblasts (Nicoulin, I. R., et al., (1998) J. Clin Invest. 101, 223-234). The N-acetylated (141-155)₂ analog selectively associated with cholesterol-rich lipoproteins and mediated their acute clearance in vivo (Nicoulin, I. R., et al., (1998) J. Clin Invest. 101, 223-234). Furthermore, these studies indicated that the prerequisite for receptor binding is that the peptides be helical (Dyer, C. A., et al., (1995) J. Lipid Res. 36, 80-88). Enhanced LDL uptake and degradation were also observed (Mims, M. P., et al., (1994) J. Biol. Chem. 269, 20539-20647) using synthetic peptides modified to increase lipid association by N,N-distearyl derivation of glycine at the N-terminus of the native 129-169 sequence of Apo E (Mims, M. P., et al., (1994) J. Biol. Chem. 269, 20539-20647). Although LDL binding is mediated by the cationic sequence 141-155 of human Apo E, Braddock et al. (Braddock. D. T., et al., (1996) Biochemistry 35, 13975-13984) have shown that model peptides of the highly conserved anionic domain (41-60 of human Apo E) also modulate the binding and internalization of LDL to cell surface receptors. However, these peptides do not enhance LDL degradation.

Chylomicron is a lipoprotein found in blood plasma, which carries lipids from the intestines into other body tissues and is made up of a drop of triacylglycerols surrounded by a protein-phospholipid coating. Chylomicron remnants are taken up by the liver (Havel, R. J., 1985, Arteriosclerosis. 5:569-580) after sequestration in the space of Disse, which is enhanced in the presence of Apo E (Kwiterovich, P. O., Jr., 1998; Deedwania, P. C., 1995; and Watts, G. W., et al., 1998). Apo E is the major mediator of hepatic remnant lipoprotein uptake by the LDL receptor or LRP. Lipolysis of normal VLDL Sf (subfraction) of more than 60 permit binding of the lipolytic remnant to the LDL receptor (Catapano, A. L. et al., 1979, J. Biol. Chem. 254:1007-1009; Schonfield, G., et al. 1979. J. Clin. Invest. 64:1288-1297). Lipoprotein lipase (LpL) may facilitate uptake through localization of Apo B-containing lipoproteins to membrane heparan sulphate proteoglycan (HSPG) (Eisenberg, et al. 1992. J. Clin. Invest. 90:2013-2021; Hussain, M., et al., J. Biol. Chem. 2000, 275:29324-29330) and/or through binding to the LDL-receptor-related protein (LRP) (Beisiegel, U., et al., 1989, Nature 341:162-164). Cell-surface HSPG may also function as a receptor and has variable binding affinities for specific isoforms of Apo E. In particular, Apo E is synthesized by the liver and also by monocyte/macrophages, where it exerts its effect on cholesterol homeostasis. In vivo evidence for the local effect of lack of Apo E comes from the observations of Linton and Fazio, who showed accelerated atherosclerosis in C57BL/6 mice transplanted with bone marrow from Apo E-deficient mice (Linton, M. F. and Fazio, S. Curr. Openi. Lipidol. 1999, 10:97-105). Apo E-dependent LDL cholesteryl ester uptake pathway has been demonstrated in murine adrenocortical cells (Swarnakar, S., et al. J. Biol. Chem. 2001, 276:21121-21126). This appears to involve chondroitin sulphate proteoglycan (CSPG) and a 2-macroglobulin receptor.

It has been shown that the receptor-binding domain of Apo E, rich in Arg residues (141-150), covalently linked to a synthetic class A amphipathic-helical domain, enhances the hepatic atherogenic lipoprotein uptake (Datta, G., et al. Biochemistry 2000, 30:213-220). Recent studies indicate that a potential anti-atherogenic action of Apo E is that it stimulates endothelial production of heparan sulfate (HS) (Paka, L., et al. J. Biol. Chem. 1999, 274:4816-4823). Lipoproteins are complexes of one or more lipids bound to one or more proteins and transport water-insoluble fats in the blood. Cholesterol is carried through the bloodstream by lipoproteins. There are no agents available which reduce cholesterol via the binding mechanisms of lipoproteins. There is a need for more effective agents that are capable of reducing cholesterol in a subject so as to reduce diseases and conditions which are associated with increased cholesterol.

U.S. Pat. No. 6,506,880 denotes the first effort to synthesize apolipoprotein E-mimicking peptides based on the hypothesis that since lipid binding is essential for surface localization of the peptide on lipoproteins and for the receptor binding domain of apo E to be appropriately accessible to bind to the LDL receptor, joining a well-characterized, lipid-associating peptide such as the model class A amphipathic helix, 18A, to the 141-150 peptide sequence of apo E should be sufficient to confer biological activity. It was found that the peptides enhanced LDL/VLDL binding to a cell, increased LDL/VLDL degradation by a cell, lowered LDL/VLDL cholesterol in an in-need individual with atherosclerosis.

The present invention provides novel synthetic apolipoprotein E (ApoE)-mimicking peptides wherein the receptor binding domain of apolipoprotein E is covalently linked to 18A, the well characterized lipid-associating model class A amphipathic helical peptide as well as possible applications of the synthetic peptides in lowering human plasma LDL/VLDL cholesterol levels, thus inhibiting atherosclerosis. The present invention also provides possible applications of the synthetic peptides to improve HDL function and/or exert anti-inflammatory properties.

SUMMARY OF THE INVENTION

The present invention provides polypeptides, compositions and methods of use of said polypeptides and compositions. Disclosed herein are synthetic apolipoprotein E-mimicking peptides. For example, disclosed is a synthetic apolipoprotein E-mimicking peptide, consisting of a receptor binding domain of apolipoprotein E comprising the amino acid sequence of SEQ ID NO: 15; and a lipid-associating peptide, wherein said receptor binding domain is covalently linked to said lipid-associating peptide. The lipid-associating peptide of the disclosed synthetic apolipoprotein E-mimicking peptides can be model class A amphipathic helical peptide 18A. For example, the lipid-associating peptide can comprise the amino acid sequence of SEQ ID NO: 16 or SEQ ID NO: 17.

Also disclosed are synthetic apolipoprotein E-mimicking peptides, consisting of: a receptor binding domain of apolipoprotein E comprising the amino acid sequence of SEQ ID NO: 15; and a lipid-associating peptide, wherein said receptor binding domain is covalently linked to said lipid-associating peptide, wherein said synthetic peptide is protected using acetyl and amide groups at the N- and C-terminus, respectively. The disclosed synthetic apolipoprotein E-mimicking peptides can also be N-terminally protected with an acetyl group. The disclosed synthetic apolipoprotein E-mimicking peptides can also be C-terminally protected with an amide group.

Also disclosed herein are synthetic apolipoprotein E-mimicking peptides, comprising: a lipid binding domain of apolipoprotein E comprising the amino acid sequence of SEQ ID NO: 17; and a receptor binding domain peptide, wherein said lipid binding domain is covalently linked to said receptor binding domain peptide. The receptor binding domain peptide of such synthetic apolipoprotein E-mimicking peptides can be a human receptor binding domain peptide of ApoE. For example, receptor binding domain peptide of these synthetic apolipoprotein E-mimicking peptides can comprise the amino acid sequence of SEQ ID NOs: 1 or 15. The receptor binding domain peptide of these synthetic apolipoprotein E-mimicking peptides can also comprise the amino acid sequence of SEQ ID NOs: 2, 3, 5, 6, 7, 8, 9, or 10.

Also disclosed herein are synthetic apolipoprotein E-mimicking peptides, comprising: a lipid binding domain of apolipoprotein E comprising the amino acid sequence of SEQ ID NO: 17; and a receptor binding domain peptide, wherein said lipid binding domain is covalently linked to said receptor binding domain peptide, wherein said synthetic peptide is protected using acetyl and amide groups at the N- and C-terminal ends, respectively. Also disclosed are synthetic apolipoprotein E-mimicking peptides, wherein the synthetic apolipoprotein E-mimicking peptides can be from a species selected from the group consisting of human, mouse, rabbit, monkey, rat, bovine, pig and dog.

Also disclosed are synthetic apolipoprotein E-mimicking peptides, consisting of a combination of the disclosed receptor binding domains of apolipoprotein E and the disclosed lipid-associating peptides, wherein said receptor binding domain is covalently linked to said lipid-associating peptide in a reversed orientation. Also disclosed are synthetic apolipoprotein E-mimicking peptides, consisting of a combination of the disclosed receptor binding domains of apolipoprotein E and the disclosed lipid-associating peptides, wherein said receptor binding domain is covalently linked to said lipid-associating peptide in a domain switched orientation.

Also disclosed are synthetic apolipoprotein E-mimicking peptides, consisting of: a receptor binding domain of apolipoprotein E and a lipid-associating peptide, wherein said receptor binding domain is covalently linked to said lipid-associating peptide, wherein the receptor binding domain of apolipoprotein E is scrambled. Also disclosed are synthetic apolipoprotein E-mimicking peptides, consisting of a receptor binding domain of apolipoprotein E and a lipid-associating peptide, wherein said receptor binding domain is covalently linked to said lipid-associating peptide, wherein the lipid-associating peptide of apolipoprotein E is scrambled. Also disclosed are synthetic apolipoprotein E-mimicking peptides, consisting of: a receptor binding domain of apolipoprotein E and a lipid-associating peptide, wherein receptor binding domain is covalently linked to said lipid-associating peptide, wherein both the receptor binding domain of apolipoprotein E and the lipid-associating peptide of apolipoprotein E are scrambled.

Also disclosed are synthetic apolipoprotein E-mimicking peptides, consisting of: a receptor binding domain of apolipoprotein E and a lipid-associating peptide, wherein receptor binding domain is covalently linked to said lipid-associating peptide, wherein either the receptor binding domain of apolipoprotein E or the lipid-associating peptide of apolipoprotein E, or both are scrambled and the peptide is reverse-oriented. Also disclosed are pharmaceutical compositions comprising the disclosed synthetic apolipoprotein E-mimicking peptides and a pharmaceutically acceptable carrier. Also disclosed are isolated nucleic acids encoding the disclosed synthetic apolipoprotein E-mimicking peptides. For example, disclosed are isolated nucleic acid encoding the disclosed synthetic apolipoprotein E-mimicking peptides, wherein the nucleic acid comprises DNA, RNA and/or cDNA.

Also disclosed are vectors comprising isolated nucleic acids encoding the disclosed synthetic apolipoprotein E-mimicking peptides. Also disclosed are host cells comprising isolated nucleic acids encoding the disclosed synthetic apolipoprotein E-mimicking peptides. For example, disclosed are eukaryotic host cells and a prokaryotic host cells comprising isolated nucleic acids encoding the disclosed synthetic apolipoprotein E-mimicking peptides. Also disclosed are recombinant cells comprising isolated nucleic acids encoding the disclosed synthetic apolipoprotein E-mimicking peptides.

Also disclosed are recombinant cells producing the disclosed synthetic apolipoprotein E-mimicking peptides. Also disclosed are antibodies that bind the disclosed synthetic apolipoprotein E-mimicking peptides. Also disclosed are transgenic, non-human subjects comprising isolated nucleic acids encoding the disclosed synthetic apolipoprotein E-mimicking peptides. For example, disclosed a transgenic animal and plants comprising isolated nucleic acids encoding the disclosed synthetic apolipoprotein E-mimicking peptides.

Also disclosed are transgenic, non-human subjects expressing the disclosed synthetic apolipoprotein E-mimicking peptides. Also disclosed are methods for enhancing LDL binding to a cell, the method comprising contacting the cell with the disclosed synthetic apolipoprotein E-mimicking peptides. Also disclosed are methods comprising administering the disclosed synthetic apolipoprotein E-mimicking peptides to a subject, whereby plasma LDL, plasma VLDL, or both, are affected.

Also disclosed are methods comprising administering the disclosed synthetic apolipoprotein E-mimicking peptides to a subject, whereby plasma LDL, plasma VLDL, or both, are affected, wherein the synthetic apolipoprotein E-mimicking peptide is administered as a composition comprising the synthetic apolipoprotein E-mimicking peptide and a pharmaceutically acceptable carrier. Also disclosed are methods comprising administering the disclosed synthetic apolipoprotein E-mimicking peptides to a subject, whereby plasma LDL, plasma VLDL, or both, are affected, wherein binding of LDL to a cell of the subject is enhanced, degradation of LDL by a cell of the subject is increased, LDL cholesterol in the subject is lowered, binding of VLDL to a cell of the subject is enhanced, degradation of VLDL by a cell of the subject is increased, VLDL cholesterol in the subject is lowered, and/or total plasma concentration of cholesterol in the subject is lowered.

Also disclosed are methods comprising administering the disclosed synthetic apolipoprotein E-mimicking peptides to a subject, whereby plasma LDL, plasma VLDL, or both, are affected, wherein said synthetic apolipoprotein E-mimicking peptide is administered in an amount of about 0.01 mg/kg to about 5 mg/kg. Also disclosed are methods comprising administering the disclosed synthetic apolipoprotein E-mimicking peptides to a subject, whereby plasma LDL, plasma VLDL, or both, are affected, wherein the subject has coronary artery disease, rheumatoid arthritis, and/or systemic lupus.

Also disclosed are methods for treating a subject with a "Lipid Disorder", the method comprising administering to the subject an effective amount of the disclosed synthetic apolipoprotein E-mimicking peptides, or a composition thereof. Also disclosed are methods for treating a subject with a "Lipid Disorder", the method comprising administering to the subject an effective amount of the disclosed synthetic apolipoprotein E-mimicking peptides, or a composition thereof, wherein the synthetic apolipoprotein E-mimicking peptide is administered as a composition comprising the synthetic apolipoprotein E-mimicking peptide and a pharmaceutically acceptable carrier. Also disclosed are methods for treating a subject with a "Lipid Disorder", the method comprising administering to the subject an effective amount of the disclosed synthetic apolipoprotein E-mimicking peptides, or a composition thereof, wherein binding of LDL to a cell of the subject is enhanced, degradation of LDL by a cell of the subject is increased, LDL cholesterol in the subject is lowered, binding of VLDL to a cell of the subject is enhanced, degradation of VLDL by a cell of the subject is increased, VLDL cholesterol in the subject is lowered, and/or total plasma concentration of cholesterol in the subject is lowered.

Also disclosed are methods for treating a subject with a "Lipid Disorder", the method comprising administering to the subject an effective amount of the disclosed synthetic apolipoprotein E-mimicking peptides, or a composition thereof, wherein said synthetic apolipoprotein E-mimicking peptide is administered in an amount of about 0.01 mg/kg to about 5 mg/kg. Also disclosed are methods for treating a subject with a "Lipid Disorder", the method comprising administering to the subject an effective amount of the disclosed synthetic apolipoprotein E-mimicking peptides, or a composition thereof, wherein the subject has coronary artery disease, rheumatoid arthritis, and/or systemic lupus.

Also disclosed are methods for reducing serum cholesterol in a subject, the method comprising administering to the subject an effective amount of the disclosed synthetic apolipoprotein E-mimicking peptides, or a composition thereof. Also disclosed are methods for reducing serum cholesterol in a subject, the method comprising administering to the subject an effective amount of the disclosed synthetic apolipoprotein E-mimicking peptides, or a composition thereof, wherein the synthetic apolipoprotein E-mimicking peptide is administered as a composition comprising the synthetic apolipoprotein E-mimicking peptide and a pharmaceutically acceptable carrier.

Also disclosed are methods for reducing serum cholesterol in a subject, the method comprising administering to the subject an effective amount of the disclosed synthetic apolipoprotein E-mimicking peptides, or a composition thereof, wherein binding of LDL to a cell of the subject is enhanced, degradation of LDL by a cell of the subject is increased, LDL cholesterol in the subject is lowered, binding of VLDL to a cell of the subject is enhanced, degradation of VLDL by a cell of the subject is increased, VLDL cholesterol in the subject is lowered, and/or total plasma concentration of cholesterol in the subject is lowered.

Also disclosed are methods for reducing serum cholesterol in a subject, the method comprising administering to the subject an effective amount of the disclosed synthetic apolipoprotein E-mimicking peptides, or a composition thereof, wherein said synthetic apolipoprotein E-mimicking peptide is administered in an amount of about 0.01 mg/kg to about 5 mg/kg. Also disclosed are methods for reducing serum cholesterol in a subject, the method comprising administering to the subject an effective amount of the disclosed synthetic apolipoprotein E-mimicking peptides, or a composition thereof, wherein the subject has coronary artery disease, rheumatoid arthritis, and/or systemic lupus.

Also disclosed are methods for enhancing HDL function, the methods comprising contacting the cell with the disclosed synthetic apolipoprotein E-mimicking peptides. Also disclosed are methods for decreasing inflammation, the methods comprising contacting the cell with the disclosed synthetic apolipoprotein E-mimicking peptides, wherein the peptides remove the lipid hydro-peroxides from the plasma by increasing paraoxanase.

Also disclosed are methods for increasing plasma paraoxonase (PON-1) activity, the methods comprising contacting the cell with the disclosed synthetic apolipoprotein E-mimicking peptides. Also disclosed are methods for inhibiting atherogenesis, the methods comprising contacting the cell with the disclosed synthetic apolipoprotein E-mimicking peptides. Also disclosed are methods for inhibiting atherogenesis, the methods comprising contacting the cell with the disclosed synthetic apolipoprotein E-mimicking peptides, wherein plasma cholesterol levels are decreased and HDL functions are increased. Also disclosed are methods for removing atherogenic lipoproteins from vessel walls, the methods comprising contacting the cell with the disclosed synthetic apolipoprotein E-mimicking peptides. Also disclosed are methods for decreasing the atherogenicity of LDL, the methods comprising contacting the cell with the disclosed synthetic apolipoprotein E-mimicking peptides.

Also disclosed are methods comprising administering the disclosed synthetic apolipoprotein E-mimicking peptides to a subject, whereby plasma HDL is affected. Also disclosed are methods comprising administering the disclosed synthetic apolipoprotein E-mimicking peptides to a subject, whereby plasma HDL is affected, wherein the synthetic apolipoprotein E-mimicking peptide is administered as a composition comprising the synthetic apolipoprotein E-mimicking peptide and a pharmaceutically acceptable carrier. Also disclosed are methods comprising administering the disclosed synthetic apolipoprotein E-mimicking peptides to a subject, whereby plasma HDL is affected, wherein PON activity is increased, lipid hydroperoxides are cleared, atherogenic lipoproteins levels are reduced in the plasma, endothelial function is improved, and/or atherogenic lipoproteins are removed from the vessel wall.

Also disclosed are methods comprising administering the disclosed synthetic apolipoprotein E-mimicking peptides to a subject, whereby plasma HDL is affected, wherein the subject has Inflammatory Bowel Disease (IBD), systemic lupus erythematosus, Hashimoto's disease, rheumatoid arthritis, graft-versus-host disease, Sjögren's syndrome, pernicious anemia, Addison disease, Alzheimer's disease, scleroderma, Goodpasture's syndrome, ulcerative colitis, Crohn's disease, autoimmune hemolytic anemia, sterility, myasthenia gravis, multiple sclerosis, Basedow's disease, thrombopenia purpura, allergy; asthma, atopic disease, cardiomyopathy, glomerular nephritis, hypoplastic anemia, metabolic syndrome X Synthetic Apolipoprotein E Mimicking Polypeptides and Methods of Use, peripheral vascular disease, chronic obstructive pulmonary disease (COPD), emphysema, asthma, idiopathic pulmonary fibrosis, pulmonary fibrosis, adult respiratory distress syndrome, osteoporosis, Paget's disease, coronary calcification, polyarteritis nodosa, polymyalgia rheumatica, Wegener's granulomatosis, central nervous system vasculitis (CNSV), Sjogren's syndrome, scleroderma, polymyositis, AIDS inflammatory response, influenza, avian flu, viral pneumonia, endotoxic shock syndrome, sepsis, sepsis syndrome, trauma/wound, corneal ulcer, chronic/non-healing wound, reperfusion injury (prevent and/or treat), ischemic reperfusion injury (prevent and/or treat), spinal cord injuries (mitigating effects), cancers, myeloma/multiple myeloma, ovarian cancer, breast cancer, colon cancer, bone cancer, osteoarthritis, allergic rhinitis, cachexia, Alzheimer's disease, implanted prosthesis, biofilm formation, dermatitis, acute and chronic, eczema, psoriasis, contact dermatitis, erectile dysfunction, macular degeneration, nephropathy, neuropathy, Parkinson's Disease, peripheral vascular disease, and meningitis, cognition and rejection after organ transplantation.

Also disclosed are methods for treating a subject with an "Inflammatory Disorder", the method comprising administering to the subject an effective amount of the disclosed synthetic apolipoprotein E-mimicking peptides, or a composition thereof. Also disclosed are methods for treating a subject with an "Inflammatory Disorder", the methods comprising administering to the subject an effective amount of the disclosed synthetic apolipoprotein E-mimicking peptides, or a composition thereof, wherein the synthetic apolipoprotein E-mimicking peptide is administered as a composition comprising the synthetic apolipoprotein E-mimicking peptide and a pharmaceutically acceptable carrier. Also disclosed are synthetic apolipoprotein E-mimicking peptides consisting of: a receptor binding domain of apolipoprotein E and a lipid-associating peptide, wherein said receptor binding domain is covalently linked to said lipid-associating peptide in a domain switched orientation.

Also disclosed are synthetic apolipoprotein E-mimicking peptides consisting of: a receptor binding domain of apolipoprotein E and a lipid-associating peptide, wherein said receptor binding domain is covalently linked to said lipid-associating peptide, wherein the receptor binding domain of apolipoprotein E is in a reversed orientation Also disclosed are synthetic apolipoprotein E-mimicking peptides consisting of: a receptor binding domain of apolipoprotein E and a lipid-associating peptide, wherein said receptor binding domain is covalently linked to said lipid-associating peptide, wherein the lipid-associating peptide is in a reversed orientation.

Also disclosed are synthetic apolipoprotein E-mimicking peptides consisting of: a receptor binding domain of apolipoprotein E and a lipid-associating peptide, wherein said receptor binding domain is covalently linked to said lipid-associating peptide, wherein both the receptor binding domain of apolipoprotein E and the lipid-associating peptide are in a reversed orientation. Also disclosed are synthetic apolipoprotein E-mimicking peptides consisting of a receptor binding domain of apolipoprotein E. Also disclosed are synthetic apolipoprotein E-mimicking peptides consisting of a receptor binding domain of apolipoprotein E wherein the receptor binding domain is modified or altered.

Also disclosed are synthetic apolipoprotein E-mimicking peptides consisting of a receptor binding domain of apolipoprotein E wherein the receptor binding domain is mutated, scrambeled, and/or reverse-oriented. Also disclosed are synthetic apolipoprotein E-mimicking peptides consisting of a lipid-associating peptide. Also disclosed are synthetic apolipoprotein E-mimicking peptides consisting of a lipid-associating peptide wherein the lipid-associating peptide is modified or altered. Also disclosed are synthetic apolipoprotein E-mimicking peptides consisting of a lipid-associating peptide wherein the lipid-associating peptide is mutated, scrambeled, and/or reverse-oriented.

BRIEF DESCRIPTION OF THE DRAWINGS

The accompanying drawings, which are incorporated in and constitute a part of this specification, illustrate several embodiments of the invention and together with the description, serve to explain the principles of the invention. These are non-limiting examples.

FIG. 9 shows the effect of Ac-hE18A-NH$_2$ on mRNA levels in THP-1 derived macrophages.

FIG. 18 shows the effect of peptide R18L-2Y (1 mg/4 g of chow) administration on plasma cholesterol levels.

DETAILED DESCRIPTION OF THE INVENTION

Figure 1:
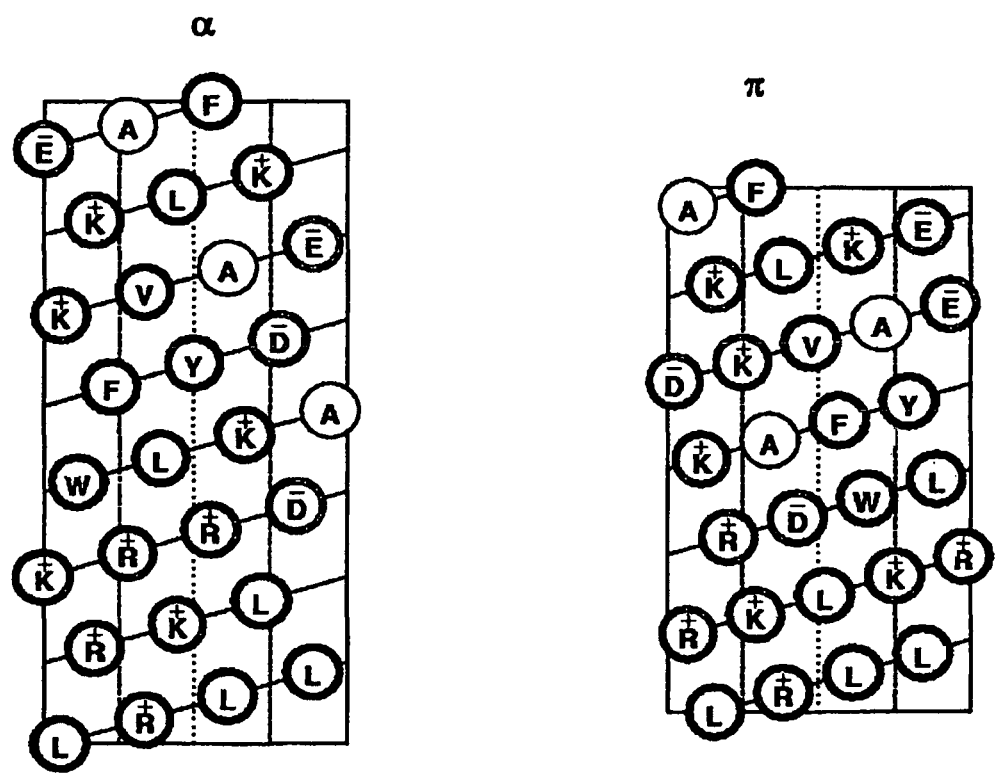
FIG. 1 shows a helical net representation of the difference between hE-18A and a scrambled form of hE-18A. As seen on the left side of the figure, the "α-amphipathic helix" has 3.6 amino acid residues per turn of the helix, whereas the "π-helix" has 4.4 amino acid residues per turn. The helical net does not show segregation of faces, thus the amphipathic helix nature is lost. Helical net is 2-dimensional representation of the helix cylinder when it is cut horizontally t the center of the cylinder and laid flat.

All patents, patent applications and publications cited herein, whether supra or infra, are hereby incorporated by reference in their entireties into this application in order to more fully describe the state of the art as known to those skilled therein as of the date of the invention described and claimed herein.

It is to be understood that this invention is not limited to specific synthetic methods, or to specific recombinant biotechnology methods unless otherwise specified, or to particular reagents unless otherwise specified, to specific pharmaceutical carriers, or to particular pharmaceutical formulations or administration regimens, as such may, of course, vary. It is also to be understood that the terminology used herein is for the purpose of describing particular embodiments only and is not intended to be limiting.

A. Definitions and Nomenclature

The terminology used herein is for the purpose of describing particular embodiments only and is not intended to be limiting.

As used in the specification and the appended claims, the singular forms "a," "an" and "the" can include plural referents unless the context clearly dictates otherwise. Thus, for example, reference to "a compound" includes mixtures of compounds, reference to "a pharmaceutical carrier" includes mixtures of two or more such carriers, and the like.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the term "amino acid sequence" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine;.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, yristolyation, oxidation, pergylation, proteolytic processing, phosphorylation, prenylation, racemization, selenoylation, sulfation, and transfer-RNA mediated addition of amino acids to protein such as arginylation. (See *Proteins-Structure and Molecular Properties* 2nd Ed., T. E. Creighton, W.H. Freeman and Company, New York (1993); *Posttranslational Covalent Modification of Proteins*, B. C. Johnson, Ed., Academic Press, New York, pp. 1-12 (1983)).

As used herein, "peptidomimetic" means a mimetic of a function of a protein which includes some alteration of the normal peptide chemistry. Peptidomimetics typically are short sequences of amino acids that in biological properties, mimic one or more function(s) of a particular protein. Peptide analogs enhance some property of the original peptide, such as increases stability, increased efficacy, enhanced delivery, increased half life, etc. Methods of making peptidomimetics based upon a known polypeptide sequence is described, for example, in U.S. Pat. Nos. 5,631,280; 5,612,895; and 5,579, 250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The word "or" as used herein means any one member of a particular list and also includes any combination of members of that list.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, "reverse oriented", "reversed orientation", "reverse analog" or "reverse sequence" refers to a peptide, or a portion of the peptide, has a reverse amino acid sequence as compared to a non-reverse oriented peptide (i.e., the original sequence is read (or written) from right to left). For example, if one peptide has the amino acid sequence ABCDE, its reverse analog or a peptide having its reverse sequence is as follows: EDCBA. In a dual domain peptide for example, Ac-hE-18A-NH$_2$, either the hE sequence is read from right to left or the 18A sequence is read from right to left. For a reverse analog of, LRKLRKRLLR-DWLKAFYDKVAEKLKEAF can be RLLRKRLKRL-DWLKAFYDKVAEKLKEAF (SEQ ID NO: 64) or LRKLRKRLLR-FAEKLKEAVKDY-FAKLWD (SEQ ID NO: 84).

As used herein a "dual-domain peptide", a "dual-domain synthetic peptide", or a "dual-domain ApoE mimicking peptide" is meant to mean a peptide comprising a lipid-associating peptide/domain and a receptor binding peptide/domain.

As used herein a "single-domain peptide", a "single-domain synthetic peptide", or a "single-domain ApoE mimicking peptide" is meant to mean a peptide comprising either a lipid-associating peptide/domain or a receptor binding peptide/domain, but not both.

As used herein "domain switched", "switched domain", or "switched" peptide is meant to mean that the lipid-associating peptide is covalently linked to the receptor binding domain of apolipoprotein E such that the lipid-associating peptide is at the N-terminus of the synthetic apolipoprotein E-mimicking peptide. For example, the peptide 18A-hE (SEQ ID NO: 38) is exemplary of a domain switched peptide.

Figure 21:
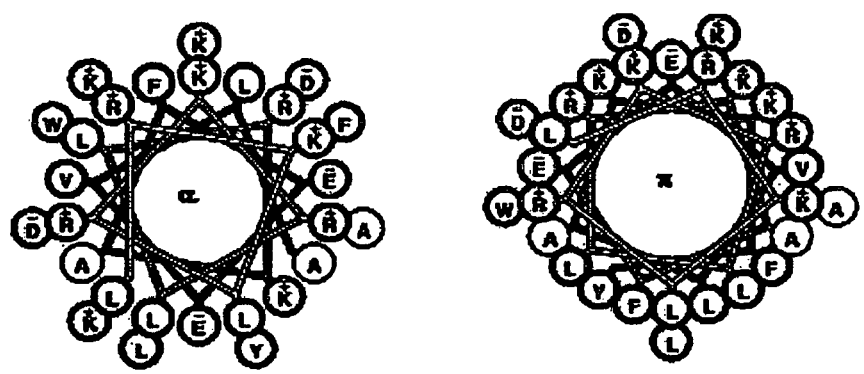
FIG. 21 shows a helical wheel representation of the peptide sequence 4F as a scrambled 4F peptide.
Figure 23:
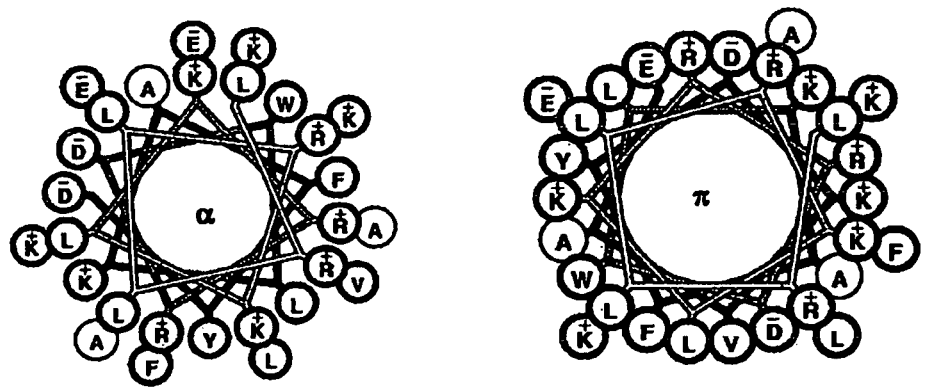
FIG. 23 shows Sc-hE-18A plotted as an α-helix or a π-helix. In the sequence Sc-hE-18A (LRLLRKLKRR-DWLKAFYDKVEKLKEAF), the hE-portion is scrambled. When this is scrambled, the sequence, when folded as alpha helix (3.6 residues/turn), the resulting alpha helix is not an amphipathic helix since there is no segregation of two (polar and nonpolar) faces. However, if it is folded as a pi-helix (4.4 residues/turn), the resulting structure also does not show segregation of polar and nonpolar faces.
Figure 24:
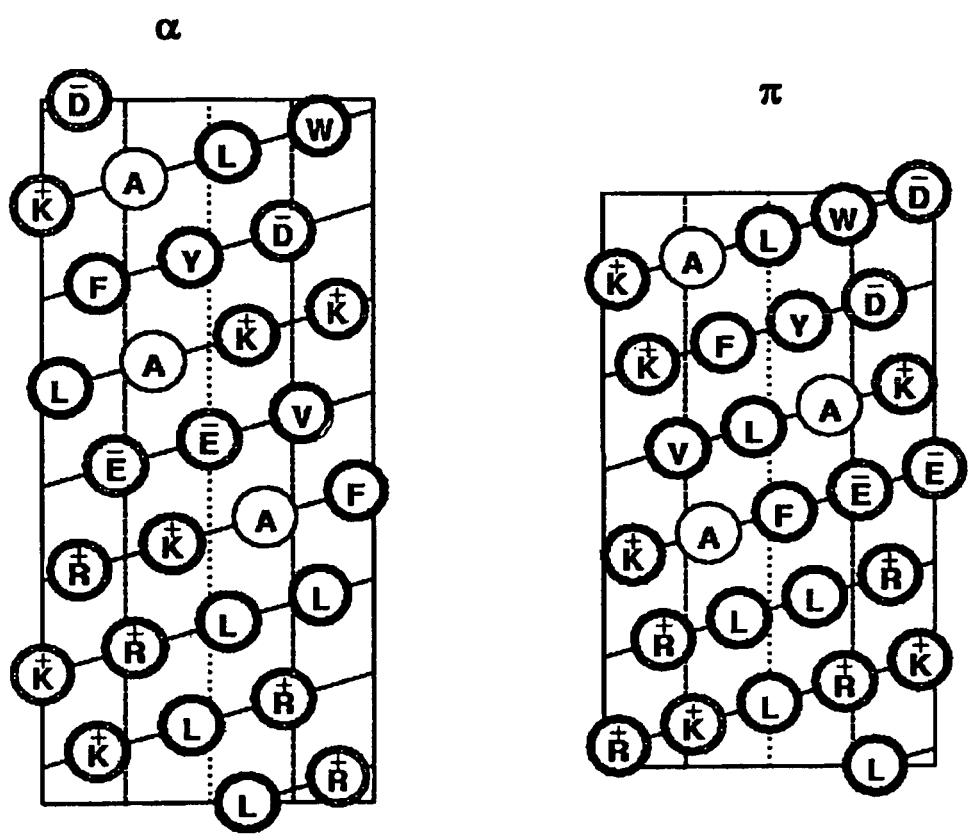
FIG. 24 shows a helical net representation of hE-Sc-18A. In this helical net program (that is, peptide sequence is folded a alpha or pi helix and spread on a plane) the alpha helix does not show segregation of popar and nonpolar faces whereas the pi-helix shows a clear nonpolar face at the center (black circles) and the polar residues blue and red circles appear at the edge. Peptides may associate with lipid as a pi-helix.

As used herein, "scrambled" "scrambled version", or "scrambled peptide" is meant to mean that the composition of the amino acid sequence is the same as the unscrambled peptide, however the sequence of the amino acids is altered thus rendering the peptide unable to form either an a-amphipathic helix or does not possess lipid associating (or HSPG associating) properties. However, in some cases, as described in this invention, the scrambled peptide remains able to form a different helical structure, such as a π-helix. For example, if one peptide has the amino acid sequence ABCDE, the scrambled version of the peptide could have the amino acid sequence DEABC. Scrambled peptides are often denoted as having an "Sc" prior to the portion of the peptide that is scrambled. For example, Sc-hE-18A denoted that the hE portion of the peptide is scrambled. FIGS. 21, 23 and 24 show examples of scrambled peptides.

An "α-amphipathic helix" is discussed above and has 3.6 amino acid residues per turn of the helix, whereas a "π-helix" has 4.4 amino acid residues per turn. For example FIGS. 1 and 24 show a difference between an "α-amphipathic helix" and a "π-helix".

As used herein, "sample" is meant to mean an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, "modulate" is meant to mean to alter, by increasing or decreasing.

As used herein "lipid binding domain E" and "lipid-associating peptide" are used interchangeably. As used herein, both terms can mean the lipid binding domain of Apolipoprotein E.

As used herein, "normal subject" is meant to mean an individual who does not have a "Lipid Disorder" or an "Inflammatory Disorder".

As used herein, "Lipid Disorder" is meant to mean when a subject has an excess of lipids or increased inflammatory lipids in their blood. Lipids include, but are not limited to cholesterol and triglycerides. Inflammatory lipids include, but are not limited to lipids such as ox-LDL related lipids (i.e., oxidized PAPC (1-palmitoyl 2-arachidonyl phosphatidyl choline). Oxidation of PAPC or PLPC, the lipid components of LDL, produce oxidized lipids. Having a lipid disorder can make you more likely to develop inflammatory diseases such as atherosclerosis and heart disease.

As used herein, "Inflammatory Disorder" is meant to mean when a subject experiences a cascade of reactions initiated by oxidized lipids in which several cytokine levels go up to alter the normal physiological response. Inflammatory disorders include, but are not limited to Inflammatory Bowel Disease (IBD), systemic lupus erythematosus, Hashimoto's disease, rheumatoid arthritis, graft-versus-host disease, Sjögren's syndrome, pernicious anemia, Addison disease, Alzheimer's disease, scleroderma, Goodpasture's syndrome, ulcerative colitis, Crohn's disease, autoimmune hemolytic anemia, sterility, myasthenia gravis, multiple sclerosis, Basedow's disease, thrombopenia purpura, allergy; asthma, atopic disease, arteriosclerosis, myocarditis, cardiomyopathy, glomerular nephritis, hypoplastic anemia, cognition and rejection after organ transplantation. Inflammatory diseases can be bacterial and/or viral in nature.

As used herein, "effective amount" of a compound is meant to mean a sufficient amount of the compound to provide the desired effect. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "effective amount." However, an appropriate "effective amount" may be determined by one of ordinary skill in the art using only routine experimentation.

As used herein, "isolated polypeptide" or "purified polypeptide" is meant to mean a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length proteins and/or polypeptides.

As used herein, "isolated nucleic acid" or "purified nucleic acid" is meant to mean DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

As used herein, "transgene" is meant to man a nucleic acid sequence that is inserted by artifice into a cell and becomes a part of the genome of that cell and its progeny. Such a transgene may be (but is not necessarily) partly or entirely heterologous (for example, derived from a different species) to the cell.

As used herein, "transgenic animal" is meant to mean an animal comprising a transgene as described above. Transgenic animals are made by techniques that are well known in the art.

As used herein, "knockout mutation" is meant to mean an alteration in the nucleic acid sequence that reduces the biological activity of the polypeptide normally encoded therefrom by at least 80% relative to the unmutated gene. The mutation may, without limitation, be an insertion, deletion, frameshift, or missense mutation. A "knockout animal," for example, a knockout mouse, is an animal containing a knockout mutation. The knockout animal may be heterozygous or homozygous for the knockout mutation. Such knockout animals are generated by techniques that are well known in the art.

As used herein, "treat" is meant to mean administer a compound or molecule of the invention to a subject, such as a human or other mammal (for example, an animal model), that has a Lipid Disorder, or that has coronary artery disease, rheumatoid arthritis, and/or systemic lupus, in order to prevent or delay a worsening of the effects of the disease or condition, or to partially or fully reverse the effects of the disease.

As used herein, "prevent" is meant to mean minimize the chance that a subject who has an increased susceptibility for developing a Lipid Disorder will develop a Lipid Disorder.

As used herein, "specifically binds" is meant that an antibody recognizes and physically interacts with its cognate antigen (for example, the disclosed synthetic apolipoprotein E-mimicking peptides) and does not significantly recognize and interact with other antigens; such an antibody may be a polyclonal antibody or a monoclonal antibody, which are generated by techniques that are well known in the art.

As used herein, "probe," "primer," or oligonucleotide is meant to mean a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for nucleic acids capable of encoding the disclosed synthetic apolipoprotein E-mimicking peptide (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the nucleic acid capable of encoding the disclosed synthetic apolipoprotein E-mimicking peptide to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP)

analysis, Southern hybridization, Northern hybridization, in situ hybridization, electrophoretic mobility shift assay (EMSA).

As used herein, "specifically hybridizes" is meant to mean that a probe, primer, or oligonucleotide recognizes and physically interacts (that is, base-pairs) with a substantially complementary nucleic acid (for example, a nucleic acid capable of encoding the disclosed synthetic apolipoprotein E-mimicking peptide) under high stringency conditions, and does not substantially base pair with other nucleic acids.

As used herein, "high stringency conditions" is meant to mean conditions that allow hybridization comparable with that resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1× Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, N.Y., 1998).

As used herein, "lipoprotein" or "lipoproteins" is meant to mean a biochemical assembly that contains both proteins and lipids. The lipids or their derivatives may be covalently or non-covalently bound to the proteins. Many enzymes, transporters, structural proteins, antigens, adhesins, and toxins are lipoproteins. Examples include the high density and low density lipoproteins of the blood, the transmembrane proteins of the mitochondrion and the chloroplast, and bacterial lipoproteins As used herein, "high-density lipoprotein" (HDL) is meant to mean a class of lipoproteins, varying somewhat in their size (8-11 nm in diameter), that can transport cholesterol.

As used herein, "very Low Density Lipoproteins" (VLDL) is meant to mean a lipoprotein subclass. It is assembled in the liver from cholesterol and apolipoproteins. It is converted in the bloodstream to low density lipoprotein (LDL). VLDL particles have a diameter of 30-80 nm. VLDL transports endogenous products where chylomicrons transport exogenous (dietary) products.

As used herein, "low-density lipoprotein" or "LDL" is mean to mean a lipoprotein that varies in size (approx. 22 nm) and can contain a changing number of fatty acids they actually have a mass and size distribution. Each native LDL particle contains a single apolipoproteinapolipoprotein B-100 molecule (Apo B-100, a protein with 4536 amino acidamino acid residues) that circles the fatty acids keeping them soluble in the aquous environment. LDL is commonly referred to as bad cholesterol Cholesterol cannot dissolve in the blood. It has to be transported to and from the cells by carriers called lipoproteins. LDLs and HDLs along with triglyceride-rich lipoproteins (VLDL) and Lp(a) cholesterol, make up your total cholesterol count, which can be determined through a blood test.

As used herein, "LDL cholesterol" is meant to mean cholesterol that is associated with LDLs. When too much LDL cholesterol circulates in the blood, it can slowly build up in the inner walls of the arteries that feed the heart and brain. Together with other substances, it can form plaque, a thick, hard deposit that can narrow the arteries and make them less flexible. This condition is known as atherosclerosis. If a clot forms and blocks a narrowed artery, then heart attack or stroke can result.

As used herein, "VLDL cholesterol" is meant to mean cholesterol that is associated with VLDLs.

As used herein, "HDL cholesterol" is meant to mean cholesterol that is associated with HDLs. About one-fourth to one-third of blood cholesterol is carried by high-density lipoprotein (HDL). HDL cholesterol is known as "good" cholesterol, because high levels of HDL seem to protect against heart attack. Low levels of HDL (less than 40 mg/dL in men and less than 50 mg/dL in women) also increase the risk of heart disease. Medical experts think that HDL tends to carry cholesterol away from the arteries and back to the liver, where it is passed from the body. Some experts believe that that HDL removes excess cholesterol from arterial plaque, thus slowing its buildup.

As used herein, "Lp(a)" is meant to mean a genetic variation of LDL (bad) cholesterol. A high level of Lp(a) is a significant risk factor for the premature development of fatty deposits in arteries. Lp(a) is not fully understood, but it may interact with substances found in artery walls and contribute to the buildup of fatty deposits.

B. Compounds and Compositions of the Invention

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein.

Peptides

Human apolipoprotein E (apo E) consists of two distinct domains, the lipid-associating domain (residues 192-299) and the globular domain (1-191) which contains the LDL receptor binding site (residues 129-169). To test the hypothesis that a minimal arginine-rich apoE receptor binding domain (141-150) was sufficient to enhance low density lipoprotein (LDL) and very low density lipoprotein (VLDL) uptake and clearance when covalently linked to a class A amphipathic helix, Anantharamaiah et al. synthesized a peptide in which the receptor binding domain of human apo E, LRKLRKRLLR (hApo E[141-150] also referred to as "hE", SEQ ID NO: 1), was linked to 18A, a well characterized high affinity lipid-associating peptide (DWLKAFYDKVAEK-LKEAF, also referred to as "18A", SEQ ID NO: 4) to produce a peptide denoted as hApoE[141-150]-18A (also referred to as "hE-18A", SEQ ID NO: 11) (see U.S. Pat. No. 6,506,880, which is hereby incorporated by reference in its entirety for its teaching of specific apolipoprotein E-mimicking peptides and their uses). Also synthesiszed was an end protected analog of hE-18A, denoted Ac-hE18A-$NH_2$(SEQ ID NO: 12). The importance of the lysine residues and the role of the hydrophobic residues in the receptor binding domain were also studied using two analogs, LRRLRRRLLR-18A (also referred to as "hE(R)-18A", SEQ ID NO: 13) and LRKM-RKRLMR-18A (also referred to as "mE18A", SEQ ID NO: 14), whereby the receptor binding domain of human apo E was modified to substitute arginine (R) residues for lysine (K) residues at positions 143 and 146 (SEQ ID NO: 3) and whereby the receptor binding domain of mouse apo E (SEQ ID NO: 2), were linked to 18A, respectively. The effect of the dual character peptides on the uptake and degradation of human LDL/VLDL by cells was then determined.

It was determined that in MEF 1 cells with induced LDL receptors, LDL internalization was enhanced three, five and seven times by Ac-mE-18A-$NH_2$, Ac-hE-18A-$NH_2$, and Ac-hE(R)-18A-$NH_2$ respectively. All three peptides increased degradation of LDL by 100 percent. Both Ac-hE-18A-NH$_2$ and the control peptide Ac-18A-NH$_2$ interacted with VLDL to cause a displacement of apo E from VLDL. However, only Ac-hE-18A-NH$_2$-associated VLDL enhanced the uptake of VLDL six fold and degradation three fold compared to VLDL alone in spite of the absence of apo E. The LDL binding to fibroblasts in the presence of these peptides was not saturable, however, over the LDL concentration range studied.

Furthermore, Anantharamaiah et al. showed a similar enhancement of LDL internalization independent of the presence of the LDL receptor related protein (LRP) or LDL receptor or both. Pretreatment of cells with heparinase and heparitinase however abolished greater than 80% of enhanced peptide-mediated LDL uptake and degradation by cells. The data indicated that the dual-domain peptides enhanced LDL uptake and degradation by binding to the LDL through the amphipathic lipid binding domain (18A). However, the minimal 141-150 Arg-rich domain did not decrease LDL levels but did so only in combination with 18A lipid associating domain, did not confer LDL-receptor binding but directed the LDL-peptide complex to the HSPG pathway for uptake and degradation by fibroblasts.

Non-limiting Examples of Polypeptides and Peptides of the Invention

The present invention is directed to a synthetic apolipoprotein-E mimicking peptide or polypeptide. Non-limiting examples of the synthetic apolipoprotein-E mimicking peptides or polypeptides of the invention are given below. Disclosed herein are synthetic apolipoprotein E-mimicking peptides, consisting of a receptor binding domain of apolipoprotein E comprising the amino acid sequence of SEQ ID NO: 15; and a lipid-associating peptide, wherein said receptor binding domain is covalently linked to said lipid-associating peptide. As such, the receptor binding domain replaced the two leucine (L) residues at positions 148 and 149 of LRKLRKRLLR (hApo E[141-150], SEQ ID NO: 1) with two phenylalanine (F) residues. The lipid associating peptide for these synthetic apolipoprotein E-mimicking peptides can be the model class A amphipathic helical peptide 18A. For example the lipid-associating peptide can comprise the amino acid sequence of SEQ ID NO: 16 or SEQ ID NO: 17.

Also disclosed herein are synthetic apolipoprotein E-mimicking peptides, comprising: a lipid binding domain of apolipoprotein E comprising the amino acid sequence of SEQ ID NO: 17; and a receptor binding domain peptide, wherein said lipid binding domain is covalently linked to said receptor binding domain peptide. As such, the lipid binding domain replaced the two leucine (L) residues of DWLKAFYDKVAEKLKEAF (18A, SEQ ID NO: 16) with two phenylalanine (F) residues resulting in the sequence DWFKAFYDKVAEKFKEAF (SEQ ID NO: 17, also referred to as modified 18A or m18A). The receptor binding domain peptide for the synthetic apolipoprotein E-mimicking peptides can be a human receptor binding domain peptide of ApoE. For example, receptor binding domain peptide of the disclosed synthetic apolipoprotein E-mimicking peptides can comprise the amino acid sequence of SEQ ID NO: 1, SEQ ID NO: 3, or SEQ ID NO: 15. The receptor binding domain peptide of such synthetic apolipoprotein E-mimicking peptides can also be from a species selected from the group consisting of mouse, rabbit, monkey, rat, bovine, pig and dog.

The receptor binding domain peptide for the synthetic apolipoprotein E-mimicking peptides can also be the LDL receptor (LDLR) binding domain of apolipoprotein B (ApoB). The LDL receptor (LDLR) binding domain of ApoB can have the sequence RLTRKRGLK (SEQ ID NO: 104). ApoB-100 is a 550,000 Da glycoprotein with nine amino acids (3359-3367) serving as the binding domain for the LDL receptor (Segrest et al., J. Lipid. Res. 42, pp. 1346-1367 (2001)). Upon binding to LDLR in clathrin coated pits, LDL is internalized via endocytosis and moves into the endosome where a drop in pH causes the receptor to dissociate from the LDL. The receptor is recycled back to the surface of the cell while the LDL is moved into the lysosome where the particle is degraded (Goldstein et al., Ann. Rev. Cell Biol. 1, pp. 1-39 (1985)). The LDL receptor (LDLR) binding domain of ApoB when used with the disclosed peptides can also be altered and/or modified as described throughout this application for ApoE. For example, LDL receptor (LDLR) binding domain of ApoB can be used with the the disclosed lipid-associating peptides, wherein the LDL receptor (LDLR) binding domain of ApoB is covalently linked to said lipid-associating peptide. In addition, the LDL receptor (LDLR) binding domain of ApoB can be scrambled, reverse-oriented, can be part of a domain switched peptide as described below.

Examples of receptor binding domain peptides that can be used in the disclosed synthetic apolipoprotein E-mimicking peptides are provided in Table 1.

TABLE 1

Disclosed Synthetic Apolipoprotein E-Mimicking Peptides

| Species | Starting Residue NO: | Sequence | SEQ ID NO: |
|---|---|---|---|
| Human | 141 | LRKLRKRLLR | SEQ ID NO: 1 |
| Rabbit | 134 | LRKLRKRLLR | SEQ ID NO: 5 |
| Monkey | 141 | LRKLRKRLLR | SEQ ID NO: 6 |
| Mouse | 133 | LRKMRKRLMR | SEQ ID NO: 2 |
| Rat | 133 | LRKMRKRLMR | SEQ ID NO: 7 |
| Bovine | 140 | LRKL*P*KRLLR | SEQ ID NO: 8 |
| Pig | 140 | LR*N*VRKRLVR | SEQ ID NO: 9 |
| Dog | 133 | MRKLRKRVLR | SEQ ID NO: 10 |
| R Modified | 141 | LR*R*LR*R*RLLR | SEQ ID NO: 3 |
| F Modified | 141 | LRKLRKR*FF*R | SEQ ID NO: 15 |
| ApoB | | *RLTRKRGLK* | SEQ ID NO: 104 |

The italicized residues in Table 1 indicate changes from the human sequence; however, the property of the amino acid is conserved. The bold-italicized residues in Table 1 indicate the difference from the human sequence at that position.

Also disclosed are synthetic apolipoprotein E-mimicking peptides, consisting of a combination of the disclosed receptor binding domains of apolipoprotein E and the disclosed lipid-associating peptides, wherein said receptor binding domain is covalently linked to said lipid-associating peptide. Additional lipid-associating peptides that can be used in the disclosed compositions are described in U.S. patent application Ser. No. 11/407,390 (Fogelman et al.), which is hereby incorporated by reference in its entirety for its teaching of lipid-associating peptides. For example, the lipid-associating peptides of Tables 2-6 of U.S. patent application Ser. No. 11/407,390 can be used in the disclosed compositions.

Also disclosed are synthetic apolipoprotein E-mimicking peptides, consisting of a combination of the disclosed receptor binding domains of apolipoprotein B and the disclosed lipid-associating peptides, wherein said receptor binding domain is covalently linked to said lipid-associating peptide. Non-limiting examples of the disclosed synthetic apolipoprotein E-mimicking peptides are provided in Table 2. The disclosed synthetic apolipoprotein E-mimicking peptides can also be N-terminally protected using acetyl and amino groups.

TABLE 2

Non-limiting Examples of the Disclosed Synthetic Apolipoprotein E-Mimicking Peptides

| Receptor Binding Domains of ApoE | Lipid-Associating Peptides | SEQ ID NO: |
|---|---|---|
| LRKLRKRLLR | DWLKAFYDKVAEKLKEAF | SEQ ID NO: 18 |
| LRKLRKRLLR | DWLKAFYDKVAEKLKEAF | SEQ ID NO: 19 |
| LRKLRKRLLR | DWLKAFYDKVAEKLKEAF | SEQ ID NO: 20 |
| LRKMRKRLMR | DWLKAFYDKVAEKLKEAF | SEQ ID NO: 21 |
| LRKMRKRLMR | DWLKAFYDKVAEKLKEAF | SEQ ID NO: 22 |
| LRKL$^P$KRLLR | DWLKAFYDKVAEKLKEAF | SEQ ID NO: 23 |
| LR$^N$VRKRLVR | DWLKAFYDKVAEKLKEAF | SEQ ID NO: 24 |
| MRKLRKRVLR | DWLKAFYDKVAEKLKEAF | SEQ ID NO: 25 |
| LRRLRRRLLR | DWLKAFYDKVAEKLKEAF | SEQ ID NO: 26 |
| LRKLRKR$^{FF}$R | DWLKAFYDKVAEKLKEAF | SEQ ID NO: 27 |
| LRKLRKRLLR | DWFKAFYDKVAEKFKEAF | SEQ ID NO: 28 |
| LRKLRKRLLR | DWFKAFYDKVAEKFKEAF | SEQ ID NO: 29 |
| LRKLRKRLLR | DWFKAFYDKVAEKFKEAF | SEQ ID NO: 30 |
| LRKMRKRLMR | DWFKAFYDKVAEKFKEAF | SEQ ID NO: 31 |
| LRKMRKRLMR | DWFKAFYDKVAEKFKEAF | SEQ ID NO: 32 |
| LRKL$^P$KRLLR | DWFKAFYDKVAEKFKEAF | SEQ ID NO: 33 |
| LR$^N$VRKRLVR | DWFKAFYDKVAEKFKEAF | SEQ ID NO: 34 |
| MRKLRKRVLR | DWFKAFYDKVAEKFKEAF | SEQ ID NO: 35 |
| LRRLRRRLLR | DWFKAFYDKVAEKFKEAF | SEQ ID NO: 36 |
| LRKLRKR$^{FF}$R | DWFKAFYDKVAEKFKEAF | SEQ ID NO: 37 |

Also disclosed are synthetic apolipoprotein E-mimicking peptides, consisting of a combination of the disclosed receptor binding domains of apolipoprotein E and the disclosed lipid-associating peptides, wherein said receptor binding domain is covalently linked to said lipid-associating peptide in a domain switched orientation. Also disclosed are synthetic apolipoprotein E-mimicking peptides, consisting of a combination of the disclosed receptor binding domains of apolipoprotein B and the disclosed lipid-associating peptides, wherein said receptor binding domain is covalently linked to said lipid-associating peptide in a domain switched orientation. These peptides can be referred to as "domain switched" "switched domain", or "switched" peptides. For example, disclosed are synthetic apolipoprotein E-mimicking peptides, consisting of a combination of the disclosed receptor binding domains of apolipoprotein E and the disclosed lipid-associating peptides, wherein said receptor binding domain is covalently linked to said lipid-associating peptide in a domain switched orientation to those described above and in Table 2. Specifically, the lipid-associating peptide is covalently linked to the receptor binding domain of apolipoprotein E such that the lipid-associating peptide is at the N-terminus of the synthetic apolipoprotein E-mimicking peptide. Non-limiting examples of the disclosed synthetic apolipoprotein E-mimicking peptides are provided in Table 3.

TABLE 3

Non-limiting Examples of Disclosed Synthetic Apolipoprotein E-Mimicking Peptides

| Lipid-Associating Peptides | Receptor Binding Domains of ApoE | SEQ ID NO: |
|---|---|---|
| DWLKAFYDKVAEKLKEAF | LRKLRKRLLR | SEQ ID NO: 38 |
| DWLKAFYDKVAEKLKEAF | LRKLRKRLLR | SEQ ID NO: 39 |
| DWLKAFYDKVAEKLKEAF | LRKLRKRLLR | SEQ ID NO: 40 |
| DWLKAFYDKVAEKLKEAF | LRKMRKRLMR | SEQ ID NO: 41 |
| DWLKAFYDKVAEKLKEAF | LRKMRKRLMR | SEQ ID NO: 42 |
| DWLKAFYDKVAEKLKEAF | LRKL$^P$KRLLR | SEQ ID NO: 43 |
| DWLKAFYDKVAEKLKEAF | LR$^N$VRKRLVR | SEQ ID NO: 44 |
| DWLKAFYDKVAEKLKEAF | MRKLRKRVLR | SEQ ID NO: 45 |
| DWLKAFYDKVAEKLKEAF | LRRLRRRLLR | SEQ ID NO: 46 |
| DWLKAFYDKVAEKLKEAF | LRKLRKR$^{FF}$R | SEQ ID NO: 47 |
| DWFKAFYDKVAEKFKEAF | LRKLRKRLLR | SEQ ID NO: 48 |
| DWFKAFYDKVAEKFKEAF | LRKLRKRLLR | SEQ ID NO: 49 |
| DWFKAFYDKVAEKFKEAF | LRKLRKRLLR | SEQ ID NO: 50 |
| DWFKAFYDKVAEKFKEAF | LRKMRKRLMR | SEQ ID NO: 51 |
| DWFKAFYDKVAEKFKEAF | LRKMRKRLMR | SEQ ID NO: 52 |
| DWFKAFYDKVAEKFKEAF | LRKL$^P$KRLLR | SEQ ID NO: 53 |
| DWFKAFYDKVAEKFKEAF | LR$^N$VRKRLVR | SEQ ID NO: 54 |
| DWFKAFYDKVAEKFKEAF | MRKLRKRVLR | SEQ ID NO: 55 |
| DWFKAFYDKVAEKFKEAF | LRRLRRRLLR | SEQ ID NO: 56 |
| DWFKAFYDKVAEKFKEAF | LRKLRKR$^{FF}$R | SEQ ID NO: 57 |

The disclosed domain switched synthetic apolipoprotein E-mimicking peptides can also be N-terminally protected using acetyl and amino groups.

Also disclosed are synthetic apolipoprotein E-mimicking peptides, consisting of a combination of the disclosed receptor binding domains of apolipoprotein E and the disclosed lipid-associating peptides, wherein said receptor binding domain is covalently linked to said lipid-associating peptide in a reversed orientation. For example, disclosed are synthetic apolipoprotein E-mimicking peptides, consisting of a combination of the disclosed receptor binding domains of apolipoprotein E and the disclosed lipid-associating peptides, wherein either the sequence of the receptor binding domain or the sequence of the lipid-associating peptide or both sequences are in the reversed orientation. Also disclosed are synthetic apolipoprotein E-mimicking peptides, consisting of a combination of the disclosed receptor binding domains of apolipoprotein B and the disclosed lipid-associating peptides, wherein said receptor binding domain is covalently linked to said lipid-associating peptide in a reversed orientation. Non-limiting examples of the disclosed synthetic apolipoprotein E-mimicking peptides are provided in Table 4.

TABLE 4

Non-limiting Examples of Synthetic Apolipoprotein E-Mimicking Peptides

| Receptor Binding Domains of ApoE | Lipid-Associating Peptides | SEQ ID NO: |
|---|---|---|
| RLLRKRLKRL | DWLKAFYDKVAEKLKEAF | SEQ ID NO: 64 |
| RLLRKRLKRL | DWLKAFYDKVAEKLKEAF | SEQ ID NO: 65 |
| RLLRKRLKRL | DWLKAFYDKVAEKLKEAF | SEQ ID NO: 66 |
| RMLRKRMKRL | DWLKAFYDKVAEKLKEAF | SEQ ID NO: 67 |
| RMLRKRMKRL | DWLKAFYDKVAEKLKEAF | SEQ ID NO: 68 |
| RLLRKPLKRL | DWLKAFYDKVAEKLKEAF | SEQ ID NO: 69 |
| RVLRKRVNRL | DWLKAFYDKVAEKLKEAF | SEQ ID NO: 70 |
| RLVRKRLKRM | DWLKAFYDKVAEKLKEAF | SEQ ID NO: 71 |
| RLLRRRLRRL | DWLKAFYDKVAEKLKEAF | SEQ ID NO: 72 |
| RFFRKRLKRL | DWLKAFYDKVAEKLKEAF | SEQ ID NO: 73 |
| RLLRKRLKRL | DWFKAFYDKVAEKFKEAF | SEQ ID NO: 74 |
| RLLRKRLKRL | DWFKAFYDKVAEKFKEAF | SEQ ID NO: 75 |
| RLLRKRLKRL | DWFKAFYDKVAEKFKEAF | SEQ ID NO: 76 |
| RMLRKRMKRL | DWFKAFYDKVAEKFKEAF | SEQ ID NO: 77 |
| RMLRKRMKRL | DWFKAFYDKVAEKFKEAF | SEQ ID NO: 78 |
| RLLRKPLKRL | DWFKAFYDKVAEKFKEAF | SEQ ID NO: 79 |
| RVLRKRVNRL | DWFKAFYDKVAEKFKEAF | SEQ ID NO: 80 |
| RLVRKRLKRM | DWFKAFYDKVAEKFKEAF | SEQ ID NO: 81 |
| RLLRRRLRRL | DWFKAFYDKVAEKFKEAF | SEQ ID NO: 82 |
| RFFRKRLKRL | DWFKAFYDKVAEKFKEAF | SEQ ID NO: 83 |
| LRKLRKRLLR | FAEKLKEAVKDYFAKLWD | SEQ ID NO: 84 |
| LRKLRKRLLR | FAEKLKEAVKDYFAKLWD | SEQ ID NO: 85 |
| LRKLRKRLLR | FAEKLKEAVKDYFAKLWD | SEQ ID NO: 86 |
| LRKMRKRLMR | FAEKLKEAVKDYFAKLWD | SEQ ID NO: 87 |
| LRKMRKRLMR | FAEKLKEAVKDYFAKLWD | SEQ ID NO: 88 |
| LRKLPKRLLR | FAEKLKEAVKDYFAKLWD | SEQ ID NO: 89 |
| LRNVRKRLVR | FAEKLKEAVKDYFAKLWD | SEQ ID NO: 90 |
| MRKLRKRVLR | FAEKLKEAVKDYFAKLWD | SEQ ID NO: 91 |
| LRRLRRRLLR | FAEKLKEAVKDYFAKLWD | SEQ ID NO: 92 |
| LRKLRKRFFR | FAEKLKEAVKDYFAKLWD | SEQ ID NO: 93 |
| LRKLRKRLLR | FAEKFKEAVKDYFAKFWD | SEQ ID NO: 94 |
| LRKLRKRLLR | FAEKFKEAVKDYFAKFWD | SEQ ID NO: 95 |
| LRKLRKRLLR | FAEKFKEAVKDYFAKFWD | SEQ ID NO: 96 |
| LRKMRKRLMR | FAEKFKEAVKDYFAKFWD | SEQ ID NO: 97 |
| LRKMRKRLMR | FAEKFKEAVKDYFAKFWD | SEQ ID NO: 98 |
| LRKLPKRLLR | FAEKFKEAVKDYFAKFWD | SEQ ID NO: 99 |
| LRNVRKRLVR | FAEKFKEAVKDYFAKFWD | SEQ ID NO: 100 |
| MRKLRKRVLR | FAEKFKEAVKDYFAKFWD | SEQ ID NO: 101 |
| LRRLRRRLLR | FAEKFKEAVKDYFAKFWD | SEQ ID NO: 102 |
| LRKLRKRFFR | FAEKFKEAVKDYFAKFWD | SEQ ID NO: 103 |

The disclosed reverse-oriented synthetic apolipoprotein E-mimicking peptides can also be N-terminally and C-terminally protected using acetyl and amide groups.

Also disclosed are synthetic apolipoprotein E-mimicking peptides, consisting of a receptor binding domain of apolipoprotein E and a lipid-associating peptide, wherein said receptor binding domain is covalently linked to said lipid-associating peptide, wherein the receptor binding domain of apolipoprotein E is scrambled. For example, disclosed is a synthetic apolipoprotein E-mimicking peptide, consisting of a receptor binding domain of apolipoprotein E comprising the amino acid sequence of SEQ ID NO: 58; and a lipid-associating peptide, wherein said receptor binding domain is covalently linked to said lipid-associating peptide. Also disclosed are synthetic apolipoprotein E-mimicking peptides, consisting of: a receptor binding domain of apolipoprotein B and a lipid-associating peptide, wherein said receptor binding domain is covalently linked to said lipid-associating peptide, wherein the receptor binding domain of apolipoprotein B is scrambled.

Also disclosed are synthetic apolipoprotein E-mimicking peptides, consisting of: a receptor binding domain of apolipoprotein E and a lipid-associating peptide, wherein said receptor binding domain is covalently linked to said lipid-associating peptide, wherein the lipid-associating peptide is scrambled. For example, disclosed herein is a synthetic apolipoprotein E-mimicking peptides, comprising: a lipid binding domain of apolipoprotein E comprising the amino acid sequence of SEQ ID NO: 59 and a receptor binding domain peptide, wherein said lipid binding domain is covalently linked to said receptor binding domain peptide.

Also disclosed are synthetic apolipoprotein E-mimicking peptides, consisting of a receptor binding domain of apolipoprotein E and a lipid-associating peptide of apolipoprotein E, wherein receptor binding domain is covalently linked to said lipid-associating peptide, wherein both the receptor binding domain and the lipid-associating peptide are scrambled. Non-limiting examples of the disclosed scrambled synthetic apolipoprotein E-mimicking peptides are provided in Table 5.

TABLE 5

Scrambled Synthetic Apoliprotein E-Mimicking Peptides

| Name | Receptor Binding Domains of ApoE | Lipid-Associating Peptides | SEQ ID NO: |
|---|---|---|---|
| hE-Sc18A (hE with Sc18A also referred to as Sc2F) | LRKLRKRLLR | KAFEEVLAKKFYDKALWD | SEQ ID NO: 60 |
| SchE-18A | LRLLRKLKRR | DWLKAFYDKVAEKLKEAF | SEQ ID NO: 61 |

The disclosed scrambled synthetic apolipoprotein E-mimicking peptides can also be N-terminally and C-terminally protected using acetyl and amide groups. The disclosed scrambled synthetic apolipoprotein E-mimicking peptides can also be reverse-oriented as described above.

Also disclosed are single-domain synthetic apolipoprotein E-mimicking peptides. The single-domain synthetic apolipoprotein E-mimicking peptides can consist of a receptor binding domain of apolipoprotein E or a lipid-associating peptide. The receptor binding domain or the lipid-associating peptide can be modified or altered as described above. For example, the receptor binding domain or the lipid-associating peptide can be mutated, scrambeled, and/or reverse-oriented. Any other modifications or alterations disclosed herein for the dual-domain polypeptides can also be used for the single-domain peptides. Numerous other variants or derivatives of the peptides disclosed herein are also contemplated. For example, scrambled peptides can also be reverse-oriented, or can be in a switched orientation. Additionally, reverse-oriented peptides can be in a switched orientation. All other combinations of the disclosed peptides are also contemplated. Non-limiting examples of the peptides have been described herein (see Tables 1-5, for example). As used herein, the term "analog" is used interchangeably with "variant" and "derivative." Variants and derivatives are well understood to those of skill in the art and can involve amino acid sequence modifications. Such, amino acid sequence modifications typically fall into one or more of three classes: substantial; insertional; or deletional variants. Insertions include amino and/or carboxyl terminal fusions as well as intrasequence insertions of single or multiple amino acid residues. Insertions ordinarily are smaller insertions than those of amino or carboxyl terminal fusions, for example, on the order of one to four residues. These variants ordinarily are prepared by site-specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once. Substitutions, deletions, insertions or any combination thereof may be combined to arrive at a final derivative or analog. Substutitional variants are those in which at least one residue has been removed and a different residue inserted in its place. Such substitutions generally are made in accordance with Tables 6 and 7 and are referred to as conservative substitutions.

Substantal changes in function or immunological identity are made by selecting substitutions that are less conservative than those in Table 6, i.e., selecting residues that differ more significantly in their effect on maintaining (a) the structure of the polypeptide backbone in the area of the substitution, for example as a sheet or helical conformation, (b) the charge or hydrophobicity of the molecule at the target site, or (c) the bulk of the side chain. The substitutions which in general are expected to produce the greatest changes in the protein properties are those in which: (a) the hydrophilic residue, e.g. seryl or threonyl, is substituted for (or by) a hydrophobic residue, e.g., leucyl, isoleucyl, phenylalanyl, valyl or alanyl; Tryptophan, Tyrosinyl (b) a cysteine or proline is substituted for (or by) any other residue; (c) a residue having an electropositive side chain, e.g., lysyl, arginyl, or hystidyl, is substituted for (or by) an electronegative residue, e.g. glutamyl or aspartyl; or (d) a residue having a bulky side chain, e.g., phenylalanine, is substituted for (or by) one not having a side chain, e.g., glycine, in this case, or (e) by increasing the number of sites for sulfation and/or glycosylation.

TABLE 6

Amino Acid Substitutions

| Original Residue | Non-limiting Exemplary Conservative Substitutions |
|---|---|
| Ala | Ser |
| Arg | Gly; Gln; Lys |
| Asn | Gln; His |
| Asp | Glu |
| Cys | Ser |
| Gln | Asn; Lys |
| Glu | Asp |
| Gly | Ala |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

TABLE 7

Amino Acid Abbreviations

| Amino Acid | Abbreviations |
|---|---|
| Alanine | Ala (A) |
| Allosoleucine | AIle |
| Arginine | Arg (R) |
| Asparagine | Asn (N) |
| Aspartic Acid | Asp (D) |
| Cysteine | Cys (C) |
| Glutamic Acid | Glu (E) |
| Glutamine | Gln (Q) |
| Glycine | Gly (G) |
| Histidine | His (H) |

TABLE 7-continued

Amino Acid Abbreviations

| Amino Acid | Abbreviations |
|---|---|
| Isolelucine | Ile (I) |
| Leucine | Leu (L) |
| Lysine | Lys (K) |
| Phenylalanine | Phe (F) |
| Praline | Pro (P) |
| Pyroglutamic Acid | PGlu (U) |
| Serine | Ser (S) |
| Threonine | Thr (T) |
| Tyrosine | Tyr (Y) |
| Tryptophan | Trp (W) |
| Valine | Val (V) |

It is understood that one way to define the variants and derivatives of the disclosed proteins herein is to define them in terms of homology/identity to specific known sequences. Specifically disclosed are variants of synthetic apolipoprotein E-mimicking peptides and other proteins or peptides herein disclosed which have at least, 70% or at least 75% or at least 80% or at least 85% or at least 90% or at least 95% homology to the synthetic apolipoprotein E-mimicking peptides specifically recited herein. Those of skill in the art readily understand how to determine the homology of two proteins.

As this specification discusses various polypeptides and polypeptide sequences it is understood that the nucleic acids that can encode those polypeptide sequences are also disclosed. This would include all degenerate sequences related to a specific polypeptide sequence, i.e. all nucleic acids having a sequence that encodes one particular polypeptide sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed polypeptide sequences.

Blocking/Protecting Groups and D Residues

While the various compositions described herein may be shown with no protecting groups, in certain embodiments (e.g., particularly for oral administration), they can bear one, two, three, four, or more protecting groups. The protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g., an acetyl group protecting the amino terminus and/or an amide group protecting the carboxyl terminus. One example of such a "dual protected peptide" is Ac-LRKLRKRLLRD-WLKAFYDKVAEKLKEAF-NH$_2$ (SEQ ID NO:12 with blocking groups), either or both of these protecting groups can be eliminated and/or substituted with another protecting group as described herein. Without being bound by a particular theory, it was a discovery of this invention that blockage, particularly of the amino and/or carboxyl termini of the subject peptides of this invention can improve oral delivery and can also increase serum half-life.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. For example, the protecting groups can include, but are not limited to alkyl chains as in fatty acids, propeonyl, formyl, and others. Carboxyl protecting groups include amides, esters, and ether-forming protecting groups can also be used. For example, an acetyl group can be used to protect the amino terminus and an amide group can be used to protect the carboxyl terminus. These blocking groups enhance the helix-forming tendencies of the peptides. Additional blocking groups include alkyl groups of various lengths, e.g., groups having the formula: CH$_3$(CH$_2$)$_n$CO where n ranges from about 1 to about 20, preferably from about 1 to about 16 or 18, more preferably from about 3 to about 13, and most preferably from about 3 to about 10.

Additionally, the protecting groups include, but are not limited to alkyl chains as in fatty acids, propeonyl, formyl, and others. For example, carboxyl protecting groups can include amides, esters, and ether-forming protecting groups. These blocking groups can enhance the helix-forming tendencies of the peptides. Blocking groups can include alkyl groups of various lengths, e.g., groups having the formula: CH$_3$(CH$_2$)$_n$CO where n ranges from about 3 to about 20, preferably from about 3 to about 16, more preferably from about 3 to about 13, and most preferably from about 3 to about 10.

Other protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxy-carbonyl (2-Br-Z), Benzyloxymethyl (Born); cyclohexyloxy (cHxO),t-butoxymethyl (Bum), t-butoxy (tBuO), t-Butyl (tBu), Acetyl (Ac), and Trifluoroacetyl (TFA).

Protecting/blocking groups are well known to those of skill as are methods of coupling such groups to the appropriate residue(s) comprising the peptides of this invention (see, e.g., Greene et al., (1991) Protective Groups in Organic Synthesis, 2nd ed., John Wiley & Sons, Inc. Somerset, N.J.). For example, acetylation can be accomplished during the synthesis when the peptide is on the resin using acetic anhydride. Amide protection can be achieved by the selection of a proper resin for the synthesis.

The compositions disclosed herein can also comprise one or more D-form (dextro rather than levo) amino acids as described herein. For example, at least two enantiomeric amino acids, at least 4 enantiomeric amino acids or at least 8 or 10 enantiomeric amino acids can be in the "D" form amino acids. Additionally, every other, or even every amino acid (e.g., every enantiomeric amino acid) of the peptides described herein is a D-form amino acid.

Additionally, at least 50% of the enantiomeric amino acids can be "D" form, at least 80% of the enantiomeric amino acids are "D" form, at least 90%, or even all of the enantiomeric amino acids can be in the "D" form amino acids.

Polypeptide Production

Polypeptides of the invention are produced by any method known in the art. One method of producing the disclosed polypeptides is to link two or more amino acid residues, peptides or polypeptides together by protein chemistry techniques. For example, peptides or polypeptides are chemically synthesized using currently available laboratory equipment using either Fmoc (9-fluorenylmethyloxycarbonyl) or Boc (tert-butyloxycarbonoyl) chemistry (Applied Biosystems, Inc., Foster City, Calif.). A peptide or polypeptide can be synthesized and not cleaved from its synthesis resin, whereas the other fragment of a peptide or protein can be synthesized and subsequently cleaved from the resin, thereby exposing a terminal group, which is functionally blocked on the other fragment. By peptide condensation reactions, these two fragments can be covalently joined via a peptide bond at their carboxyl and amino termini, respectively, (Grant GA (.1992) *Synthetic Peptides: A User Guide.* W.H. Freeman and Co., N.Y. (1992); Bodansky M and Trost B., Ed. (1993). *Principles of Peptide Synthesis.* Springer-Verlag Inc., NY). Alternatively, the peptide or polypeptide is independently synthesized in vivo. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry,* 30:4151 (1991)).

Alternatively, native chemical ligation of synthetic peptides can be utilized to synthetically construct large peptides or polypeptides from shorter peptide fragments. This method consists of a two-step chemical reaction (Dawson et al. *Science,* 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolim M et al. (1992) *FEBS Lett.* 307:97-101; Clark-Lewis I et al., *J. Biol. Chem.,* 269:16075 (1994); Clark-Lewis I et al., *Biochem.,* 30:3128 (1991); Rajarathnam K et al., *Biochem.* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science,* 256:221 (1992)). This technique has been used to synthesize analogs of protein domains as well as large amounts of relatively pure proteins with full biological activity (deLisle Milton R C et al., *Techniques in Protein Chemistry IV.* Academic Press, New York, pp. 257-267 (1992)).

Antibodies

Also disclosed herein are isolated antibodies, antibody fragments and antigen-binding fragments thereof, that specifically bind to one or more of the synthetic apolipoprotein E-mimicking peptides disclosed herein. Optionally, the isolated antibodies, antibody fragments, or antigen-binding fragment thereof can be neutralizing antibodies. The antibodies, antibody fragments and antigen-binding fragments thereof disclosed herein can be identified using the methods disclosed herein. For example, antibodies that bind to the polypeptides of the invention can be isolated using the antigen microarray described elsewhere herein.

The term "antibodies" is used herein in a broad sense and includes both polyclonal and monoclonal antibodies. In addition to intact immunoglobulin molecules, also disclosed are antibody fragments or polymers of those immunoglobulin molecules, and human or humanized versions of immunoglobulin molecules or fragments thereof, as long as they are chosen for their ability to interact with the polypeptides disclosed herein. "Antibody fragments" are portions of a complete antibody. A complete antibody refers to an antibody having two complete light chains and two complete heavy chains. An antibody fragment lacks all or a portion of one or more of the chains. Examples of antibody fragments include, but are not limited to, half antibodies and fragments of half antibodies. A half antibody is composed of a single light chain and a single heavy chain. Half antibodies and half antibody fragments can be produced by reducing an antibody or antibody fragment having two light chains and two heavy chains. Such antibody fragments are referred to as reduced antibodies. Reduced antibodies have exposed and reactive sulfhydryl groups. These sulfhydryl groups can be used as reactive chemical groups or coupling of biomolecules to the antibody fragment. A preferred half antibody fragment is a F(ab). The hinge region of an antibody or antibody fragment is the region where the light chain ends and the heavy chain goes on.

Antibody fragments for use in antibody conjugates can bind antigens. Preferably, the antibody fragment is specific for an antigen. An antibody or antibody fragment is specific for an antigen if it binds with significantly greater affinity to one epitope than to other epitopes. The antigen can be any molecule, compound, composition, or portion thereof to which an antibody fragment can bind. An analyte can be any molecule, compound or composition of interest. For example, the antigen can be a polynucleotide of the invention. The antibodies or antibody fragments can be tested for their desired activity using the in vitro assays described herein, or by analogous methods, after which their in vivo therapeutic or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. Also disclosed are "chimeric" antibodies in which a portion of the heavy or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, such as an Fv, Fab, Fab', or other antigen-binding portion of an antibody, can be accomplished using routine techniques known in the art. For instance, digestion can be performed using papain. Examples of papain digestion are described in WO 94/29348 published Dec. 22, 1994 and U.S. Pat. No. 4,342,566, the contents of which are hereby incorporated by reference in its entirety for its teaching of papain digestion of antibodies to prepare monovaltent antibodies. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

The disclosed human antibodies can be prepared using any technique. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1):86-95, 1991). Human antibodies (and fragments thereof) can also be produced using phage display libraries (Hoogenboom et al., J. Mol. Biol., 227:381, 1991; Marks et al., J. Mol. Biol., 222: 581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551-255 (1993); Jakobovits et al., Nature, 362:255-258 (1993); Bruggermann et al., Year in Immunol., 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Optionally, the disclosed human antibodies can be made from memory B cells using a method for Epstein-Barr virus transformation of human B cells. (See, e.g., Triaggiai et al., An efficient method to make human monoclonal antibodies from memory B cells: potent neutralization of SARS coronavirus, Nat Med. 2004 August; 10(8):871-5. (2004)), which is herein incorporated by reference in its entirety for its teaching of a method to make human monoclonal antibodies from memory B cells). In short, memory B cells from a subject who has survived a natural infection are isolated and immortalized with EBV in the presence of irradiated mononuclear cells and a CpG oligonuleotide that acts as a polyclonal activator of memory B cells. The memory B cells are cultured and analyzed for the presence of specific antibodies. EBV-B cells from the culture producing the antibodies of the desired specificity are then cloned by limiting dilution in the presence of irradiated mononuclear cells, with the addition of CpG 2006 to increase cloning efficiency, and cultured. After culture of the EBV-B cells, monoclonal antibodies can be isolated. Such a method offers (1) antibodies that are produced by immortalization of memory B lymphocytes which are stable over a lifetime and can easily be isolated from peripheral blood and (2) the antibodies isolated from a primed natural host who has survived a natural infection, thus eliminating the need for immunization of experimental animals, which may show different susceptibility and, therefore, different immune responses.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323-327 (1988), and Presta, Curr. Opin. Struct. Biol., 2:593-596 (1992)).

Methods for humanizing non-human antibodies are well known in the art. For example, humanized antibodies can be generated according to the methods of Winter and co-workers (Jones et al., Nature, 321:522-525 (1986), Riechmann et al., Nature, 332:323-327 (1988), Verhoeyen et al., Science, 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.). The antibodies disclosed herein can also be administered to a subject. Nucleic acid approaches for antibody delivery also exist. The broadly neutralizing antibodies to the polypeptides disclosed herein and antibody fragments can also be administered to subjects or subjects as a nucleic acid preparation (e.g., DNA or RNA) that encodes the antibody or antibody fragment, such that the subject's own cells take up the nucleic acid and produce and secrete the encoded antibody or antibody fragment.

Nucleic Acid and Vectors

The invention is also directed to an isolated nucleic acid encoding any one or more of the synthetic apolipoprotein E-mimicking peptides disclosed herein. For example, disclosed are isolated nucleic acid encoding the disclosed synthetic apolipoprotein E-mimicking peptides, wherein the nucleic acid comprises DNA, RNA and/or cDNA. It would be routine for one with ordinary skill in the art to make a nucleic acid that encodes the polypeptides disclosed herein since codons for each of the amino acids that make up the polypeptides are known.

The disclosed nucleic acids are made up of for example, nucleotides, nucleotide analogs, or nucleotide substitutes. Non-limiting examples of these and other molecules are discussed herein. It is understood that for example, when a vector is expressed in a cell that the expressed mRNA will typically be made up of A, C, G, and U. Likewise, it is understood that if, for example, an antisense molecule is introduced into a cell or cell environment through for example exogenous delivery, it is advantagous that the antisense molecule be made up of nucleotide analogs that reduce the degradation of the antisense molecule in the cellular environment.

The nucleotides of the invention can comprise one or more nucleotide anaologs or substitutions. A nucleotide analog is a nucleotide which contains some type of modification to the base, sugar, or phosphate moieties. Modifications to the base moiety would include natural and synthetic modifications of A, C, G, and TX as well as different purine or pyrimidine bases, such as uracil-5-yl ($\psi$), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modifcation, such as 2'-O-methoxyethyl, to achieve unique properties such as increased duplex stability. There are numerous United States patents, such as U.S. Pat. Nos. 4,845,205; 5,130,302; 5,134, 066; 5,175,273; 5,3.67,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[$(CH_2)_n$ O]$_m$ CH$_3$, —O$(CH_2)_n$ OCH$_3$, —O$(CH_2)_n$ NH$_2$, —O$(CH_2)_n$ CH$_3$, —O$(CH_2)_n$ —ONH$_2$, and —O$(CH_2)_n$ON [$(CH_2)_n$ CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981, 957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety for their teaching of modifications and methods related to the same.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-lkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference in its entirety for their teaching of modifications and methods related to the same.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety or sugar moieties replaced. Nucleotide substitutes do not contain a standard phosphorus atom. Substitutes for the phosphate can be, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference in its entirety for their teaching of modifications and methods related to the same.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference in its entirety for their teaching of modifications and methods related to the same. (See also Nielsen et al., *Science*, 254, 1497-1500 (1991)).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference in its entirety for their teaching of modifications and methods related to the same.

The same methods of calculating homology as described elsewhere herein concerning polypeptides can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

Also, disclosed are compositions including primers and probes, which are capable of interacting with the polynucleotide sequences disclosed herein. For example, disclosed are primers/probes capable of amplifying a nucleic acid capable of encoding one or more of the disclosed synthetic apolipoprotein E-mimicking peptides. The disclosed primers can used to support DNA amplification reactions. Typically the primers will be capable of being extended in a sequence specific manner. Extension of a primer in a sequence specific manner includes any methods wherein the sequence or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the polynucleotide sequences disclosed herein or region of the polynucleotide sequences disclosed herein or they hybridize with the complement of the polynucleotide sequences disclosed herein or complement of a region of the polynucleotide sequences disclosed herein.

The size of the primers or probes for interaction with the polynucleotide sequences disclosed herein in certain embodiments can be any size that supports the desired enzymatic manipulation of the primer, such as DNA amplification or the simple hybridization of the probe or primer. A typical primer or probe would be at least 6, 7, 8, 9, 10, 20, 30, 40, 50, 60, 70, 80, 90, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long or any length inbetween.

Also disclosed are functional nucleic acids that can interact with the disclosed polynucleotides. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of polynucleotide sequences disclosed herein or the genomic DNA of the polynucleotide sequences disclosed herein or they can interact with the polypeptide encoded by the polynucleotide sequences disclosed herein. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Disclosed herein are antisense molecules that interact with the disclosed polynucleotides. Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437 each of which is herein incorporated by reference in its entirety for their teaching of modifications and methods related to the same.

Also disclosed are aptamers that interact with the disclosed polynucleotides. Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide. For example, when determining the specificity of aptamers, the background protein could be ef-1α. Representative examples of how to make and use aptamers to bind a variety of different target molecules can be found in the following non-limiting list of U.S. Pat. Nos. 5,476,766; 5,503,978; 5,631,146; 5,731,424; 5;780,228; 5,792,613; 5,795,721; 5,846,713; 5,858,660; 5,861,254; 5,864,026; 5,869,641; 5,958,691; 6,001,988; 6,011,020; 6,013,443; 6,020,130; 6,028,186; 6,030,776, and 6,051,698.

Also disclosed are ribozymes that interact with the disclosed polynucleotides. Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711; 5,436,330; 5,616,466; 5,633,133; 5,646,020; 5,652,094; 5,712,384; 5,770,715; 5,856,463; 5,861,288; 5,891,683; 5,891,684; 5,985,621; 5,989,908; 5,998,193; 5,998,203; WO 9858058 by Ludwig and Sproat; WO 9858057 by Ludwig and Sproat, and WO 9718312 by Ludwig and Sproat) hairpin ribozymes (for example, but not limited to the following U.S. Pat. Nos. 5,631,115; 5,646,031; 5,683,902; 5;712,384; 5,856,188; 5,866,701; 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967; 5,688,670; 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042; 5,693,535; 5,731,295; 5,811,300; 5,837,855; 5,869,253; 5,877,021; 5,877,022; 5,972,699; 5,972,704; 5,989,906, and 6,017,756.

Also disclosed are triplex forming functional nucleic acid molecules that interact with the disclosed polynucleotides. Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. Pat. Nos. 5,176,996; 5,645,985; 5,650,316; 5,683,874; 5,693,773; 5,834,185; 5,869,246; 5,874,566, and 5,962,426.

Also disclosed are external guide sequences that form a complex with the disclosed polynucleotides. External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, Science 238:407-409 (1990)).

Similarly, eukaryotic EGS/RNAse P-directed cleavage of RNA can be utilized to cleave desired targets within eukarotic cells. (Yuan et al., Proc. Natl. Acad. Sci. USA 89:8006-8010 (1992); WO 93/22434 by Yale; WO 95/24489 by Yale; Yuan and Altman, EMBO J 14:159-168 (1995), and Carrara et al., Proc. Natl. Acad. Sci. (USA) 92:2627-2631 (1995)). Representative examples of how to make and use EGS molecules to facilitate cleavage of a variety of different target molecules can be found in the following non-limiting list of U.S. Pat. Nos. 5,168,053; 5,624,824; 5,683,873; 5,728,521; 5,869,248; and 5,877,162.

Also disclosed are polynucleotides that contain peptide nucleic acids (PNAs) compositions. PNA is a DNA mimic in which the nucleobases are attached to a pseudopeptide backbone (Good and Nielsen, Antisense Nucleic Acid Drug Dev. 1997; 7(4) 431-37). PNA is able to be utilized in a number of methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (Trends Biotechnol 1997 June; 15(6): 224-9). As such, in certain embodiments, one may prepare PNA sequences that are complementary to one or more portions of an mRNA sequence based on the disclosed polynucleotides, and such PNA compositions may be used to regulate, alter, decrease, or reduce the translation of the disclosed polynucleotides transcribed mRNA, and thereby alter the level of the disclosed polynucleotide's activity in a host cell to which such PNA compositions have been administered.

PNAs have 2-aminoethyl-glycine linkages replacing the normal phosphodiester backbone of DNA (Nielsen et al., Science Dec. 6, 1991; 254(5037):1497-500; Hanvey et al., Science. Nov. 27, 1992; 258(5087):1481-5; Hyrup and Nielsen, Bioorg Med Chem. 1996 January; 4(1):5-23). This chemistry has three important consequences: firstly, in contrast to DNA or phosphorothioate oligonucleotides, PNAs are neutral molecules; secondly, PNAs are achirial, which avoids the need to develop a stereoselective synthesis; and thirdly, PNA synthesis uses standard Boc or Fmoc protocols for solid-phase peptide synthesis, although other methods, including a modified Merrifield method, have been used. PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. 1995 April; 3(4):437-45). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. 1995 April; 3(4):437-45; Petersen et al., J Pept Sci. 1995 May-June; 1(3):175-83; Orum et al., Biotechniques. 1995 September; 19(3):472-80; Footer et al., Biochemistry. Aug. 20, 1996; 35(33): 10673-9; Griffith et al., Nucleic Acids Res. Aug. 11, 1995; 23(15):3003-8; Pardridge et al., Proc Natl Acad Sci USA. Jun. 6, 1995; 92(12):5592-6; Boffa et al., Proc Natl Acad Sci USA. Mar. 14, 1995; 92(6):1901-5; Gambacorti-Passerini et al., Blood. Aug. 15, 1996; 88(4):1411-7; Armitage et al., Proc Natl Acad Sci USA. Nov. 11, 1997; 94(23):12320-5; Seeger et al., Biotechniques. 1997 September; 23(3):512-7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. Dec. 15, 1993; 65(24):3545-9) and Jensen et al. (Biochemistry. Apr. 22, 1997; 36(16):5072-7). Rose uses capillary gel electrophoresis to determine binding of PNAs to their complementary oligonucleotide, measuring the relative binding kinetics and stoichiometry. Similar types of measurements were made by Jensen et al. using BIAcore™ technology. Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Optionally, isolated polypeptides or isolated nucleotides can also be purified, e.g., are at least about 90% pure, more preferably at least about 95% pure and most preferably at least about 99% pure. An "isolated" polypeptide or an "isolated" polynucleotide is one that is removed from its original environment. For example, a naturally-occurring polypeptide or polynucleotide is isolated if it is separated from some or all of the coexisting materials in the natural system.

Also disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular polynucleotide is disclosed and discussed and a number of modifications that can be made to a number of molecules including the polynucleotide are discussed, specifically contemplated is each and every combination and permutation of polynucleotide and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that one way to define any known variants and derivatives or those that might arise, of the disclosed genes and proteins herein is through defining the variants and derivatives in terms of homology to specific known sequences. Specifically disclosed are variants of the genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, New York, 1989; Kunkel et al. Methods Enzymol. 1987:154:367, 1987 which is herein incorporated by reference in its entirety and at least for material related to hybridization of nucleic acids). As used herein "stringent hybridization" for a DNA:DNA hybridization is about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein. Optionally, one or more of the isolated polynucleotides of the invention are attached to a solid support. Solid supports are disclosed herein.

Also disclosed herein are arrays comprising polynucleotides capable of specifically hybridizing to nucleic acid capable of encoding the disclosed synthetic apolipoprotein E mimicking peptides. Also disclosed are arrays comprising polynucleotides capable of specifically hybridizing to nucleic acid capable of encoding the disclosed synthetic apolipoprotein E mimicking peptides.

Solid supports are solid-state substrates or supports with which molecules, such as analytes and analyte binding molecules, can be associated. Analytes, such as calcifying nanoparticles and proteins, can be associated with solid supports directly or indirectly. For example, analytes can be directly immobilized on solid supports. Analyte capture agents, such a capture compounds, can also be immobilized on solid supports. For example, disclosed herein are antigen binding agentscapable of specifically binding to nucleic acid capable of encoding the disclosed synthetic apolipoprotein E mimicking peptides. A preferred form of solid support is an array. Another form of solid support is an array detector. An array detector is a solid support to which multiple different capture compounds or detection compounds have been coupled in an array, grid, or other organized pattern. Solid-state substrates for use in solid supports can include any solid material to which molecules can be coupled. This includes materials such as acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A preferred form for a solid-state substrate is a microtiter dish, such as a standard 96-well type. In preferred embodiments, a multiwell glass slide can be employed that normally contain one array per well. This feature allows for greater control of assay reproducibility, increased throughput and sample handling, and ease of automation.

Different compounds can be used together as a set. The set can be used as a mixture of all or subsets of the compounds used separately in separate reactions, or immobilized in an array. Compounds used separately or as mixtures can be physically separable through, for example, association with or immobilization on a solid support. An array can include a plurality of compounds immobilized at identified or predefined locations on the array. Each predefined location on the array generally can have one type of component (that is, all the components at that location are the same). Each location will have multiple copies of the component. The spatial separation of different components in the array allows separate detection and identification of the polynucleotides or polypeptides disclosed herein.

Although preferred, it is not required that a given array be a single unit or structure. The set of compounds may be distributed over any number of solid supports. For example, at one extreme, each compound may be immobilized in a separate reaction tube or container, or on separate beads or microparticles. Different modes of the disclosed method can be performed with different components (for example, different compounds specific for different proteins) immobilized on a solid support. Some solid supports can have capture compounds, such as antibodies, attached to a solid-state substrate. Such capture compounds can be specific for calcifying nano-particles or a protein on calcifying nano-particles. Captured calcifying nano-particles or proteins can then be detected by binding of a second, detection compound, such as an antibody. The detection compound can be specific for the same or a different protein on the calcifying nano-particle.

Methods for immobilizing antibodies (and other proteins) to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is the heterobifunctional cross-linker N-[γ-Maleimidobutyryloxy]succinimide ester (GMBS). These and other attachment agents, as well as methods for their use in attachment, are described in Protein immobilization: fundamentals and applications, Richard F. Taylor, ed. (M. Dekker, New York, 1991), Johnstone and Thorpe, Immunochemistry In Practice (Blackwell Scientific Publications, Oxford, England, 1987) pages 209-216 and 241-242, and Immobilized Affinity Ligands; Craig T. Hermanson et al., eds. (Academic Press, New York, 1992) which are incorporated by reference in their entirety for methods of attaching antibodies to a solid-state substrate. Antibodies can be attached to a substrate by chemically cross-linking a free amino group on the antibody to reactive side groups present within the solid-state substrate. For example, antibodies may be chemically cross-linked to a substrate that contains free amino, carboxyl, or sulfur groups using glutaraldehyde, carbodiimides, or GMBS, respectively, as cross-linker agents. In this method, aqueous solutions containing free antibodies are incubated with the solid-state substrate in the presence of glutaraldehyde or carbodiimide.

A preferred method for attaching antibodies or other proteins to a solid-state substrate is to functionalize the substrate with an amino- or thiol-silane, and then to activate the functionalized substrate with a homobifunctional cross-linker agent such as (Bis-sulfo-succinimidyl suberate ($BS^3$) or a heterobifunctional cross-linker agent such as GMBS. For cross-linking with GMBS, glass substrates are chemically functionalized by immersing in a solution of mercaptopropyltrimethoxysilane (1% vol/vol in 95% ethanol pH 5.5) for 1 hour, rinsing in 95% ethanol and heating at 120° C. for 4 hrs. Thiol-derivatized slides are activated by immersing in a 0.5 mg/ml solution of GMBS in 1% dimethylformamide, 99% ethanol for 1 hour at room temperature. Antibodies or proteins are added directly to the activated substrate, which are then blocked with solutions containing agents such as 2% bovine serum albumin, and air-dried. Other standard immobilization chemistries are known by those of skill in the art.

Each of the components (compounds, for example) immobilized on the solid support preferably is located in a different predefined region of the solid support. Each of the different predefined regions can be physically separated from each other of the different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components preferably are immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

Optionally, at least one address on the solid support is the sequences or part of the sequences set forth in any of the nucleic acid sequences disclosed herein. Also disclosed are solid supports where at least one address is the sequences or portion of sequences set forth in any of the peptide sequences disclosed herein. Solid supports can also contain at least one address is a variant of the sequences or part of the sequences set forth in any of the nucleic acid sequences disclosed herein. Solid supports can also contain at least one address is a variant of the sequences or portion of sequences set forth in any of the peptide sequences disclosed herein.

Also disclosed are antigen microarrays for multiplex characterization of antibody responses. For example, disclosed are antigen arrays and miniaturized antigen arrays to perform large-scale multiplex characterization of antibody responses directed against the polypeptides, polynucleotides and antibodies described herein, using submicroliter quantities of biological samples as described in Robinson et al., Autoantigen microarrays for multiplex characterization of autoantibody responses, Nat Med., 8(3):295-301 (2002), which in herein incorporated by reference in its entirety for its teaching of contructing and using antigen arrays to perform large-scale multiplex characterization of antibody responses directed against structurally diverse antigens, using submicroliter quantities of biological samples.

Protein variants and derivatives are well understood to those of skill in the art and can involve amino acid sequence modifications. For example, amino acid sequence modifications typically fall into one or more of three classes: substitutional, insertional or deletional variants. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

Also disclosed are vectors comprising isolated nucleic acids encoding the synthetic apolipoprotein E-mimicking peptides described herein. In certain embodiments, the invention provides a vector comprising a nucleic acid encoding at least one of the peptides of the present invention, e.g., at least one of SEQ ID NOS: 11-14 and 18-61. For example, disclosed are expression vectors comprising the polynucleotides described elsewhere herein, operably linked to a control element.

Also disclosed herein are host cells transformed or transfected with an expression vector comprising the polynucleotides described elsewhere herein. Also disclosed are host cells comprising the expression vectors described herein. For example, disclosed is a host cell comprising an expression vector comprising the polynucleotides described elsewhere herein, operably linked to a control element. Host cells can be eukaryotic or prokaryotic cells. Also disclosed are recombinant cells comprising isolated nucleic acids encoding the disclosed synthetic apolipoprotein E-mimicking peptides. Further disclosed are recombinant cells producing the disclosed synthetic apolipoprotein E-mimicking peptides.

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Expression vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). For example, disclosed herein are expression vectors comprising an isolated polynucleotide capable of encoding one or more of the disclosed synthetic apolipoprotein E-mimicking peptides operably linked to a control element.

The "control elements" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or pSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

Preferred promoters controlling transcription from vectors in mammalian host cells may be obtained from various sources, for example, the genomes of viruses such as polyoma, Simian Virus 40 (SV40), adenovirus, retroviruses, hepatitis-B virus and most preferably cytomegalovirus, or from heterologous mammalian promoters (e.g., beta actin promoter). The early and late promoters of the SV40 virus are conveniently obtained as an SV40 restriction fragment, which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Additionall, promoters from the host cell or related species can also be used.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

Optionally, the promoter or enhancer region can act as a constitutive promoter or enhancer to maximize expression of the polynucleotides of the invention. In certain constructs the promoter or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases.

The expression vectors can include a nucleic acid sequence encoding a marker product. This marker product is used to determine if the gene has been delivered to the cell and once delivered is being expressed. Preferred marker genes are the *E. coli* lacZ gene, which encodes β-galactosidase, and the gene encoding the green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

As used herein, plasmid or viral vectors are agents that transport the disclosed nucleic acids, such as an isolated polynucleotide capable of encoding one or more of the disclosed synthetic apolipoprotein E-mimicking peptides into the cell without degradation and include a promoter yielding expression of the gene in the cells into which it is delivered. In some embodiments the isolated polynucleotides disclosed herein are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction abilities (i.e., ability to introduce genes) than chemical or physical methods of introducing genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

Retroviral vectors, in general, are described by Verma, I. M., Retroviral vectors for gene transfer. In Microbiology, Amer. Soc. for Microbiology, pp. 229-232, Washington, (1985), which is hereby incorporated by reference in its entirety. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference in their entirety for their teaching of methods for using retroviral vectors for gene therapy.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serves as the priming site for the synthesis of the second strand of DNA synthesis, and specific sequences near the ends of the LTRs that enable the insertion of the DNA state of the retrovirus to insert into the host genome. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159

(1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)) the teachings of which are incorporated herein by reference in their entirety for their teaching of methods for using retroviral vectors for gene therapy. Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol., 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. Optionally, both the E1 and E3 genes are removed from the adenovirus genome.

Another type of viral vector that can be used to introduce the polynucleotides of the invention into a cell is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus. Typically the AAV and B19 coding regions have been deleted, resulting in a safe, noncytotoxic vector. The AAV Hits, or modifications thereof, confer infectivity and site-specific integration, but not cytotoxicity, and the promoter directs cell-specific expression. U.S. Pat. No. 6,261,834 is herein incorproated by reference in its entirety for material related to the AAV vector.

The inserted genes in viral and retroviral vectors usually contain promoters, or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Other useful systems include, for example, replicating and host-restricted non-replicating vaccinia virus vectors. In addition, the disclosed polynucleotides can be delivered to a target cell in a non-nucliec acid based system. For example, the disclosed polynucleotides can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed expression vectors, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood, to a target organ, or inhaled into the respiratory tract to target cells of the respiratory tract. For example, a composition comprising a polynucleotide described herein and a cationic liposome can be administered to a subjects lung cells. Regarding liposomes, see, e.g., Brigham et al. Am. J. Resp. Cell. Mol. Biol. 1:95-100 (1989); Feigner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

Delivery of Compositions

In the methods described herein, delivery of the compositions to cells can be via a variety of mechanisms. As defined above, disclosed herein are compositions comprising any one or more of the polypeptides, nucleic acids, vectors and/or antibodies described herein can be used to produce a composition of the invention which may also include a carrier such as a pharmaceutically acceptable carrier. For example, disclosed are pharmaceutical compositions, comprising the synthetic apolipoprotein E-mimicking peptides disclosed herein, and a pharmaceutically acceptable carrier The polypeptide, nucleic acid, vector, or antibody of the invention can be in solution or in suspension (for example, incorporated into microparticles, liposomes, or cells). These compositions can be targeted to a particular cell type via antibodies, receptors, or receptor ligands. One of skill in the art knows how to make and use such targeting agents with the compositions of the invention. A targeting agent can be a vehicle such as an antibody conjugated liposomes; receptor mediated targeting of DNA through cell specific ligands, and highly specific retroviral targeting of cells in vivo. Any such vehicles can be part of the composition of the invention. In general, receptors are involved in pathways of endocytosis, either constitutive or ligand induced. These receptors cluster in clathrin-coated pits, enter the cell via clatrhin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, ligand valency, and ligand concentration.

For example, the compositions described herein can comprise s pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy. (19th ed.) ed. A. R. Gennaro, Mack Publishing Company, Easton, Pa. 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions may also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium choloride solution, Ringer's dextrose, dextrose and sodium choloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

Transgenic Subjects

Also disclosed are transgenic, non-human subjects comprising a nucleic acid capable of encoding one or more of the synthetic apolipoprotein E-mimicking peptides described herein. Also disclosed are transgenic, non-human subjects expressing one or more of the synthetic apolipoprotein E-mimicking peptides described herein. The subject is an animal or a plant. The invention also provides for a transgenic non-human subject expressing one or more of the synthetic apolipoprotein E-mimicking peptides described herein.

The animals can be produced by the process of transfecting a cell within the animal with any of the nucleic acid molecules disclosed herein. Methods for producing transgenic animals would be known to one of skill in the art, e.g., U.S. Pat. No. 6,201,165, to Grant, et al., issued Mar. 13, 2001, entitled "Transgenic animal models for cardiac hypertrophy and methods of use thereof." In non-limiting embodiments, the animal is a mammal, and the mammal is mouse, rat, rabbit, cow, sheep, pig, or primate, such as a human, monkey, ape, chimpanzee, or orangutan. The invention also provides an animal produced by the process of adding to such animal (for example, during an embryonic state) any of the cells disclosed herein.

Compositions (such as vectors) and methods are provided, which can be used for targeted gene disruption and modification to produce the polypeptides of the invention in any animal that can undergo gene disruption. Gene modification and gene disruption refer to the methods, techniques, and compositions that surround the selective removal or alteration of a gene or stretch of chromosome in an animal, such as a mammal, in a way that propagates the modification through the germ line of the mammal. In general, a cell is transformed with a vector, which is designed to homologously recombine with a region of a particular chromosome contained within the cell, as for example, described herein. This homologous recombination event can produce a chromosome which has exogenous DNA introduced, for example in frame, with the surrounding DNA. This type of protocol allows for very specific mutations, such as point mutations or the insertion of DNA to encode for a new polypeptide, to be introduced into the genome contained within the cell. Methods for performing this type of homologous recombination are known to one of skill in the art.

Once a genetically engineered cell is produced through the methods described above, an animal can be produced from this cell through either stem cell technology or cloning technology. For example, if the cell into which the nucleic acid was transfected was a stem cell for the organism, then this cell, after transfection and culturing, can be used to produce a transgenic organism which will contain the gene modification or disruption in germ line cells, which can then in turn be used to produce another animal that possesses the gene modification or disruption in all of its cells. In other methods for production of an animal containing the gene modification or disruption in all of its cells, cloning technologies can be used. These technologies are known to one of skill in the art and generally take the nucleus of the transfected cell and either through fusion or replacement fuse the transfected nucleus with an oocyte, which can then be manipulated to produce an animal. The advantage of procedures that use cloning instead of ES technology is that cells other than ES cells can be transfected. For example, a fibroblast cell, which is very easy to culture and can be used as the cell in this example, which is transfected and has a gene modification or disruption event take place, and then cells derived from this cell can be used to clone a whole animal. Also disclosed are nucleic acids used to modify a gene of interest that is cloned into a vector designed for example, for homologous recombination.

Methods for Making the Compositions of the Invention

The compositions disclosed herein and the compositions necessary to perform the disclosed methods can be made using any method known to those of skill in the art for that particular reagent or compound unless otherwise specifically noted. For example, there are a variety of methods that can be used for making these compositions, such as synthetic chemical methods and standard molecular biology methods. The peptide, polypeptides, nucleic acids and vectors of the invention can be used to make certain other aspects of the invention. For example, the peptides and polypeptides of the invention can be used to produce the antibodies of the invention. Nucleic acids and vectors of the invention can be used to produce the peptides and polypeptides and other recombinant proteins of the invention. Host cells of the invention can be used to make nucleic acids, proteins, peptides, antibodies, and transgenic animals of the invention. These synthetic methods are described above.

As described above, the polypeptides or peptides of the invention may also be used to generate antibodies, which bind specifically to the polypeptides or fragments of the polypeptides. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention, sequences substantially identical thereto, or fragments of the foregoing sequences.

In immunoaffinity procedures, the antibody is attached to a solid support, such as a bead or column matrix. The protein preparation is placed in contact with the antibody under conditions under which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

The antibodies of the invention can be attached to solid supports and used to immobilize apolipoprotein E or polypeptides of the present invention. Polyclonal antibodies generated against the polypeptides of the invention can be obtained by direct injection of the polypeptides into an animal or by administering the polypeptides to an animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

C. Methods of Use

The invention also provides many therapeutic methods of using the nucleic acids, peptides, polypeptides, vectors, antibodies, and compositions disclosed herein. For example, disclosed are methods for enhancing LDL binding to a cell, the method comprising contacting, mixing or associating the cell with one or more of the disclosed synthetic apolipoprotein E-mimicking peptides. The Examples section below provides examples of how the nucleic acids, peptides, polypeptides, vectors, and antibodies, and compositions of the invention can be used and tested. One of skill in the art would be capable of modifying the methods provided in the Examples section to test and use the the nucleic acids, peptides, polypeptides, vectors, antibodies, and compositions disclosed herein.

Also disclosed are methods for enhancing LDL binding to a cell, the method comprising contacting, mixing or associating the cell with one or more of the disclosed synthetic apolipoprotein E-mimicking peptides whereby plasma LDL, plasma VLDL, or both, are affected. In addition, disclosed are methods for enhancing LDL binding to a cell, the method comprising contacting, mixing or associating the cell with one or more of the disclosed synthetic apolipoprotein E-mimicking peptides whereby plasma Lp(a) is affected.

Also disclosed are methods comprising administering the disclosed synthetic apolipoprotein E-mimicking peptides to a subject, whereby plasma LDL, plasma VLDL, or both, are affected, wherein binding of LDL to a cell of the subject is enhanced, degradation of LDL by a cell of the subject is increased, LDL cholesterol in the subject is lowered, binding of VLDL to a cell of the subject is enhanced, degradation of VLDL by a cell of the subject is increased, VLDL cholesterol in the subject is lowered, total plasma concentration of cholesterol in the subject is lowered and/or plasma Lp(a) is lowered.

Also disclosed are methods for enhancing LDL binding to a cell, the method comprising contacting, mixing or associating the cell with one or more of the disclosed synthetic apolipoprotein E-mimicking peptides, thereby allowing the polypeptide to bind the LDL and enhance LDL binding and/or uptake with the associated cell. Also provided is a method for enhancing LDL and VLDL binding to a cell in a subject, the method comprising administering one or more of the disclosed synthetic apolipoprotein E-mimicking peptides, or a composition thereof, to the subject in an amount effective to increase LDL and VLDL binding to the cell of the subject. Also disclosed is a method for treating a subject with a "Lipid Disorder", the method comprising administering to the subject an effective amount of the disclosed synthetic apolipoprotein E-mimicking peptides, or a composition thereof. Also disclosed is a method for reducing serum cholesterol in a subject, the method comprising administering to the subject an effective amount of the disclosed synthetic apolipoprotein E-mimicking peptides, or a composition thereof In the methods described herein, the synthetic apolipoprotein E-mimicking peptide can be administered as a composition comprising the synthetic apolipoprotein E-mimicking peptide and a pharmaceutically acceptable carrier.

Administration of an effective amount of the disclosed synthetic apolipoprotein E-mimicking peptides, or a composition thereof can enhance binding of LDL to a cell, increase degradation of LDL by a cell of the subject, lower LDL cholesterol in the subject, enhance binding of VLDL to a cell of the subject, increase degradation of VLDL by a cell of the subject, lower VLDL cholesterol in the subject, and/or lower total plasma concentration of cholesterol in the subject.

Subjects for the disclosed methods can have coronary artery disease, rheumatoid arthritis, systemic lupus artherosclerosis, coronary, dysbetalipoproteinemia, and/or myocardial infarction. Subjects for the disclosed methods can also or alternatively have inflammatory Bowel Disease (IBD), systemic lupus erythematosus, Hashimoto's disease, rheumatoid arthritis, graft-versus-host disease, Sjögren's syndrome, pernicious anemia, Addison disease, scleroderma, Goodpasture's syndrome, ulcerative colitis, Crohn's disease, autoimmune hemolytic anemia, sterility, myasthenia gravis, multiple sclerosis, Basedow's disease, thrombopenia purpura, allergy; asthma, atopic disease, arteriosclerosis, myocarditis, cardiomyopathy, glomerular nephritis, hypoplastic anemia, and rejection after organ transplantation.

The invention also provides a method for treating a subject with coronary artery disease or any disease or condition associated with increased serum cholesterol. In this method, an amount of the polypeptide of the invention, or a composition thereof, is administered to the subject in an amount to effectively enhance cellular uptake of serum cholesterol in the subject and thereby treat the coronary artery disease or other associated disease in the subject. For example, the associated disease or condition can be dysbetalipoproteinemia, high blood pressure, atherosclerosis, angina, etc. Diseases or conditions associated with increased serum cholesterol would be well known to one of ordinary skill in the art.

In addition, the invention provides for a method for reducing the risk of myocardial infarction in a subject. In this method, an amount of the polypeptide of the invention, or a composition thereof, is administered to the subject in an amount effective to increase cellular uptake of serum cholesterol in the subject, to thereby treat the subject and reduce risk of myocardial infarction. The invention also provides a method for treating atherosclerosis in a subject, where an effective amount of the composition of the invention is administered to subject to increase cellular uptake of serum cholesterol and to thereby treat the atherosclerosis in the subject. The invention also provides for the use of the polypeptide of the invention for the making of a composition of the invention, for example, to treat a disease associated with increased serum cholesterol in a subject or to reduce LDL and/or VLDL serum levels in a subject. The invention also provides for the use of the polypeptide of the invention for enhancing HDL function, the methods comprising contacting the cell with the disclosed synthetic apolipoprotein E-mimicking peptides.

The invention also provides for the use of the polypeptide of the invention for decreasing inflammation, the methods comprising contacting the cell with the disclosed synthetic apolipoprotein E-mimicking peptides, wherein the peptides remove the lipid hydro-peroxides from the plasma by increasing paraoxanase. Also disclosed are methods for increasing plasma paraoxonase (PON-1) activity, the methods comprising contacting the cell with the disclosed synthetic apolipoprotein E-mimicking peptides. Also disclosed are methods for inhibiting atherogenesis, the methods comprising contacting the cell with the disclosed synthetic apolipoprotein E-mimicking peptides.

Also disclosed are methods for inhibiting atherogenesis, the methods comprising contacting the cell with the disclosed synthetic apolipoprotein E-mimicking peptides, wherein plasma cholesterol levels are decreased and HDL function s increased. Also disclosed are methods for removing atherogenic lipoproteins from vessel walls, the methods comprising contacting the cell with the disclosed synthetic apolipoprotein E-mimicking peptides. Also disclosed are methods for decreasing in the atherogenicity of LDL, the methods comprising contacting the cell with the disclosed synthetic apolipoprotein E-mimicking peptides Numerous population and animal studies have established the atheroprotective properties of HDLs. In addition to its main atherogenic property of extracting cholesterol from peripheral cells and transferring it to the liver for excretion (reverse cholesterol transport, also referred to as RCT), HDL also poseeses anti-inflammatory and antioxidant properties. Observations that direct infusion of apolipoprotein A-I in animal models inhibits progression of antiatherosclerotic plaque and, in particular, recent studies with reconstituted forms of HDL in humans demonstrating both a benefit on endothelial function and regression of atherosclerotic burden. It has been shown that apoA-I mimicking peptides result in the reduction in atherosclerotic lesion formation in atherosclerosis-sentsitive mouse models despite no change in cholesterol levels. This occurs via the formation of preβ-HDL-like particles that possess increased paroxonase-1 (PON-1) activity which are able to destroy lipid hydroperoxides (LOOH) and enhance reverse cholesterol transport, the main antiatherogenic properties described for human apoA-I.

Disclosed herein are methods comprising administering the disclosed synthetic apolipoprotein E-mimicking peptides to a subject, whereby plasma HDL is affected. Also disclosed herein are methods comprising administering the disclosed synthetic apolipoprotein E-mimicking peptides to a subject, whereby plasma HDL function is increased. Also disclosed are methods comprising administering the disclosed synthetic apolipoprotein E-mimicking peptides to a subject, whereby plasma HDL is affected, wherein the synthetic apolipoprotein E-mimicking peptide is administered as a composition comprising the synthetic apolipoprotein E-mimicking peptide and a pharmaceutically acceptable carrier. Also disclosed are methods comprising administering the disclosed synthetic apolipoprotein E-mimicking peptides to a subject, whereby plasma HDL is affected, wherein PON activity is increased, lipid hydroperoxides are cleared, atherogenic lipoproteins levels are reduced in the plasma, endothelial function is improved, and/or atherogenic lipoproteins are removed from the vessel wall. Also disclosed are methods comprising administering the disclosed synthetic apolipoprotein E-mimicking peptides to a subject, whereby plasma HDL is affected, wherein the subject has Inflammatory Bowel Disease (IBD), systemic lupus erythematosus, Hashimoto's disease, rheumatoid arthritis, graft-versus-host disease, Sjögren's syndrome, pernicious anemia, Addison disease, scleroderma, Goodpasture's syndrome, ulcerative colitis, Crohn's disease, autoimmune hemolytic anemia, sterility, myasthenia gravis, multiple sclerosis, Basedow's disease, thrombopenia purpura, allergy; asthma, atopic disease, arteriosclerosis, myocarditis, cardiomyopathy, glomerular nephritis, hypoplastic anemia, and rejection after organ transplantation.

Also disclosed are methods for treating a subject with an "Inflammatory Disorder", the method comprising administering to the subject an effective amount of the disclosed synthetic apolipoprotein E-mimicking peptides, or a composition thereof. Also disclosed are methods for treating a subject with an "Inflammatory Disorder", the methods comprising administering to the subject an effective amount of the disclosed synthetic apolipoprotein E-mimicking peptides, or a composition thereof, wherein the synthetic apolipoprotein E-mimicking peptide is administered as a composition comprising the synthetic apolipoprotein E-mimicking peptide and a pharmaceutically acceptable carrier. Also disclosed are synthetic apolipoprotein E-mimicking peptides consisting of a receptor binding domain of apolipoprotein E and a lipid-associating peptide, wherein said receptor binding domain is covalently linked to said lipid-associating peptide in a domain switched orientation. Subjects may be a mammal, such as a human. In another embodiment, the subject is an animal which can be a model system used to test human therapeutics. Non-limiting examples of such animals include dog, pig, primate, murine, feline, bovine, or equine animals.

For delivery of the nucleic acids of the invention to a cell, either in vitro or in vivo, a number of direct delivery systems can be used. These include liposome fusion, gene gun injection, endocytosis, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject. Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Therapeutic Uses

In general, when used for treatment, the therapeutic compositions may be administered orally, parenterally (e.g., intravenously or subcutaneous administration), by intramuscular injection, by intraperitoneal injection, transdermally, extracorporeally, by intracavity administration, transdermally, or topically or the like, including topical intranasal administration or administration by inhalant. The topical administration can be ophthalmically, vaginally, rectally, or intranasally. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disorder being treated, the particular nucleic acid or vector used, its mode of administration and the like. An appropriate amount for a particular composition and a particular subject can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. Parenteral administration includes use of a slow release, a time release or a sustained release system such that a constant dosage is maintained.

Effective dosages and schedules for administering the compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter-indications. Dosage can vary, and can be administered in one or more dose administrations daily, for one or several days. Guidance can be found in the literature for appropriate dosages for given classes of pharmaceutical products. For example, disclosed are methods comprising administering one or more of the disclosed synthetic apolipoprotein E-mimicking peptides to a subject, whereby plasma LDL, plasma VLDL, or both, are affected, wherein said synthetic apolipoprotein E-mimicking peptide is administered in an amount of about 0.01 mg/kg to about 5 mg/kg.

Following administration of a disclosed composition, such as a synthetic apolipoprotein E-mimicking peptide, for treating, inhibiting, or preventing artherosclerosis, the efficacy of the therapeutic peptide can be assessed in various ways well known to the skilled practitioner. For instance, one of ordinary skill in the art will understand that a composition, such as a peptide, disclosed herein is efficacious in treating or inhibiting artherosclerosis in a subject by observing that the composition reduces cholesterol, LDL, or VLDL levels or reduces the amount of cholesterol present in an assay, as disclosed herein. The compositions that inhibit increased cholesterol levels, LDL levels, VLDL levels artherosclerosis, or embolus formation as disclosed herein may be administered prophylactically to patients or subjects who are at risk for artherosclerosis, stroke, myocardial infarction, or embolus formation.

The peptides, polypeptides, nucleic acids, antibodies, vectors and therapeutic compositions of the invention can be combined with other well-known therapies and prophylactic vaccines already in use. The compositions of the invention can be used in combination with drugs used to stabilize the patient and limit damage to the heart. Such drugs include thrombolytics, aspirin, anticoagulants, painkillers and tranquilizers, beta-blockers, ace-inhibitors, nitrates, rhythm-stabilizing drugs, and diuretics. Drugs that limit damage to the heart work only if given within a few hours of the heart attack. Thrombolytic drugs that break up blood clots and enable oxygen-rich blood to flow through the blocked artery increase the patient's chance of survival if given as soon as possible after the heart attack. Thrombolytics given within a few hours after a heart attack are the most effective. Injected intravenously, these include anisoylated plasminogen streptokinase activator complex (APSAC) or anistreplase, recombinant tissue-type plasminogen activator (r-tPA), and streptokinase. The compositions of the invention can be combined with any of these drugs. The combination of the peptides of the invention can generate an additive or a synergistic effect with current treatments.

The peptides, polypeptides, nucleic acids, antibodies, vectors and therapeutic compositions of the invention can also be used in the treatment of a condition selected from the group consisting of atherosclerotic plaque formation, atherosclerotic lesion formation, myocardial infarction, stroke, congestive heart failure, arteriole function, arteriolar disease, arteriolar disease associated with aging, arteriolar disease associated with Alzheimer's disease, arteriolar disease associated with chronic kidney disease, arteriolar disease associated with hypertension, arteriolar disease associated with multi-infarct dementia, arteriolar disease associated with subarachnoid hemorrhage, peripheral vascular disease, chronic obstructive pulmonary disease (COPD), emphysema, asthma, idiopathic pulmonary fibrosis, pulmonary fibrosis, adult respiratory distress syndrome, osteoporosis, Paget's disease, coronary calcification, rheumatoid arthritis, polyarteritis nodosa, polymyalgia rheumatica, lupus erythematosus, multiple sclerosis, Wegener's granulomatosis, central nervous system vasculitis (CNSV), Sjogren's syndrome, scleroderma, polymyositis, AIDS inflammatory response, bacterial infection, fungal infection, viral infection, parasitic infection, influenza, avian flu, viral pneumonia, endotoxic shock syndrome, sepsis, sepsis syndrome, trauma/wound, organ transplant, transplant atherosclerosis, transplant rejection, corneal ulcer, chronic/non-healing wound, ulcerative colitis, reperfusion injury (prevent and/or treat), ischemic reperfusion injury (prevent and/or treat), spinal cord injuries (mitigating effects), cancers, myeloma/multiple myeloma, ovarian cancer, breast cancer, colon cancer, bone cancer, osteoarthritis, inflammatory bowel disease, allergic rhinitis, cachexia, diabetes, Alzheimer's disease, implanted prosthesis, biofilm formation, Crohns' disease, dermatitis, acute and chronic, eczema, psoriasis, contact dermatitis, scleroderma, Type I Diabetes, Type II Diabetes, juvenile onset diabetes, prevention of the onset of diabetes, diabetic nephropathy, diabetic neuropathy, diabetic retinopathy, erectile dysfunction, macular degeneration, multiple sclerosis, nephropathy, neuropathy, Parkinson's Disease, peripheral vascular disease, and meningitis.

In certain embodiments the disclosed compostions can be administered in conjunction with a drug selected from the group consisting of CETP inhibitors, FTY720, Certican, DPP4 inhibitors, Calcium channel blockers, ApoA1 derivative or mimetic or agonist, PPAR agonists, Steroids, Gleevec, Cholesterol Absorption blockers (Zetia), Vytorin, Any Renin Angiotensin pathway blockers, Angiotensin II receptor antagonist (Diovan etc), ACE inhibitors, Renin inhibitors, MR antagonist and Aldosterone synthase inhibitor, Beta-blockers, Alpha-adrenergic antagonists, LXR agonist, FXR agonist, Scavenger Receptor B1 agonist, ABCA1 agonist, Adiponectic receptor agonist or adiponectin inducers, Stearoyl-CoA Desaturase I (SCD1) inhibitor, Cholesterol synthesis inhibitors (non-statins), Diacylglycerol Acyltransferase I (DGAT1) inhibitor, Acetyl CoA Carboxylase 2 inhibitor, PAI-1 inhibitor, LP-PLA2 inhibitor, GLP-1, Glucokinase activator, CB-1 agonist, AGE inhibitor/breaker, PKC inhibitors, Anti-thrombotic/coagulants: Aspirin, ADP receptor blockers, e.g., Clopidigrel, Factor Xa inhibitor, GPIIb/IIIa inhibitor, Factor VIIa inhibitor, Warfarin, Low molecular weight heparin, Tissue factor inhibitor, Anti-inflammatory drugs: Probucol and derivative, e.g., AGI-1067, etc., CCR2 antagonist, CX3CR1 antagonist, IL-1 antagonist, Nitrates and NO donors, and Phosphodiesterase inhibitors.

The invention will be further described with reference to the following examples;

however, it is to be understood that the invention is not limited to such examples. Rather, in view of the present disclosure that describes the current best mode for practicing the invention, many modifications and variations would present themselves to those of skill in the art without departing from the scope and spirit of this invention. All changes, modifications, and variations coming within the meaning and range of equivalency of the claims are to be considered within their scope.

Equivalents

Those skilled in the art will recognize, or be able to ascertain, using no more than routine experimentation, numerous equivalents to the specific embodiments described specifically herein. Such equivalents are intended to be encompassed in the scope of the following claims.

EXAMPLES

An ideal treatment for atherosclerosis would involve rapid clearance of plasma cholesterol and inhibition of inflammatory pathways (Navab, M., et al., J. Lipid Res., 45:993-1007 2004; Swertfeger, D. K. et al., Frontiers in BioSci. 6:526-535 2001). While apolipoprotein (apo) E, the protein component of very low density lipoproteins (VLDL) is involved in the rapid clearance of atherogenic apo B-containing lipoproteins, high density lipoproteins (HDL) and apolipoprotein A-I (apo A-I), the major protein component of HDL has been shown to exhibit anti-inflammatory properties. Since bringing down low density lipoprotein (LDL) levels has yielded only approximately 30% reduction in cardiovascular risk, the next targets against cardiovascular diseases appear to be HDL and apo A-I. Increasing HDL levels by the inhibition of cholesterol ester transfer protein appeared to increase HDL, apparently without improvement in HDL function, indicating that presence of functional HDL is more important than HDL levels.

Recent advances in the apo A-I mimetic peptides indicate a possibility to improve HDL functions (Shah, P. K. et al. Trends Cardiovasc. Med. 15:291-296, 2005). This examples described below provide ways of incorporating properties to lower plasma apo B-containing lipoprotein to apo A-I mimetic peptides, to obtain peptides with dual functions. As such, novel peptides that possess cationic putative receptor binding domain from apo E that is covalently linked to the active apo A-I mimetic peptide to yield a dual-domain peptide Ac-hE-18A-NH$_2$ (SEQ ID NO: 12) in which residues 141-150 of apo E (LRKLRKRLLR) is linked to 18A (a baseline class A amphipathic helical peptide) were designed. Also designed was a single cationic domain peptide to which the lipid hydroperoxide scavenging properties of apo A-I mimetics were incorporated. This peptide, R18L-2Y (SEQ ID NO: 62; with the sequence Ac-GFRRFLGSWARIYRAFVG-NH$_2$) when folded as an α-helix, possesses Arg at the polar face and the center of the hydrophobic face possesses aromatic residue in π-electron cluster, capable of scavenging lipid hydroperoxides (Datta, G. et al. J. Biol. Chem. 279: 26509-26517, 2004). Cationic Arg rich domains are thought' to associate with ubiquitous cell surface heparin sulfate proteoglycans (HSPG). Results show that both of these peptides enhance uptake of atherogenic lipoproteins in HepG2 cells, clear plasma cholesterol in dyslipidemic mouse models and they also appear to improve HDL function. Results also show that these two candidate peptides also inhibit atherosclerosis in apo E null mice. Previous results show that Ac-hE18A-NH$_2$ (SEQ ID NO: 12) dramatically decreases plasma cholesterol in different dyslipidemic mouse models (Datta, G. et al. Biochemistry 39:213-220 2000; Anantharamaiah, et al A-I and E. Curr. Sci. 80:11-20 2001; Datta, G. et al. J. Lipid Res. 42:959-966 2001; Ramprasad, M. P. et al. J. Controlled release 79:207-218 2002; Garber, D. W. et al. Atherosclerosis. 163:229-237 2003), and in WHHL rabbits Garber, (D.W. et al. Atherosclerosis. 163:229-237 2003).

Further results indicate that this peptide possesses anti-inflammatory properties. This occurs through a lowering of plasma lipid hydroperoxide levels concomitant with a significant increase in the plasma paraoxonase (PON-1) activity. In the WHHL model, the LDL-R pathway is compromised, thus the accelerated atherogenic lipoprotein clearance is likely via the cell surface HSPG-mediated pathway, as described earlier in murine models (Garber, D. W. et al. Atherosclerosis. 163: 229-237 2003). In a second model of atherosclerosis, the New Zealand white (NZW) rabbits fed an atherogenic diet, a single intravenous administration (3 mg/kg) of the peptide significantly decreased total plasma cholesterol levels for 15 days. En face analysis of the lesions after 50 days showed ~50% lesion coverage in the saline-treated rabbits (control), while little to no lesion in the peptide-treated animals. Furthermore, in vitro studies in HepG2 cells demonstrated that dual domain peptides specifically increased secretion of apo-A-I and apo E. In vitro studies have also shown that the dual-domain cationic peptides are recycled. The dual domain peptides also enhance the secretion of pre-β HDL like apo A-I-containing particles, and the effect lasts for more than 72 hrs (perhaps due to recycling dual domain cationic peptides), suggesting that the chronic cholesterol-lowering effect of peptide in different animal models can be related to enhanced secretion of hepatic apoA-I in preβ-HDL form, thus increasing the "functional HDL" levels.

Example 1

Effect of Cationic Dual-domain Peptides on Atherogenic Lipoprotein Uptake

The effect of the peptide Ac-LRKLRKRLLR-18A-NH$_2$ (Ac-hE18A-NH$_2$; SEQ ID NO: 12) in HepG2 cells and in dyslipidemic mouse models has been previously described (5, 6, 7, 8, 9). These studies demonstrated that the peptide Ac-hE-18A-NH$_2$ (and not LRKLRKRLLR or Ac-18A-NH$_2$) associates with atherogenic apo B-containing lipoproteins in human plasma. It was also shown that the peptide is able to enhance the uptake and degradation of LDL and VLDL in HepG2 cells Datta, G. et al. Biochemistry 39:213-220 2000). Preliminary results have shown that LDL-receptor was not involved in the clearance of plasma cholesterol. In dyslipidemic mouse models, studies showed that the peptide is able to associate with apo B48-containing lipoproteins and enhance their uptake and degradation (Datta, G. et al. Biochemistry 39:213-220 2000). In C57BL6 mice fed an atherogenic diet, apo E null mice, apo E(null)-LDL-R(null) double knockout mice, atherogenic lipoproteins LDL and VLDL contained mostly apo B-48 and less of apo B-100. In experiments where atherogenic lipoprotein reduction was observed, the peptide did not reduce HDL levels, as studied by column lipoprotein profile (CLiP) (Datta, G. et al. J. Lipid Res. 42:959-966 2001; Garber, D. W. et al. Atherosclerosis. 163: 229-237 2003).

Example 2

Ac-hE-18A-NH$_2$ Inhibits Atherosclerosis in Apo E Null Mice

Figure 2:
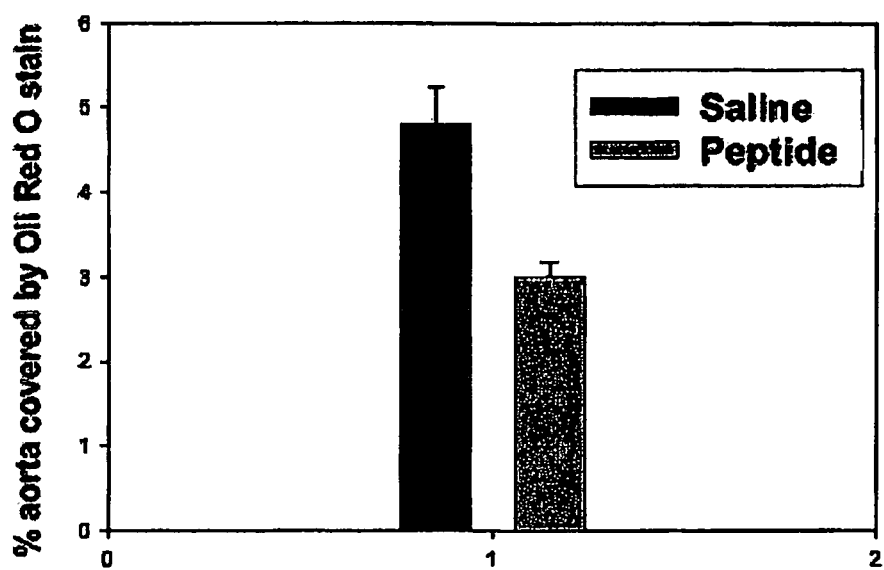
FIG. 2 shows the effect of Ac-hE18A-NH$_2$ (i.v.-administration) for 4 weeks in apo E knock-out mice (16 weeks) on lesion formation. Extent of lesion is analyzed by en face preparation and staininf with Oil Red O.

Atherosclerosis inhibition studies in apo E null mice that develop atherosclerosis spontaneously were also performed. Retroorbital administration of Ac-hE-18A-NH$_2$ (50 µg/mouse, 3 times weekly) for four weeks into sixteen week old female apo E null mice showed decreased lesion by 40% (p value <0.001) compared to the control group (n=11 in control and n=12 in peptide administered group). In this administration procedure, there was no loss of animals and no visible injury to animals was observed, despite multiple administration (of a total of 12 administrations). Lesion analysis was performed using the en face preparations. Sixteen week old mice would have well established lesions. These results (FIG. 2) show that the peptide is able to inhibit lesion formation in apo E null mice. These results are in agreement with the peptide being antiatherogenic. Detailed studies on the mechanism of the inhibition of atherosclerosis are described below.

Example 3

Figure 3:
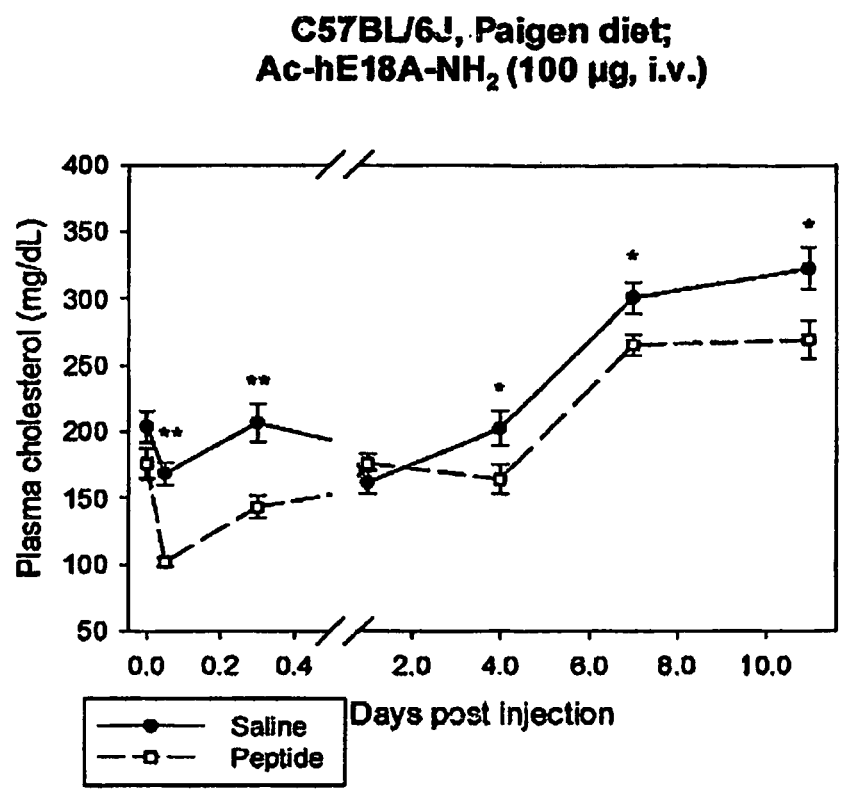
FIG. 3 shows the long-term effect of one-time administration of Ac-hE-18A-NH$_2$ (n=9 in each group). An initial reduction in plasma cholesterol is followed by cholesterol levels coming back to original values at 24 h. A significant decrease was observed at 4-days and was maintained for 8 days.
Figure 4:
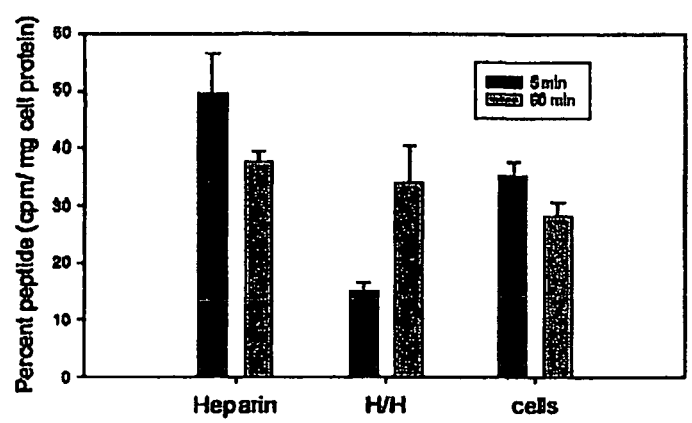
FIG. 4 shows HepG2 cells that were incubated with $^{125}$I-Ac-hE18A-NH$_2$ for 5 minutes and 60 mintues and the peptide releasable by heparin and heparinase/heparitinase (H/H) determined. The percent of peptide released by H/H after 60 min incubation is more than that observed at 5 min while there is less peptide in the cells.

It has been shown that a portion of apo E on triglyceride-rich lipoproteins, as well as on HDL is internalized and recycled (Swift, L. L. et al., J. Biol. Chem. 276:22965-22970 2001; Farkas, M. H. et al., J. Lipid Res. 45: 1546-1554 2004). Liver cells can internalize apo E which is eventually re-released. Administration (i.v) of 100 µg of the peptide Ac-hE-18A-NH$_2$ in to C57BL/6J mice (n=9 in each group) fed an atherogenic diet showed a biphasic effect on plasma cholesterol levels. Initially peptide decreased plasma cholesterol by >65%. Lower total cholesterol levels were observed even after 8 days in the peptide administered group compared to the control group despite continued atherogenic diet administration (FIG. 3). Effect on plasma cholesterol is seen even after the disappearance of the peptide from plasma. It is possible that the apo E-mimetic peptide is recycled. To understand the mechanism by which the peptide is able to exert such a dramatic effect, the effects of the peptide on Hep G2 cells for 1) peptide bioavailability and 2) effect on HDL and apo A-I were examined. To do so, HepG2 cells were grown in MEM medium containing 10% FCS. At 85% confluency, the cells were washed and MEM medium containing 10% LPDS was added. The cells were incubated for 5 min and 60 min with $^{125}$I-labeled Ac-hE-18A-NH$_2$ (10 jtg/ml) and with 1$^{25}$ I-labeled Ac-hE-18A-NH$_2$ (10 tjg/ml)+LDL (10 tjg/ml). At the end of the incubation time period the medium was removed and the cells washed 3 times with TBA containing BSA and twice with TBA. The cells were then incubated with buffer containing heparin at 4° C. for 1 h. The cells were then treated with heparinase and heparitinase for 1 h at 37° C. The heparin wash and the heparinase/heparitinase wash were counted. The cells were aspirated in 0.1 N NaOH and counted. All the experiments were done in triplicate and the counts expressed as a percentage of the total counts. FIG. 4 shows that more counts are seen in the media at 60 min after heparinase/heparitinase wash, and correspondingly fewer counts in the cells at 60 min. These results indicate that the peptide remains intact on the cell surface. These results are similar to what has been observed for apo E, which is known to be involved in recycling (Swift, L. L. et al., J. Biol. Chem. 276:22965-22970 2001; Farkas, M. H. et al., J. Lipid Res. 45: 1546-1554 2004).

Example 4

Inhibition of Atherosclerosis

Figure 5:
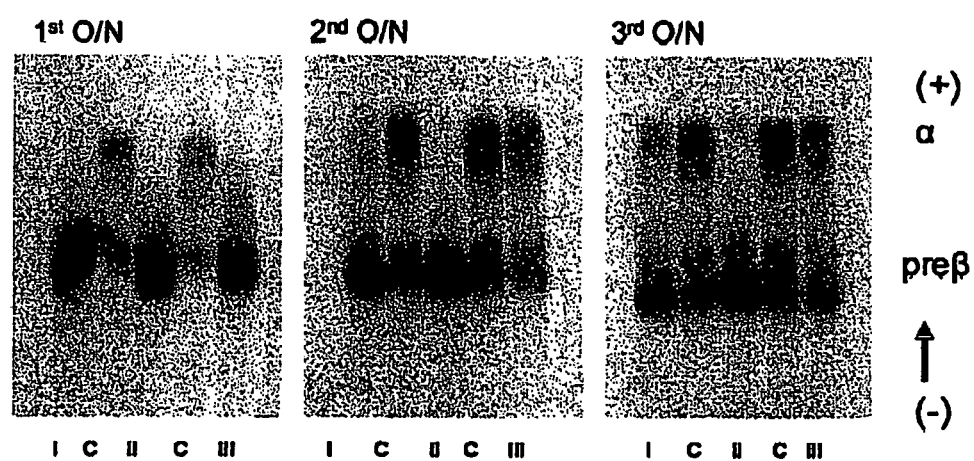
FIG. 5 shows Apo A-I secretion of HepG2 cells treated with peptides: Ac-hE-4F-NH$_2$ (I), Ac-hE-18A-NH$_2$(III), and 4F(II), at 24, 48 and 72 h time points: Cells grown to confluency, and treated with peptide (50 µg/ml), in media without FBS. Media containing peptide was removed after 1$^{st}$ O/N incubation, and replaced with media (without peptide) w/o FBS. After the 2$^{nd}$ O/N incubation, media was removed and replaced with media w/o FBS, and incubated for the third and final night. Agarose gels were run for each time point. Western blots were performed for human Apo A-I, to determine the distribution of preβ-HDL particles. C=control cells without peptide. These results show that the peptide has effect for a longer period since it is internalized and re-released.

It has been observed with an apo A-I-mimetic peptide that the peptide is able to increase HDL and apo A-I levels in mice infected with influenza virus (Van Lenten, B. J. et al., Circulation. 106(9):1127-32, 2002). In HepG2 cells (Dashti, N. et al, J. Lipid Res. 45:1919-1928, 2004), and other mouse models it has been shown that the peptide improves the atheroprotective capacity of HDL (Anantharamaiah, G. M. et al, A-I and E. Curr. Sci. 80:11-20 2001). The peptide 4F (SEQ ID NO: 17) with π-electrons at the center of the nonpolar face, is able to form its own particle which can recruit apo A-I and PON and thus exert antiatherogenic effects. The peptide has also been shown to stabilize ABCA1, the membrane protein that is involved in nascent discoidal HDL synthesis. The possible effect of Ac-hE-18A-NH$_2$ on HepG2 cells was also investigated. In light of previous observations with class A peptides, the effect of three peptides in the formation of HDL-like particles was studied. As shown in FIG. 5, compared to the supernatant from control cells, supernatants from peptide-treated cells show a marked increase in HDL, that is smaller in size as seen by non-denaturing gradient electrophiresis, is similar to preβ-HDL. Incubation of equal amount of Ac-hE-18A-NH$_2$ (SEQ ID NO: 12), Ac-hE-4F-NH$_2$ (SEQ ID NO: 63), and 4F (SEQ ID NO: 17) (on weight basis) with HepG2 cells produced preβ-HDL (FIG. 5). While the amount preβ-HDL decreased with 4F in the second overnight incubation, to levels similar to that of control cell medium, even after second and third overnight incubation with fresh cell medium, the other two cationic peptides produced significant amounts pre3j HDL. These results support that the dual-domain peptides perhaps due to recycling phenominon, possess properties to secrete preβ-HDL particles much longer than class A peptides, thus explaining the chronic antiatherogenic and anti-inflammatory effects of these peptides.

Example 5

Effect on Inflammatory Pathways

Figure 6:
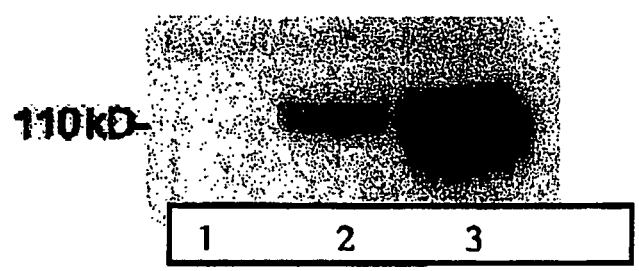
FIG. 6 shows a Western blot for VCAM expression. HUVECs were challenged with the peptide alone, peptide +LPS and LPS. LPS induces expression of VCAM-1 (lane 3). Peptide by itself (lane 1) does not show any adverse effect, while it inhibits the expression of VCAM-1 induced by LPS by more than 80% (lane 2). These results indicate that the peptide has an anti-inflammatory effect.

The effect of the peptide on the inflammatory response of bacterial lipopolysaccharide (LPS), a potent inducer of cytokines and cell adhesion molecules was also examined. FIG. 6 shows the inhibitory effect of Ac-hE-18A-NH$_2$ on LPS-induced VCAM-1 expression in human umbilical vein endothelial cells (HUVEC). Coincubation of HUVECs with LPS (1 μg/ml, 6 h exposure) and Ac-hE-18A-NH$_2$ (50 μg/ml) showed more than 80% inhibition (lane 2, FIG. 6). As shown in FIG. 6, the present results show that monocyte chemotaxis protein-1 (MCP-1) is also inhibited by the peptide. These results indicate that the antiinflammatory properties of the peptide can be due to either its effect directly on LPS, or the newly secreted apoA-I may be causing the inhibition of LPS effect on HUVECs levels or improved HDL function or both in vivo.

Example 6

Figure 7:
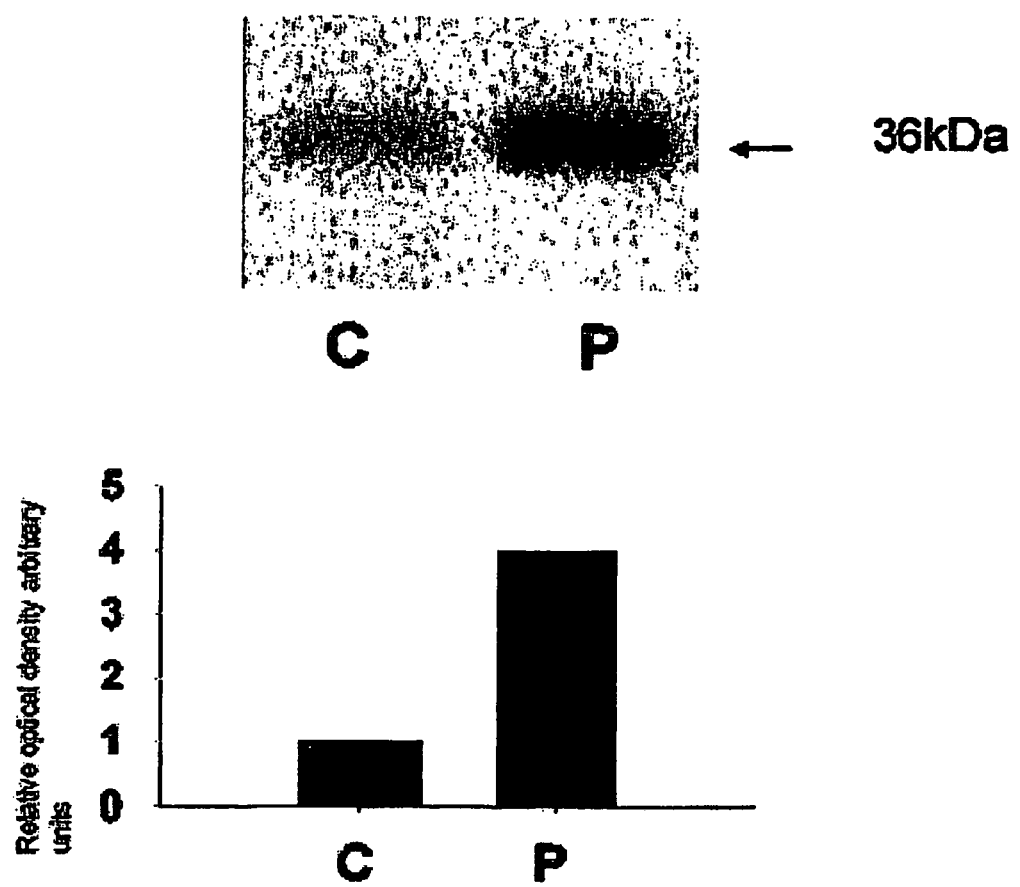
FIG. 7 shows treatment of THP-1 derived macrophages with Ac-hE-18A-NH$_2$ enhances the synthesis of apo E. Cells were metabolically labeled with 35S-methionine, treated with the peptide (25 µg/10$^6$ cells) for 5 h and the medium was subjected to SDS-PAGE. Bands were developed by autoradiography and quantitated by densitometry. These results indicate that the peptide can stimulate apo E synthesis and the chronic effect of the peptide on cholesterol reducing ability and anti-inflammatory ability is partly due to its ability to promote apo E synthesis.

Ac-hE-18A-NH$_2$ Enhances the Secretion of De Novo Synthesized Apo E by Macrophages THP-1 monocyte derived macrophages were metabolically labeled with $^{35}$S-methionine in RPMI medium containing FBS. Macrophages (10$^6$ cells) were treated with the dual-domain peptide (25 tjg/10$^6$ cells) for 5. Conditioned medium was collected and cells were washed with cold PBS. Preparative cocktail containing MEM, plus lupeptin (50 tjg/ml), pepstatin A (50 tjg/ml), and aprotinin (100 kallikrein inactivating units/ml) were added to the medium to preserve oxidative and proteolytic damage. The medium from control cells and peptide-treated medium were concentrated to equal volume and loaded quantitatively on SDS-polyacrylamide gels (4 to 20% PAGE for 2.5 h at 4° C. at 125 volts). The gel was exposed to x-ray film for overnight. Band obtained in the peptide treated cell medium clearly had a band at 36 kDa and the intensity of this band was 4 times more than the band obtained from the medium of control cells, as determined by the densitometry (FIG. 7). Increased de novo synthesis of apo E can enhance the uptake of atherogenic lipoproteins. In addition, apo E has anti-inflammatory properties and properties to enhance cholesterol efflux from macrophages. These properties would prevent macrophages from becoming foam cells. These studies showed that the peptide is turned over very rapidly in vivo and maximum counts in the liver were observed. Thus the peptide would recycle and presence of the peptide would have lasting effect on the production of preβ HDL, increase in the synthesis of de novo apo E, and the peptide would enhance the clearance of atherogenic lipoproteins both directly (perhaps via the HSPG pathway) and indirectly via the increased synthesis of apo E. As presented in FIG. 8, the cationic single domain peptide R18L-2Y (SEQ ID NO: 62) (even as a peptide containing L-amino acids) inhibited atherosclerosis in apo E null mice when orally administered.

In addition to this, it was shown that the peptide is able to stimulate the synthesis of additional antiatherogenic proteins involved in lipoprotein metabolism (FIG. 9). THP-1 derived macrophages were incubated with Ac-hE18A-NH$_2$ for 5 h and overnight (O/N). RNA was extracted from the cells by Trizol (Invitrogen). mRNA levels were determined by real time PCR using SYBR green and appropriate primers for the genes. Results were normalized against GAPDH and expressed as fold increase over control cells (without peptide). These results show that the peptide Ac-hE-18A-NH$_2$ exerts a long-term effect that results in the decrease of not only circulating atherogenic apo B-containing lipoproteins but also exhibits additional effects on shutting down the proatherogenic protein levels and increasing the levels of proteins that may be involved in clearing atherogenic lipoproteins. Thus, the results can be explained by the multiple antiatherogenic and anti-inflammatory effects of this peptide.

Example 7

Although Ac-hE-18A-NH$_2$ enhanced the hepatic uptake and degradation of atherogenic lipoproteins in apo E null mice, dual knockout mice (LDL-R(null)-apo E(null)), and C57BL/6 on an atherogenic diet, the peptide had no effect on the plasma cholesterol levels of C57BL/6 on normal chow, LDL-R(null) on normal chow or on a Western diet. Further investigations showed that n these mouse models (LDL-R (null) and C57BL6 on normal chow), the peptide is not able to associate with B-100-containing particles. However, the peptide is able to associate with human LDL (containing apo B-100) and VLDL and is able to enhance uptake and degradation of atherogenic human lipoproteins in HepG2 cells and in LDL-R (null) mouse model (Garber, D. W. et al. Atherosclerosis. 163:229-237 2003). The reason for the difference in the properties of apo B-100-containing human LDL and mouse LDL is not clear. The difference appears to be in the lipid packing between human LDL and mouse LDL that possess apo B-100. Apo B-100-containing mouse LDL does not allow the binding of the peptide to its surface despite the fact that the peptide possesses exceptionally high exclusion pressure value (48 dynes/cm) (Garber, D. W. et al. Atherosclerosis. 163:229-237 2003).

Figure 10:
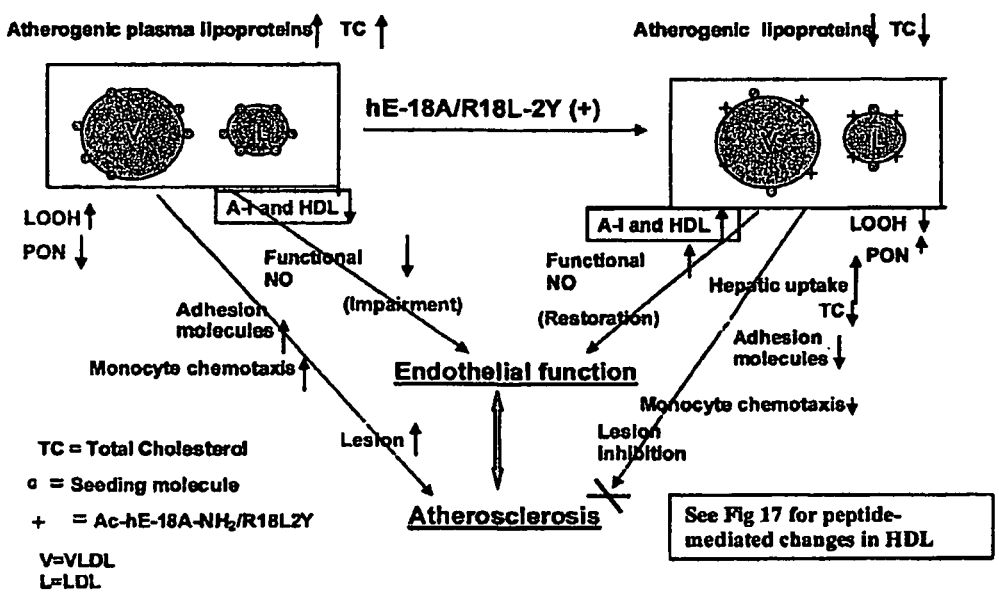
FIG. 10 shows a schematic representation of the proatherogenic effects without administration of one of the disclosed peptides and that one of the disclosed peptides can correct this by an antiinflamatory mechanism.

These observations led to the study summarized in FIG. 9. The peptide Ac-hE-18A-NH$_2$ is able to associate with atherogenic lipoproteins from WHHL rabbits and NZW rabbits on atherogenic diet and enhance their uptake and degradation. Present observations in rabbits show that the peptide is able to improve HDL function and also endothelial function. Endothelial function is closely related to the HDL function. Since HDL function is correlated to CETP function, rabbits are abetter model for studying the scheme shown in FIG. 10. Although CETP expressing mouse model is available, for studying the effect of the peptide, these mice have to be crossed with atherosclerosis-sensitive mouse model (especially on an human apo A-I-expressing mouse model), which by itself would be a separate research project and even then the Gene Fold increase lesions produced in these models differ significantly from the types of human lesions. Since the WHHL rabbit models selected here are close to familial hypercholesterolemia in humans, and dyslipidemia can be produced using different types of diets with varying pathology, the effect of the peptide in two rabbit models was studied. Furthermore, similar to humans rabbits possess CETP which plays an important role in the cholesterol metabolism. Thus, results obtained using the two rabbits described here have a direct relevance to the human atherosclerotic disease Example 8

Effect of the Peptide Administration in WHHL Rabbits

It has been previously demonstrated that a single administration of the peptide Ac-hE-18A-NH$_2$ exerts a dramatic effect on endothelial function and decrease in plasma cholesterol while the control peptides were inactive (Circ. 2005; 111:3112-3118). The peptide associates with LDL from WHHL rabbits, modifies the LDL surface charge and removes lipid hydroperoxides (seeding molecules). Since the peptide did not associate with the plasma LDL from LDL-R (null) mice, a study was developed to determine if the peptide is able to associate with plasma LDL from WHHL rabbits, a model for human hyperlipoprotenemia. 100 µg of the $^{125}$I-labelled peptide was mixed with 1 ml of plasma from 6 month old WHHL rabbit. After incubation for 1 h at room temperature, the plasma was subjected to CLiP analysis (66). Radioactivity in different fractions was determined and plotted on the CLiP profile. The results showed that the peptide associates with LDL, the major class of lipoprotein present in WHHL plasma. The peptide-treated WHHL plasma LDL contains reduced amounts of LOOH compared to plasma from untreated WHIM rabbits. A single bolus (15 mg/kg intravenous) administration of Ac-hE-18A-NH$_2$ not only reduced plasma cholesterol levels from 562±29 mg/dl to 287±22 mg/dl at 18 h, in WHHL rabbits but also significantly improved arterial endothelial function. This improvement was associated with a reduction in 2 markers of oxidative stress. First, the plasma lipid hydroperoxide content was reduced significantly, an effect associated with a 5-fold increase in HDL paraoxonase activity. Second, the formation of superoxide anion, a scavenger of nitric oxide, was also significantly reduced in arteries of these animals Because dyslipidemia and endothelial dysfunction are common features of the atherosclerotic disease process, these unique peptides have ideal composite properties that ameliorate atherosclerosis. With the report on the apoA-IMilanoli$^p$id complex infusion. studies in humans (Nissen, S. E., et al. JAMA 290:2292-2300 2003), interest in HDL-based therapy has increased. Although the results described for apo A-IMilano are significant, due to the amount of protein:lipid complex to be infused (40 mg/kg of protein alone plus phospholipids), the cost of such a treatment is enormous. In this context, the present results show that a single administration of an amphipathic helical peptide is effective in dramatically reducing plasma cholesterol levels and improving endothelial function. Large amounts of peptide can be produced and peptide can be administered without lipid to achieve key contributory factors to antiatherogenic effects in vivo.

Effect of Peptide Administration to NZW rabbits on 1% Cholesterol Diet

The above results indicate that the peptide exerts an effect on atherogenic LDL in enhancing hepatic clearance and also in improving HDL function. It has been shown that very small amounts of D-4F, a class A amphipathic helical peptide, modifies several HDL properties (Navab, M., et al. Circulation 109:3215-3220 2004). D-4F reorganizes HDL to produce "pre-βHDL like" particles that are highly effective in destroying lipid hydroperoxides and thereby enhancing reverse cholesterol transport. NZW rabbits have been studied for hypercholesterolemia and relative LDL and β-VLDL production using diets containing different amounts of cholesterol (Holvoet, P. et al. Arterioscl. Thromb. Vasc. Biol. 17:2376-2382 1997). Thus, with 0.125% (w/w) cholesterol diet, LDL cholesterol levels increase; with 0.5% and higher cholesterol levels in the diet, □-VLDL (containing apo B-100) increases dramatically. These β-VLDL particles contain increased amounts of oxidized lipids, thus enhancing the progression of atherosclerosis (Holvoet, P. et al. Arterioscl. Thromb. Vasc. Biol. 17:2376-2382 1997). To assess the effect of the peptide in this rabbit model, a 1% cholesterol diet fed NZW rabbits were utilized.

Rabbits responding to high cholesterol diet were randomized one week after the start of the diet to select rabbits with similar response (similar amounts of total plasma cholesterol). Ac-hE-18A-NH$_2$ (3 mg/kg) was administered intravenously (i.v.) 15 days after the initiation of the diet and rabbits were continued on high fat diet for the entire study period. After 14 days from the first administration, plasma samples were taken from both the peptide-administered and saline administered (control) rabbits (n=3 in each group). The plasma samples from the peptide administered rabbits were not turbid, whereas the plasma samples from control rabbits were turbid. Significantly decreased amounts of VLDL and LDL were also obvious. The column lipoprotein profiles of representative rabbits from peptide administered group and control show that the atherogenic lipoproteins levels decreased. A second dose of peptide was administered 15 days after the first treatment. Since the cholesterol levels remained low two weeks after the second administration in peptide-administered rabbits, these and saline administered rabbits were sacrificed 51 days after the initiation of the diet. Aorta from the peptide administered and control rabbits were stained with Oil Red O. Aorta from the peptide administered rabbits had 40-50% less lesion than the control rabbit aorta.

Figure 11:
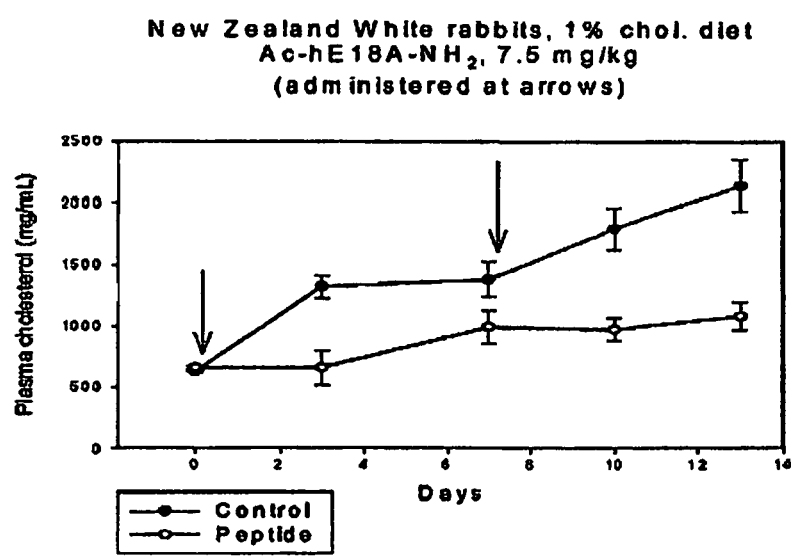
FIG. 11 shows plasma cholesterol levels over time in rabbits administered with Ac-hE18A-NH$_2$. Administration of Ac-hE18A-NH$_2$ to high fat diet administered rabbits with initial cholesterol values in the range of 600 mg/dl (1 week on 1% cholesterol diet). Peptide (5 mg/kg) was iv-administered two times as shown in the figure (n=4). At the end of 14 days (21 days after the initiation of atherogenic diet), while plasma cholesterol levels in the control rabbits were in the range of 2000 mg/dl (n=4), the peptide administered rabbits showed cholesterol values in the range of 1000 mg/dl. A 50% decrease in plasma cholesterol was observed after administration of the peptide.

To see the cumulative effect of the peptide at a shorter interval, a slightly different protocol was utilized. Rabbits with similar levels of plasma cholesterol upon 1% cholesterol diet administration for one week were selected. Peptide (7.5 mg/kg) was i.v. administered in two intervals (first one week after high fat diet initiation and the second a week after the first peptide administration). Plasma cholesterol levels were determined at the time of administration of the peptide, before second administration and a week after second administration. Results demonstrate that in peptide-treated rabbits the plasma cholesterol was 50% less than in the control rabbits at the end of the experiments (FIG. 11). The effect of the peptide on plasma cholesterol levels are observed even after the disappearance of the peptide from circulation (see FIG. 11). Using 3 mg/kg of radiolabelled peptide, turnover studies showed that the plasma clearance of the peptide (FIG. 12) is much faster than that observed in WHHL rabbits. This suggests that the plasma cholesterol lowering continues even after the peptide has disappeared from the plasma compartment.

Figure 12:
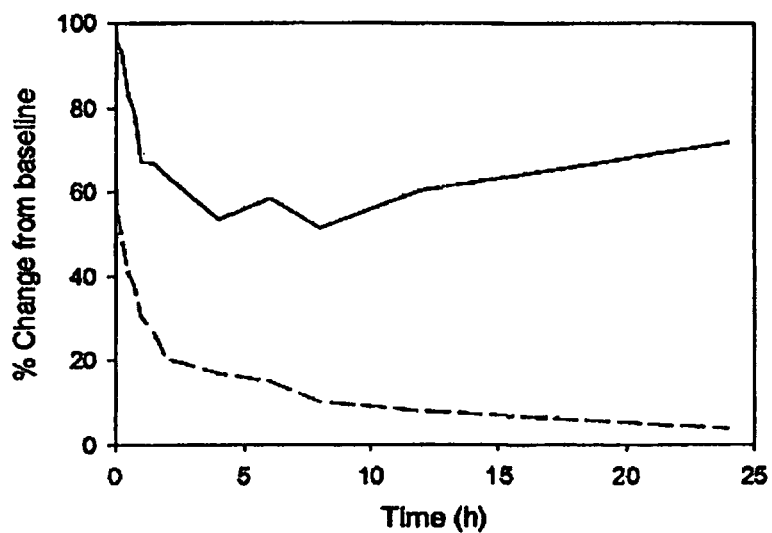
FIG. 12 shows turn over experiments in NZW rabbits fed 1% diet shows initial decreases cholesterol (and the disappearance of peptide) from plasma. Despite the loss of peptide from the plasma, effect of the peptide lasts for 14 days.
Figure 13:
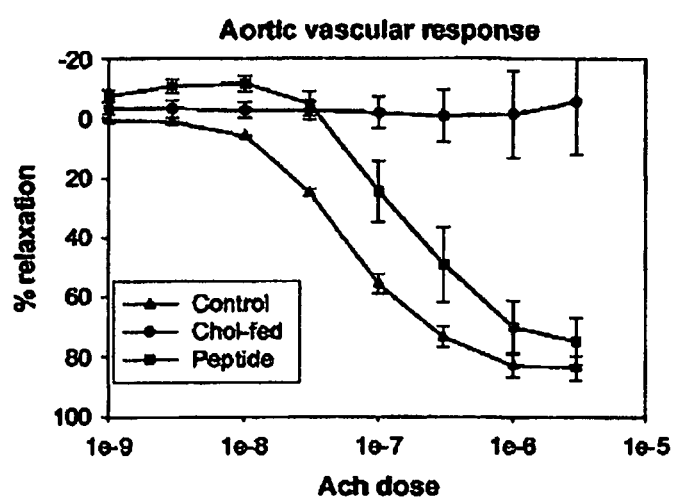
FIG. 13 shows aortal rings in control, atherogenic diet administered and diet-administered with peptide i.v. administered rabbits were studied for endothelial function. While the diet administered rabbit aortal rings did not respond to acetyl choline, aortae from rabbits on high fat diet and peptide-administered rabbits showed dose-dependent relaxation to acetyl choline, almost similar to aortae from normal diet-administered rabbits.

Therefore, possible reasons for the clearance of atherogenic lipoproteins can be in addition to rapid hepatic clearance similar to the properties of apo E, modulation of HDL properties or synthesis of macrophage apo E. If this is true, this peptide may also exert its effect on endothelial function. Indeed it was observed that there is a recovery of endothelial function as studied by the acetylcholine dose-dependent aortal relaxation (FIG. 13). While the control rabbits (with cholesterol levels 2000 mg/dl) after 51 days of the 1% cholesterol diet administration have lost endothelial function completely, the aortal rings from peptide-administered rabbits show vascular response almost similar to aortas obtained from rabbits on a normal diet (FIG. 12). These results indicate that the peptide can act by inhibiting superoxide anion production or by a presently unknown mechanism. It is possible that lipid lowering can cause reduction of oxidative stress and thus inhibition of endothelial activation.

Example 9

The Concept of Single Domain Cationic Peptides, in vitro and in vivo Studies

Figure 14:
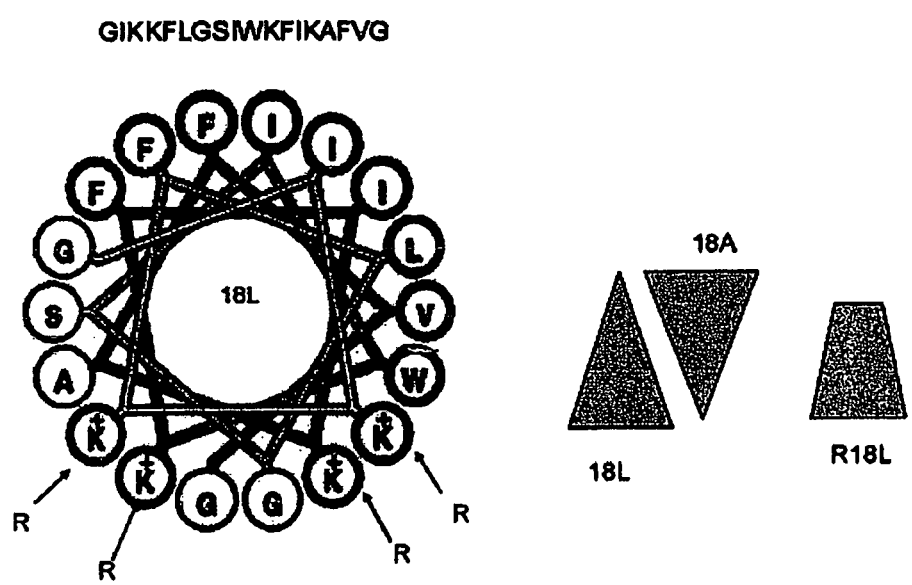
FIG. 14 shows that class A peptides inhibit 18L-induced lysis: Molecular basis for this inhibition is the opposite cross-sectional shape of these molecules. If K in 18 L is replaced by R, lytic activity is reduced to minimum, due to the change in the cross-sectional shape in the peptide R18L to trapezoidal.
Figure 15:
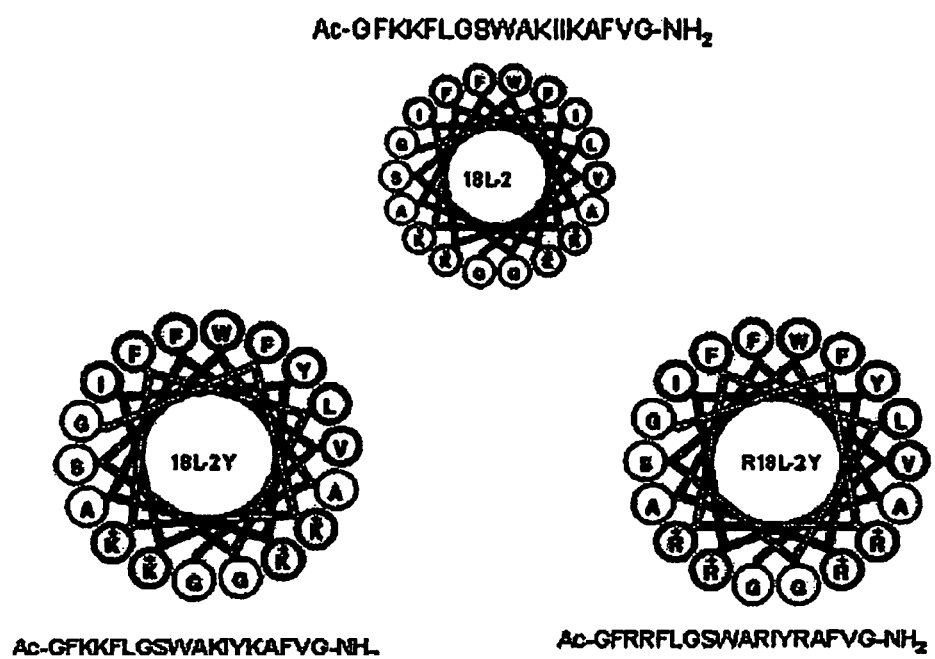
FIG. 15 shows a rational design of R1 8L-2Y to reduce lytic properties and enhance uptake of atherogenic lipoproteins.
Figure 16:
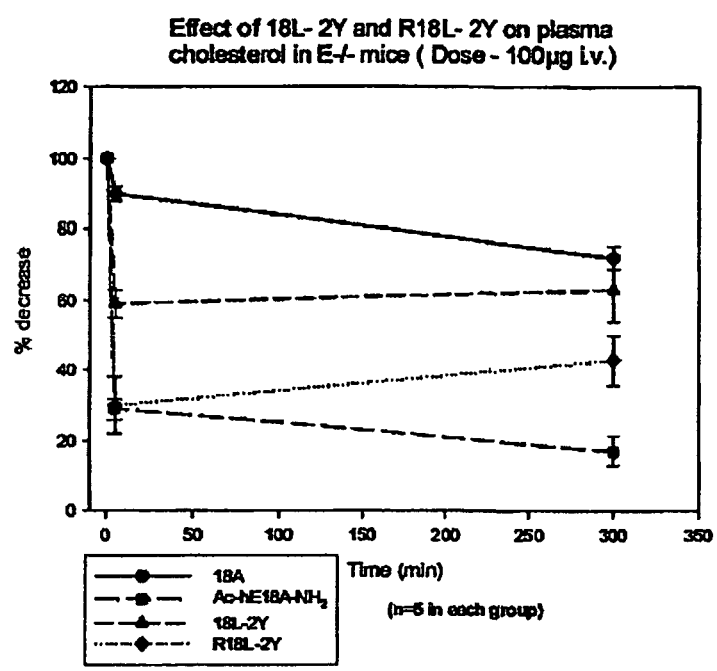
FIG. 16 shows the rationale for selecting R1 8L-2Y for further studies Effect of 18L-2Y and R18L-2Y on plasma cholesterol in E−/− mice (Dose-100 μg i.v.).

Dual domain peptide that has LRKLRKRLLR (SEQ ID NO: 1), a sequence from apo E putative receptor binding domain, covalently linked to 18A (SEQ ID NO: 11) enhances uptake and degradation of apo B-containing lipoproteins. It has been previously shown that a synthetic model lytic peptide (18L, FIG. 14) in the past that is able to lyse red cells (Aikawa, M., et al. Circulation 106:1390-1396 2002). It has also been previously shown that that if the Lys residues are replaced by Arg, compared to the Lys-containing peptide, the resulting Arg-containing peptide has only 2% of lysis (Aikawa, M., et al. Circulation 106:1390-1396 2002). Based on the idea that central aromatic residue cluster at the center of the nonpolar face is able to scavenge lipid hydroperoxides and thus the resulting peptide is able to exhibit anti-inflammatory properties, the original R18L was modified (FIG. 15). Rearrangement of the nonpolar face of 18L to incorporate aromatic residues at the center of the nonpolar face yields 18L-2. Addition of Tyr (for radiolabeling) yields 18L-2Y (FIG. 15). All of the Lys residues changed to Arg results in R18L2Y (FIG. 15). The cholesterol reducing properties of 18L-2Y and R18L-2Y were compared in apo E null mice and these results are shown in FIG. 16. The Arg-containing peptide R18L-2Y possessed increased ability to clear plasma cholesterol compared to 18L-2Y (FIG. 16).

Figure 8:
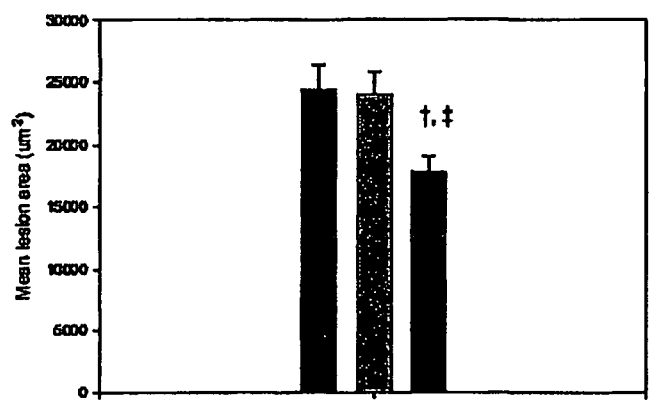
FIG. 8 shows the effect of oral feeding of 18L-2Y and R18L-2Y (1 mg/mouse) for 6 weeks in female apo E ko mice. 4 week old female apo E knock-out mice that were fed with peptides 18L-2Y and R18L-2Y for 6 weeks. The peptides were mixed in normal chow (1 mg/4 g chow) and fed ad libitum. At the end of 6 weeks, the animals were euthanized and the atherosclerotic lesion area was stained with Oil Red O and quantified. n=20 for control (solid black) and 18L-2Y treated group (light grey) and n=23 in R18L-2Y treated group (dark grey). †, p<0.01 vs control (dark) and ‡, p<0.01 vs 18L-2Y.
Figure 17:
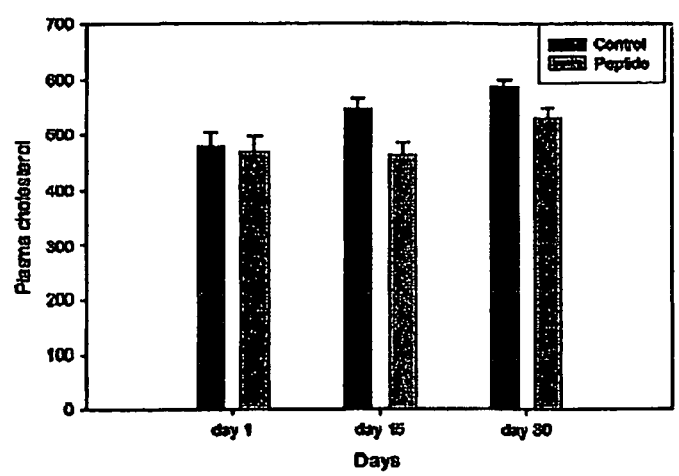
FIG. 17 shows oral administration of R18L-2Y decreases plasma cholesterol in apo E null mice. Peptide, 1 mg/4 g of chow (per animal per day) (apo E−/− mice) lowers plasma cholesterol (1 mg/mouse/day) for 30 days. (n=5 in each group).

It has also been observed that a class A peptide (D-4F) orally administered, inhibits atherosclerosis in apo E null mice, even though the bioavailability of the peptide is only in nanomolar quantities. This takes place in the absence of change in the plasma cholesterol levels. Since the π-electron density cluster has been incorporated to this R18L-2Y peptide and the peptide is able to associate with cell surface proteoglycans due to the presence of positively charged Arg residues on the polar face, even across the gut, and enters plasma, a decrease in plasma cholesterol levels was observed. As shown in FIG. 17, oral administration of R18L-2Y (mixed with chow and administered as described in the FIG. 17), showed significant decrease in cholesterol levels at 15 days and 30 days. Based on these results, the peptides 18L-2Y and R18L-2Y were mixed with normal chow (1 mg of the peptide for 4 g of chow) and fed to four week old female apo E null mice, ad libidum. The study was continued for 6 weeks. At the end of the study period, animals were euthanized and aortic sinus from each animal was analyzed for atherosclerotic plaque development using Oil Red O. As shown in FIG. 8, R18L-2Y treated group (and not the other two groups) had significantly less lesion formation compared to both control mice and 18L-2Y treated mice. As shown in FIG. 18, plasma cholesterol was also significantly reduced in R-18L-2Y group and not in other two groups.

Example 10

Described below are studies of two major pathways for inhibiting atherogenesis, decreasing plasma cholesterol levels and improving endothelial cell function due to changes in lipoproteins, especially the HDL function. This example centers on examples of the peptides described above, specifically, Ac-hE-18A-NH$_2$ (SEQ ID NO: 12), Ac-hE-4F-NH$_2$ (SEQ ID NO: 63), and R18L-2Y (SEQ ID NO: 62) as agents that are able to modulate dual properties in vivo, the rapid hepatic clearance of atherogenic lipoproteins and alteration of endothelial function. The overall design is described diagrammatically in FIG. 10. The schematic illustrates that upon cationic peptide interaction with plasma lipoproteins several changes occur. (1) Peptides interact with apo B-containing atherogenic lipoprotein particles to incorporate positively charged domains. This will then be recognized by the receptors on the hepatic cell surface to clear these atherogenic lipoproteins from circulation, thus inhibiting atherosclerosis. (2) Peptides modify HDL in the plasma to increase PON activity and decrease lipid hydoperoxides (LOOH) levels (Navab, M., et al. Circulation 109:3215-3220 2004); lower plasma LOOH levels lead to increased functional nitrous oxide (NO) levels and restoration of endothelial function in dyslipidemic animal models. Inhibition of monocyte chemotactic protein-1 (MCP-1) synthesis can then result in reduced monocyte chemotaxis and macrophage accumulation; thus resulting in inhibition of atherosclerosis.

Uptake of Apo B-containing Lipoproteins in Hep G2 Cells, Mouse and Rabbit Hepatocytes Results observed in HepG2 cells indicate that peptide associates with apo B-containing plasma lipoproteins to incorporate positive charges on the lipoprotein surface. This enables the apo B-containing lipoproteins to interact with heparan sulphate proteoglycans (HSPGs). The effect of these peptides on the mode of reduction of plasma cholesterol levels in mouse models and the two rabbit models can be determined. In NZW rabbits fed a 1% cholesterol-diet, a reduction of plasma cholesterol is observed which lasts for 14 days after the peptide administration; whereas in the WHHL rabbits, the reduction is initially rapid and returns to original levels within 3 days. Since the WHHL rabbit model is LDL-receptor defective, the differential effects of the peptide in two models can be due to differences in the receptor-mediated clearance pathways of atherogenic lipoproteins. HepG2 cells, primary hepatocytes from apo E null and LDL-R null mice, and primary rabbit hepatocytes can be used to determine the molecular factors in the receptor-mediated clearance pathways of atherogenic lipoproteins.

Isolated hepatocytes can be isolated from two mouse models with peptide:apo B-containing lipoprotein complexes (to determine possible effect of the peptides on cell surface lipoprotein receptors). Initially, human plasma lipoproteins can be used to determine the extent of internalization in hepatocytes from different animal models. These studies can determine the commonality and differences in hepatocytes and the ability of the peptides to modify lipoprotein surfaces. These modifications can be correlated to the uptake and degradation by different hepatocytes and in presence of peptides R18L-2Y, Ac-hE-18A-NH$_2$ and Ac-hE-4F-NH$_2$. The role of LDL-R and LRP receptors in the uptake and degradation of these complexes can also be determined. Whether the peptides enhance the uptake and degradation of apo B-containing lipoproteins via the HSPG-mediated pathway using heparinase/heparatinase can be determined as described by Datta et al. (Datta, G. et al. Biochemistry 39:213-220 2000) as well as if and by what mechanism(s) peptide-lipoprotein complexes are internalized. Using mutant CHO-cells that lack proteolysis (Esko, J. D. et al. Curr. Opin. Biol.: 3:805- 816 1991) the role of HSPG in the uptake and degradation can also be determined. The role of LRP can be studied using LRP-deficient fibroblasts. These procedures are described by Datta et al. using human plasma LDL and VLDL samples (Datta, G. et al. Biochemistry 39:213-220 2000; Datta, G. et al. J. Lipid Res. 42:959-966 2001). The effect of peptide administration on the receptor-associating ability of apo B-containing lipoproteins isolated from mice administered with the peptide (and blood sampled at earlier and later time points, within 30 min and 4 h, respectively, after peptide administration) will be studied and compared to apo B-containing lipoproteins from control mice. This requires a careful characterization of the lipoprotein properties to identify potential changes in receptor-ligand interactions as well as oxidation status. Controls for these experiments are normal cell lines that possess receptors.

In rabbits, apo A-I is synthesized in the intestine and not in the liver (Pan, T. C., et al. Eur. J. Biochem. 30:99-104 1987). Thus, these studies can determine if de novo synthesis of apo E and possible mechanisms of uptake of atherogenic apo B-containing lipoproteins. In rabbit hepatocyte studies, lipoproteins isolated from peptide-administered WHHL rabbits and NZW rabbits on high fat diet can be used for these studies. In WHHL rabbits, due to receptor defect, normal receptor-mediated atherogenic binding and uptake is compromised. Thus, any uptake of atherogenic lipoproteins is due to HSPG and/or LRP pathway. Treatment with peptides can reduce or even eliminate LOOH from the surface of lipoproteins. These lipoproteins can then be studied for receptor-mediated binding and uptake in HepG2 cells and in primary culture from rabbit hepatocytes. To determine if removal or reduction of LOOH alone can modify hepatic uptake of these atherogenic lipoproteins, a peptide that does not incorporate positive charges on the lipoprotein surface but yet is capable of reducing LOOH levels can be utilized. Such a peptide is 4F (SEQ ID NO: 17) or other class A peptides in this series (Navab, M., et al. Circulation 109:3215-3220 2004). This study will be able to distinguish between positively charged peptide incorporation enhancing the uptake of atherogenic lipoproteins versus removal or reduction of LOOH from lipoprotein surface. These studies can thus determine whether the class A part or the positively charged apo E part (for example, LRKLRKRLLR; SEQ ID NO: 1) or a combination of the two is responsible for the enhanced hepatic uptake. In the single domain peptide R18L-2Y, these studies can provide information on the make up of the nonpolar face for reducing plasma LOOH levels since 4F serves as a control peptide for determining the difference between cationic nature versus class A motif on their biological properties. Both 4F and R18L-2Y possess clustered π-electrons at the center of the nonpolar face. Observations of the peptides indicate that by covalently linking the two domains, a novel new peptide whose properties are not just the sum of the properties of two domains but a peptide with unique properties have been identified. Use of hepatocytes from apo E null and LDL-R null mice can also provide information on the role of LDL-receptor, HSPG and/or LRP pathway for enhanced atherogenic lipoprotein uptake. These two systems can provide information on how much of the effect is due to the direct effect of the peptide versus the enhanced synthesis of endogenous apo E, since apo E will not be synthesized in apo E null mouse hepatocytes. These investigations will complement established cell line studies. Use of rabbit hepatocytes will give information on the hepatic uptake of atherogenic particles in rabbits. As such, hepatocytes from WHHL rabbits and NZW rabbits can be used to understand the peptide-mediated uptake. It is possible that the single domain peptide R18L-2Y would inhibit atherosclerosis and decrease apo B-containing lipoproteins in an entirely different mechanism. Using $^{14}$C-radiolabeled peptide we will determine the ability of each peptide to recycle and possess chronic antiatherogenic properties either via the synthesis of preβ-HDL or increased synthesis of antiatherogenic proteins such as apo E, apo A-I and possible receptors, as shown in FIGS. 5, 7 and 9.

To determine if peptides alter the synthesis of antiatherogenic proteins, Hep G2 cells and hepatocytes obtained from these animal models can be incubated with peptides and levels of proteins and mRNA levels can be determined using suitable primers for these proteins. Results on these lines are provided in FIG. 9. Based on the differences seen in two mouse (apo E null and LDL-R null mouse models) and rabbit models, results on the induction of apo A-I synthesis in the preβ-DL form in HepG2 cells (FIG. 5) (Dashti, N. et al, J. Lipid Res. 45:1919-1928 2004), the synthesis of one or more of the following proteins (a) apo E, (b) LDL-R, (c) apo A-I, (d) chylomicron-remnant receptor, (e) LRP, (f) LPL, (g) VLDL-R can be studied. If peptides alter the properties of lipoproteins, there can be no changes in the levels of proteins or mRNA. These studies can separate the direct and indirect antiatherogenic effects of peptides. Use of hepatocytes from these models can also determine the possible differences in the mechanism of action of these peptides in these two animal models.

Hepatic clearance of atherogenic lipoproteins is considered antiatherogenic; however, macrophage uptake is atherogenic. Apo E has been shown to mediate hepatic uptake of atherogenic lipoproteins (Mahley, R. W. Science. 240:622-630 1988). Macrophages secrete LPL into the culture medium. Several factors, such as cytokines (interleukins) in the artery wall, can regulate macrophage LPL expression. Inhibition of macrophage LPL activity by apo E has been thought to inhibit uptake of lipoprotein remnants by macrophages but divert them to apo E-mediated hepatic uptake. Zilversmit and Witztum and co-workers have suggested that LPL present on the endothelial surface may produce remnant lipoproteins which may be potentially atherogenic (Zilversmit, D. E., Circulation 60:473-485 (1979); (Yla-Herttuala, S. et al. Proc. Natl. Acad. Sci. U.S.A. 88:10143-10147 1991). With this in mind, the role of peptide in vitro in modulating LPL activity can be determined. Previously, it has been demonstrated in vitro that class A peptides modulate LPL activity (Chung, B. H., et al. J. Lipid Res. 37:1099-1112 1996). One of the major preliminary findings in both the rabbit models is that the peptide(s)-mediates accelerated clearance of remnant lipoproteins, and VLDL. Plasma from peptide-administered rabbits shows no turbidity whereas plasma from rabbits not treated with the peptide shows turbidity. This result is corroborated by the results in FIGS. 11 and 12) hich demonstrate that VLDL-like particles are significantly reduced in NZW (on 1% cholesterol diet and peptide administered) and WHHL rabbits, which show a significant decrease in plasma TG levels (in WHHL). The total plasma cholesterol levels do not increase in the peptide-treated rabbits despite continued feeding of the high cholesterol diet. However, the plasma residence time for the peptide is relatively short ($t_{1/2}$=1 to 2 min) as shown in FIG. 9. It can be determined whether the peptide blocks accumulation of VLDL, TGRLP, modified-LDL (containing increased LOOH levels such as plasma from WHHL rabbits). The levels of mRNA and protein can also be determined in the same studies.

Whether the peptide analogs exert their effect by inhibiting uptake of apo B-containing lipoproteins by monocyte-macrophages and/or if they promote efflux of cholesterol from the cholesterol loaded macrophage can also be determined. Previously published results indicate that class A amphipathic helical peptides inhibit the ability of VLDL-induced foam cell formation in cultured THP-1 monocyte derived macrophages (Chung, B. H., et al. J. Lipid Res. 37:1099-1112 1996). The procedure for determining LPL activity modulation and effect on THP-1 monocyte-derived accumulation has been described in detail in Chung et al (Chung, B. H., et al. J. Lipid Res. 37:1099-1112 1996). and the described studies can be used to determine the effects of the present peptides. As such, VLDL isolated from these two rabbit models (with and without peptide administration) can be incubated with isolated LPL and determine the amount of free fatty acids obtained as an indication of differences in LPL activity. If peptides bind to HSPG (similar to what is proposed, for LPL) atherogenic lipoproteins can then bind and get internalized via LDL-receptor related protein as suggested previously (Besiegel, U. et al. Proc. Natl. Acad. Sci. U.S.A. 88:8342-8346 1991). These studies can be performed using both the single domain and dual-domain peptides.

Results also indicate apo B-48-enriched 31-VLDL appears in plasma of cholesterol-fed rabbits. The inhibition of atherosclerosis due to the peptides can be due to masking apo B domains involved in high affinity uptake of these lipoproteins by the TGRLP/apo B-48 receptor. A domain of apo B-48 has been shown to be sufficient for high affinity binding of TGRLP/apo B-48 receptor (Brown M. L., et al. Proc. Natl. Acad. Sci. USA 97:7488-7493 (2000). With this in mind, apo B-48 receptor transfected CHO cells incubated at 37° C. for 3 h with chylomicron Sf>400 with apo B48 as the only apo B48 species at 100 tjg TG/ml RPMI with and without the peptide in a concentration dependent manner (5 tjg to 100 jtg) and then stained with Oil Red O to detect cytoplasmic neutral lipid droplets can be performed. Vector only transfected cells can be incubated with chylomicrons under identical conditions and stained with Oil Red O.

Regarding whether the peptides reduce the atherogenic properties of LDL (i.e., effect on monocyte chemotaxis and enhance hepatic receptor binding properties in vitro) both in vitro and in vivo results indicate that the dual domain peptide changes HDL properties. Using the methods described by Dashti et al. (Dashti, N. et al, J. Lipid Res. 45:1919-1928 2004), it can be determined if there is increase in the synthesis of apo A-I and the possible mechanism. In previous studies peptide Ac-hE-18A-NH$_2$ resulted in increased PON activity in HDL, which destroys lipid hydroperoxides. Whether these changes alter levels of monocyte chemotactic protein and adhesion molecules such as VCAM-1 can also be determined (FIG. 6). Preliminary studies indicate that these peptides would possess much greater efficiency in reducing atherogenic properties of LDL.

Using lipoproteins isolated from the peptide-administered and control rabbits, the extent of LDL (or VLDL)-mediated monocyte chemotaxis can be determined using the endothelial cells-smooth muscle cells coculture system as described in (Navab, M., et al., J. Lipid Res. 41:1495-1508 2000; (Navab, M., et al., Circulation.105: 290-302 2002). Using cultured hepatocytes, whether the presence of peptides enhances the uptake of atherogenic lipoproteins from rabbits treated with peptides and control rabbits can also be determined.

Example 11

Changes in Apo A-I and Apo E-containing Particles and their Anti-inflammatory Properties Changes in apo A-I and apo E-containing particles and their anti-inflammatory properties can be determined by analyzing cell supernatants for the levels of different apolipoproteins by SDS gradient gels and scanning the bands for quantitation after Western blotting for different apolipoproteins. As described above, the changes in the lipoproteins secreted using different peptides can be determined. Production of pre-31 HDL is correlated to increased beneficial effects of HDL subpopulation in terms of clearance of lipid hydroperoxides from apo B-containing lipoprotein surfaces. These are related to inhibition of LDL-induced monocyte chemotaxis. Reduction in levels of oxidized LDL has been shown to inhibit cytokine and adhesion molecules production. As discussed above, whether the mRNA levels are correlated to increased levels of apolipoproteins can be determined. These studies can distinguish between the increase in the protein synthesis due to effect on mRNA levels vs being simply due to increased secretion and (as opposed to degradation) due to increased phospholipid levels as shown by us in published results (Dashti, N. et al, J. Lipid Res. 45:1919-1928 2004). The methods published by Dashti et al. (Dashti, N. et al, J. Lipid Res. 45:1919-1928 2004) can be used to determine the effect of different peptides on possible changes in the levels of apolipoproteins A-I and E, increased levels of which have been shown to be antiatherogenic. Cells labeled with $^{35}$S-Methionine to follow the new protein synthesis, can be used as described Dashti et al. (Dashti, N. et al, J. Lipid Res. 45:1919-1928 2004). $^3$H-glycerol can be used to determine changes in the lipid composition upon peptide incubation. HepG2 can be incubated in serum free MEM and incorporation of $^3$H-glycerol (5 μCi) into different pools of lipids in the presence and absence of peptides can be determined 5 h after incubation with peptides. Cells present in the medium and in cells can be extracted by the method of Folch et al. (Folch, J. et al., J. Biol. Chem. 226:497-509 1957). The final extracts can then be analyzed by TLC as previously described (Dashti, N. et al, J. Lipid Res. 45:1919-1928 2004).

Example 12

Effect of Peptides on Plasma Cholesterol Levels, Lesion Inhibition in Animal Models of Atherosclerosis, and Modulation of HDL Properties Two mouse models can be used to study the effect of different peptides on atherosclerosis, namely apo E null mice on chow diet and LDL-R null mice on Western diet. Apo E null mice develop atherosclerosis spontaneously on normal chow and the lesion begins to form in the aortic sinus at the age of 4 to 6 weeks. At 16 weeks of age, well defined lesions are formed at the aortic sinus. This mouse model can be used to initiate peptide administration at 4 weeks of age and administered for 6 weeks. Retroorbiral administration and administration by the tail vein revealed a decrease in plasma cholesterol. In mouse models of atherosclerosis (LDL-R null mice and apo E null mice) the peptides can be administered (50 μg/mouse) retroorbitally as described above and in FIG. 2. This method enables administration of the peptide multiple times and with minimal effect on the health of the animal. Peptides can be first administered intravenously to apo E null and LDL-R null mice (on Western diet) and the ability of these peptides to reduce plasma cholesterol levels can be compared. To determine the ability of these peptides on the fast phase of reduction of plasma cholesterol levels, plasma cholesterol levels can be measured at 2 min, 30 min, 1 h, 4 h, 8 h and overnight. Using the $^{14}$C- radiolabelled peptide the kinetics of disappearance of the peptide from the plasma compartment can be determined. The organ distribution of the different peptides can also be determined.

The effect on lesion inhibition can be determined by performing studies in apo E null mice on normal chow and LDL-R receptor null mice on Western diet using the procedures described previously 25 animals can be used in each-group. Since in LDL-R null mice the lesions develop only when they are fed a Western diet, the type of lesion produced can be different. Thus a careful analysis of lesion upon peptide(s) administration can provide possible differences in the mechanism by which these peptides inhibit atherosclerosis.

In addition lesion morphology can be selectively altered by dietary cholesterol in rabbits. Based on the literature and the results described above, NZW rabbits fed a 1% cholesterol diet can develop lesions consisting of macrophage-derived foam cells. Although early foam-cell lesions in the rabbits resemble human fatty streaks, these lesions are expected to be different from the latter, forming fibrous or atheromatous plaques that are found in advanced human lesions. However, long term exposure to low levels of cholesterol in the diet has been shown to increase the variability including advanced, fibrous plaque which is compensated by increase in the number of animals. To determine the molecular events by which the peptide reduces atherosclerosis, the difference in the macrophage content of the lesions from the control and peptide-administered rabbits using two doses of the peptide can be determined. If the peptide acts directly, on the lesion formation, these two doses yield different numbers of macrophage foam cells. If the peptide acts indirectly in reducing atherosclerosis, two doses can provide similar macrophage-foam cell numbers/lesion area. Histological analysis includes stains for lipids, macrophages (using antimacrophage monoclonal antibody Ram-1 1), and smooth muscle cells(monoclonal antibody HHF-3, directed against smooth muscle cell-specific actin to determine SMC-rich fibrous cap formation; differences in smooth muscle migration can result with peptide administration that is related to correcting endothelial cell dysfunction.

It can also be determined whether the peptide inhibits atherosclerotic lesion formation by decreasing plasma cholesterol and atherogenic lipoprotein levels during the high fat diet regime compared to control rabbits (not given the peptide). For these studies, NZW rabbits that respond to diet can be selected. All animals are fed a 1% cholesterol diet and their cholesterol values determined three days after the diet initiation. Twenty rabbits with similar cholesterol levels can be selected and changed back to a normal diet. After 15 days on a normal diet, cholesterol values can once again be determined to check if the values returned to normal. Animals whose cholesterol values have not returned to pre-diet levels can be monitored until they are normalized or removed from the study. Ten rabbits in each group are selected and simultaneous peptide administration and 1% diet initiation can follow. In the preliminary studies the daily average food intake and body weight were not significantly different between control and peptide administered group even after 6 weeks of 1% cholesterol diet and one month after (3 mg/kg) peptide administration (Control group food intake was 0.16±0.02 kg, average body weight was 4.45±0.27 kg and in peptide administered group, average food intake was 0.17±0.03 kg and average body weight was 4.8±0.4 kg). To study dose-response effects, smaller number of animals (five in each group can be administered three doses of peptide (5 mg/kg, 3 mg/kg and 1.5 mg/kg). After the initial experiments, the dose of the peptide can be decided. A solution of the peptide (sterile saline) can be injected through the ear vein, once a week for the duration of the study (based on previous experience, for 6 weeks). The study parameters include total cholesterol, lipoprotein levels, LOOH levels, PON activity in the plasma. At the end of six weeks, the rabbits are euthanized and histology assessed.

Example 13

Modulation of HDL Properties

Oxidation of LDL is associated with changes in both vascular structure and function. Activation of endothelial cells leads to an increased expression of adhesion molecules and chemokines such as VCAM-1, MCP-1 which also enhance the accumulation of cholesterol. Under these conditions, there is enhanced formation of reactive oxygen species (ROS), resulting in reduced levels of endothelial NO (White, C. R., et al., Proc. Natl. Acad. Sci. USA. 91:1044-1048 1994; White, C. R., et al., Proc. Natl. Acad. Sci. (USA) 93: 8745-8749 1996). It has been shown that in WHHL rabbits Ac-hE-18A-NH$_2$ not only decreases atherogenic lipoprotein levels, but also remodels the existing HDL to form an apo A-I containing and peptide-containing particle that has increased PON activity. This particle is also able to recruit lipid hydroperoxides which get cleared due to increased PON activity. Inhibition of LDL oxidation inhibits monocyte chemotaxis, thus, prevents its accumulation in the vessel wall and lesion formation (White, C. R., et al., Proc. Natl. Acad. Sci. (USA) 93: 8745-8749 1996). Several publications related to class A peptides studies have demonstrated remodeling of HDL in mouse and monkey models.

Figure 19:
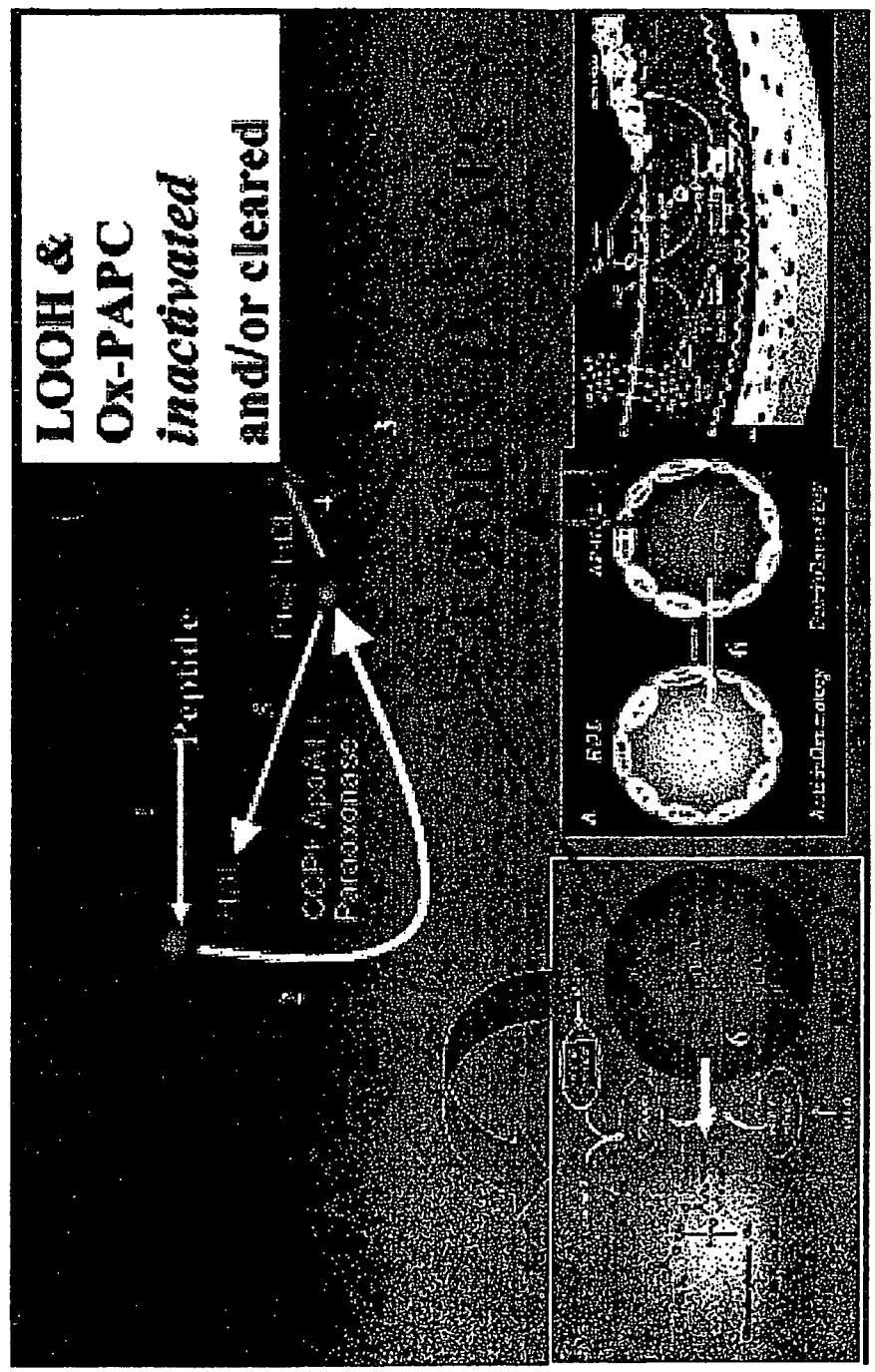
FIG. 19 shows peptide-Ac-hE-18A-NH$_2$-mediated improvement of HDL function.

A reduction in plasma HDL is associated with impairment of reverse cholesterol transport (RCT). This results in accumulation of cell-derived cholesterol within the arterial wall, which manifests into advanced carotid intima-media thickening and marked susceptibility to atherosclerosis (Clee, S. M., et al. J. Clin. Invest. 106:1263-1270 2000). Increasing HDL in subjects with low HDL facilitates the removal/clearance of atherogenic lipoproteins and improves endothelial function (Bisoendial, R. J., et al., Circulation 107:2944-2948 2003; Calabresi, L., et al., Athero. Thromb. Vasc. Biol. 23:1724-1 731 2003; Kaul, S., et al., J. Am. Coll. Cardiol. 44:1311-1319 2004). It is believed that peptides improve HDL function by recruiting apo A-I and PON (FIG. 19) and protects endothelial function by facilitating the removal of atherogenic lipoproteins from the vessel wall. Removal of LOOH increases PON activity and not PON mRNA levels or PON protein levels. The mechanism(s) by which this restoration takes place can be determined by studying the effect of the peptide on RCT using procedures described by Navab et al. (Navab, M., et al. Circulation 109:3215-3220 (2004); Rader, D. J. Am. J. Cardiology. 92:42J-49J (2003)). In rabbit models, the amount of cholesterol excreted as bile salts and cholesterol esters can be studied using methods described by Navab et al. (Navab, M., et al., Circulation. 110: 120-125 2004). The effect of peptide(s) on ABCA1-mediated cholesterol efflux in J774 macrophages can also be studied. Macrophage ABCA1 expression can be determined by RT-PCR and Western Blot. Macrophages are seeded in 12 well plates at a density of 2×10$^6$ cells/well in DMEM containing 10% FBS and allowed to attach overnight. 24 h after plating cells are labeled with $^3$H-cholesterol (10 µCi) according to the method of Sparrow et al. After an additional 24 h, cells can be washed and media replaced with serum-free media containing 0.1% BSA. Studies can be performed in the presence or absence of a bromo-derivative of cAMP to determine the ABCA1-mediated cholesterol efflux and cholesterol efflux due to microsolubilization. Cholesterol efflux can be stimulated by the addition of peptide or purified A-I for an additional 24 h period. Media can then be recovered and cells solubilized in PBS containing 0.5% Triton X-100. Radioactivity in aliquots of media and solubilized cells can then be measured. Cholesterol efflux can be analyzed by measuring radioactive counts in the media as a percentage of total counts. It has been shown that chlorination or nitration of Tyr in apo A-I produces dysfunctional apo A-I (Constanze, et al., Natl. Acad. Sci. U.S.A. 101:13032-13037, 2004). Radioactive tracer peptide can be used in some situations. If iodination of peptide alters properties of the peptide, $^{14}$C-labelled peptide can be used by acetylating the peptide using $^{14}$C-acetic acid.

Measurement of paraoxanase (PON) can also be performed. The antioxidant capacity of HDL is attributed primarily to the presence of the enzyme PON. HDL isolated from mice that overexpress the gene for PON-1 is highly resistant to LOOH formation induced by copper (Valabhji, J., et al., Clinical Science. 101:659-670 2001). A decrease in PON activity is associated with dyslipidemia and insulin resistance in leptin- and LDL receptor-deficient mice and diabetic humans (Valabhji, J., et al., Clinical Science. 101:659-670 2001; Griendling, K. K. et al., Circulation Research. 86:494-501 2000; Mertens, A., et al., Circulation. 107:1640-1646 2003; Sanguinetti, S. M., et al., Diabetes, Nutrition & Metabolism-Clinical & Experimental. 14:27-36 2001; Quyyumi, A. A. Am. J. Med. 105:32S-39S 1998; Halcox, J. P., et al., Circulation. 106:653-658, 2002). With this in mind, it can be determined whether chronic Ac-hE-18A-NH$_2$, Ac-hE-4F-NH$_2$, and R18L-2Y administration increases PON activity in plasma and isolated lipoprotein fractions of the two rabbit models. PON activity can be determined using paraoxon (O, O-diethyl-O-p-nitrophenylphosphate; Sigma Chemical Co.) as substrate.

Whether peptide administration improves endothelial function can also be determined. Endothelial function is compromised under conditions of inflammation and atherogenesis (Quyyumi, A. A. Am. J. Med. 105:32S-39S 1998; Halcox, J. P., et al., Circulation. 106:653-658, 2002). Defects in lipoprotein metabolism and vascular reactivity are fundamental pathological responses to hypercholesterolemia. Extensive evidence suggests that ROS play an important role in the initiation and progression of these lesions (Griendling, K. K. et al., Circulation Research. 86:494-501 2000). Blood vessels from atherosclerotic patients and hypercholesterolemic animal models exhibit impaired, endothelium-dependent relaxation (Quyyumi, A. A. Am. J. Med. 105:32S-39S 1998; Halcox, J. P., et al., Circulation. 106:653-658, 2002). NO is modified in a hyperlipidemic environment via its reaction with superoxide anion ($O_2$), resulting in reduced NO bioactivity and yielding the potent oxidant peroxynitrite (ONOO) (White, C. R., et al., Proc. Natl. Acad. Sci. USA. 91:1044-1048 1994). ONOO may promote atherogenesis by reducing the beneficial physiological actions of NO and oxidizing lipoproteins (White, C. R., et al., Proc. Natl. Acad. Sci. USA. 91:1044-1048 1994). Improvement in HDL function can result in a decrease in the atherogenicity of LDL which can direct LDL to a normal uptake (as apposed to scavenger receptor uptake) and thus plasma cholesterol lowering. These changes are expected to increase endothelial-derived NO bioactivity.

The effect of the peptides on anti-inflammatory properties can also be determined. Endothelial dysfunction is an early feature of atherosclerotic disease (Quyyumi, A. A. Am. J. Med. 105:32S-39S 1998). It is an important independent clinical prognostic indicator in patients with or without coronary artery disease. Furthermore, improvement in endothelial function is associated with improved clinical outcomes. Endothelium plays an important role in vessel homeostasis by participating in divergent pathophysiologic processes including vessel tone maintenance, thrombosis and inflammatory pathways associated with atherosclerosis (Halcox, J. P., et al., Circulation. 106:653-658, 2002). Endothelial dysfunction is associated with numerous factors including dyslipidemia, hypertension, smoking and possibly genetic and environmental influences. Of the various pharmaceutical interventions, use of angiotensin inhibitors and statins are associated with improvement in endothelial function. The beneficial action of statins has been linked to lowering of total plasma cholesterol and LDL. Still, there is significant mortality and morbidity associated with atherosclerotic disease. One of the widely recognized theories of atherosclerosis is the "response to injury" hypothesis in which oxidized LDL causes endothelial dysfunction, leading to an insult to smooth muscle cells and in cell proliferation. Key features of atherosclerosis are therefore the recruitment of blood monocytes to and through endothelium, the activatidn/differentiation of these monocytes to macrophages and the uptake of lipid and lipoproteins by the macrophages to form foam cells. As such, it can be determined whether the peptide modified HDL structure and function, leading to an improvement in endothelial function (FIG. 15). Cholesterol lowering per se can significantly increase NO bioavailability in isolated arteries of hypercholesterolemic rabbits. It can also be tested whether the peptides modulate the binding and/or expression of pro-oxidant enzymes in vascular cells.

Whether peptide administration reduces superoxide production in blood vessels of hypercholesterolemic rabbits can also be determined. Nitric oxide becomes modified in a hyperlipidemic environment via its interaction with superoxide anion radical (O2), resulting in diminished physiological activity (White, C. R., et al., Proc. Natl. Acad. Sci. USA. 91:1044-1048 1994). Superoxide is generated in both intracellular and extracellular compartments in response to activation of pro-oxidant enzymes (NADPH oxidase, xanthine oxidase, etc) and reacts with the more membrane-permeable and diffusible NO, yielding the potent oxidant peroxynitrite (ONOO) (White, C. R., et al., Proc. Natl. Acad. Sci. (USA) 93: 8745-8749 1996; Griendling, K. K. et al., Circulation Research. 86:494-501 2000). As a corollary to the studies described above, $O_2$ production can be determined using coelenterazine-dependent chemiluminescence. The $O_2$-dependent oxidation of coelenterazine results in the formation of a high energy intermediate which emits light as it relaxes to the ground state. A rabbit aortic segment (approximately 3 mm wide) can be placed in a vial containing 2 ml 10 μM coelenterazine-PBS. Baseline $O_2$ production can be monitored in tissues from peptide- or saline-treated control animals every 30 sec for 30 min using a luminometer (BMG Labtechnologies Inc). Background chemiluminescence can be monitored in solutions of coelenterazine-PBS in the absence of vascular tissue. In control experiments, the specificity of the chemiluminescence signal for $O_2$ production can be verified by the addition of 100 U/mL PEG-SOD and the SOD mimetic tetrakis (N-ethylpyridinium-2-yl) porphyrin (T2E). These compounds localize to the extracellular surface and the' intracellular space respectively and effectively scavenge $O_2$. The assay is calibrated by monitoring the chemiluminescence signal of known amounts of $O_2$ generated by xanthine oxidase (0.05 U) and xanthine (10 to 50 μmol/L). Rates of $O_2$ production associated with these xanthine/xanthine oxidase incubation conditions can be determined spectrophotometically by measuring the $O_2$-dependent reduction of ferricytochrome C and can be normalized to tissue protein.

Studies can also be performed to determine whether peptide administration improves vascular NO release in isolated arteries of cholesterol-fed NZW and WHHL rabbits. NO release in response to chronic treatment with peptide or saline can be assessed by monitoring the formation of the metabolites nitrate ($NO_3$) and nitrite ($NO_2$). Aortic ring segments can be prepared as described above and placed in 0.5 ml PBS containing 1 μM A23187, a calcium ionophore which stimulates cellular NO formation via the calcium-dependent activation of NOS III. At the end of the 2 hr incubation period, 50 μl samples of PBS can be collected. Nitrate in this sample can be enzymatically reduced to $NO_2$ by treatment with *E. coli* enriched nitrate reductase. Total $NO_2$ can be used as an index of NO production (Zhang, C., et al. J. Biol. Chem. 276: 27159-27165 2001). Nitrite can be detected in the nM range using the fluorophore 2,3-diaminonaphthalene (DAN) (Calbiochem, Inc.). Under alkaline conditions, DAN converts NO2 to the fluorescent compound 1(H)-naphthotriazole. Nitrite concentration can then be monitored by the spectrofluorometric excitation of 1(H)-naphthotriazole (360 nm and emission at 450 nm). A standard curve can be constructed for $NaNO_2$ (1-1,000 nM) in order to convertfluorescence intensity values to concentrations. Nitrite formation will be normalized to protein concentration. In additional experiments, plasma levels of NO metabolites isolated from peptide- and saline-treated experimental animals can be measure.

Further experiments can be performed to determine whether the administration of the peptides influences the expression/activity of pro-oxidant enzymes in arteries of cholesterol-fed NZW and WHHL rabbits. Previous studies showed that an increase in plasma cholesterol in cholesterol-fed NZW rabbits was associated with the release of the pro-oxidant enzyme xanthine oxidase (XO) into the circulation and its concentration at HSPG binding sites on the vascular endothelium (White, C. R., et al., Proc. Natl. Acad. Sci. (USA) 93: 8745-8749 1996; Adachi, T., et al., Biochemical J. 289(2):523-527 1993). At this site, XO served as a source of O2 and contributed to the development of endothelial dysfunction. The inhibition of relaxation associated with XO binding could be reversed by addition of heparin, allopurinol, and chimeric heparin-binding superoxide dismutase. The identification of XO in vascular lesions of humans suggests that the enzyme can be a clinically relevant target for the therapeutic treatment of atherosclerosis (Swain, J. et al. FEBS Lett. 368(3):513-515 1995). This is underscored by findings that infusion of the XO inhibitor oxypurinol in humans increases forearm blood flow in HC, but not hypertensive, patients (Cardillo, C., et al., Hypertension 30:57-63 1997).

It has been reported previously that chronic elevation of plasma cholesterol in rabbits induces an increase in circulating xanthine oxidase concentration. The liver and intestine are principal sources of circulating XO. Cholesterol accumulation in the liver is associated with hepatocellular injury and increased conversion of xanthine dehydrogenase (XDH) to xanthine oxidase (XO). Increased plasma levels of alanine transaminase (ALT) are additionally associated with XO release in the circulation. Circulating XO readily binds to endothelial cell surface heparan sulfate proteoglycans (HSPG) and becomes endocytosed, thus inducing oxidative injury in both extracellular and intracellular compartments at distal sites. The administration of the peptide(s) can exert vascular protective effects via two mechanisms. First, as shown above, peptide-administration effectively reduces total plasma cholesterol which is predicted to reduce cholesterol-induced hepatic injury in hypercholesterolemic rabbits and circulating plasma XO activity. In addition, the peptides, due to their ability to interact with HSPG, can compete with and displace XO from the same cell surface binding sites. This action can reduce XO-mediated oxidant injury to the endothelium and underlying VSMCs. Under these conditions, circulating XO activity can be increased, but the chronic peptide(s) treatment can prevent XO binding to endothelial cells and reduces the formation of ROS at this site. Xanthine oxidase activity of plasma and tissues from control and hypercholesterolemic rabbits can be measured using HPLC (White, C. R., et al., Proc. Natl. Acad. Sci. (USA) 93: 8745-8749 1996). At sacrifice, plasma samples are obtained from test animals and immediately frozen at −80° C. Prior to measuring enzymatic activity, endogenous urate can then be removed by passing the sample over a Sephadex G-25 column. Samples can then be treated with oxonic acid (2 mM) to inhibit plasma unease activity. Xanthine (75 μM) can be added, and XO activity assessed by monitoring the production of urate. These reactions are performed in the absence and presence of $NAD^+$ (0.5 mM) and pyruvic acid (5 mM) in order to assess XO and total oxidoreductase (XO+XDH) activity, respectively. The specificity of this detection method for urate production by XO/XDH can be verified by inhibition of urate formation following allopurinol addition in some samples. XO protein content of homogenized arteries can be assessed by Western blot using a commercially available monoclonal anti-XO antibody (United States Biologicals). Effects of peptides treatment on XO binding/localization to the vascular wall can also be tested by immunohistochemistry using a commercially available XO antibody.

Alternatively, peptides can target the expression of NADPH oxidase, an additional source of vascular superoxide in arteries of hypercholesterolemic animals. Accordingly, real time polymerase chain reaction (RT-PCR) can be used to quantitate mRNA for $p22^{phox}$a critical subunit of the NADPH oxidase, in aortic tissues of cholesterol-fed NZW and WHHL rabbits. Total RNA can be extracted from aortas using TRIzol Reagent, and $p22^{phox}$mRNA analyzed by RT-PCR. $p22^{phox}$mRNA can be co-amplified with GAPDH mRNA in a Techne Thermal Cycler PHC-3. PCR products can be analyzed on a 1.2% agarose-ethidium bromide gel. The gels can then be photographed, and the intensity of the individual $p22^{phox}$ and GAPDH mRNA bands measured by laser densitometric scanning, using a Molecular Dynamics Personal Densitometer. Changes in $p22^{phox}$mRNA levels are expressed as a relative ratio of mRNA band intensity to that of GAPDH.

The effects of peptide administration on functional responses of arteries in two rabbit models can also be performed. Cholesterol-feeding of rabbits has been widely used to study the effects of hypercholesterolemia on vascular function and lipid oxidation (White, C. R., et al., Proc. Natl. Acad. Sci. USA. 91:1044-1048, 1994; Geetanjali, B., et al., Cardiovascular Pathology 11: 97-103 2002). Previous studies have shown a significant increase in plasma cholesterol levels in hypercholesterolemic NZW rabbits that are characterized by an increase in βVLDL content. The WHHL rabbit is also commonly used to study mechanisms of atherogenesis. WHHL rabbits are also hyperlipidemic, and, in contrast to cholesterol-fed NZW rabbits, exhibit increased plasma levels of LDL cholesterol. Experiments can be performed to assess the effects of peptide administration on endothelium- dependent relaxant responses in arteries of cholesterol-fed NZW and WHHL rabbits.

For these experiments, many animals described above can be used. New Zealand white rabbits (2.5-3.0 kg) (Myrtle Farms, Inc.) can be fed modified laboratory chow (Purina, Inc.) containing 1% cholesterol for 6 weeks. WHHL rabbits (Covance Inc.) plasma cholesterol levels are approximately 80 mg/dl and increase to 600±200 mg/dl by 6 months. Rabbits from each group are assigned at random to receive either peptides or saline (administered by i.v. infusion via the marginal ear artery) at 3 mg/kg/week for 7 to 8 weeks. After the treatment period, rabbits are euthanized, and the aorta can be excised and cleansed of fat and adhering tissue. Isometric tension can be measured as described previously (White, C. R., et al., Proc. Natl. Acad. Sci. USA. 91:1044-1048 1994; White, C. R., et al., Proc. Natl. Acad. Sci. (USA) 93: 8745-8749 1996). The vessel can then be cut into individual ring segments (3-4 mm in width) and suspended from a force-displacement transducer in a tissue bath. Ring segments can be bathed in a bicarbonate-buffered, Krebs-Henseleit (K-H) solution of the following composition (mM): NaCl 118; KCl 4.6; NaHCO$_3$ 27.2; KH$_2$PO$_4$ 1.2; MgSO$_4$ 1.2; CaCl$_2$1.75; Na$_2$EDTA 0.03, and glucose 11.1. A passive load of 3 g can be applied to all ring segments and maintained at this level throughout the experiment. At the beginning of each experiment, indomethacin-treated ring segments can be depolarized with KCl (70 mM) to determine the maximal contractile capacity of the vessel. Indomethacin is added under these conditions to inhibit the formation of cyclooxygenase-derived vasoactive metabolites. Rings can then be thoroughly washed and allowed to equilibrate. In subsequent experiments, vessels can be submaximally contracted (40% of KCl response) with PE ($3 \times 10^8 10^7$M). When tension development reaches a plateau, acetylcholine (Ach: $10^9$ to $3 \times 10^6$M) can be added cumulatively to the bath to invoke endothelium-dependent relaxation. At the end of each dose response protocol, sodium nitroprusside (SNP: 5 µM) can be added to elicit residual endothelium-independent relaxation. Real time data can be collected for all experiments and downloaded to an IBM PC for analysis using commercially available software. Preliminary data indicates that peptide-treated animals show restored endothelial function. These studies establish if this is so in both diet-induced and genetic models of atherosclerosis.

Morphometric analysis of aortic tissues can be subsequently performed to determine the effect of peptide treatment on fatty streak lesion formation. Lesion areas can be assessed using light microscopy and oil-red-O staining (Navab, M., et al., J. Lipid Res. 41:1495-1508 2000; Garber, D. W. et al., J. Lipid Res. 42:545-552 2001). Cholesterol content of the artery wall can also be performed using techniques described by Thorngate et al (Throngate, F. E. et al., Arterio. Thromb. Vasc. Biol. 20:1939-1945 2000).

Example 14

The effects of some of the disclosed apolipoprotein E-mimicking peptides on plasma cholesterol were investigated. ZDFfa/fa (Zucker diabetic fatty rats with a defect in their leptin receptor) male rats (5-6 weeks, 180-220 g) were obtained from Charles River Laboratories Inc. The rats were housed in individual cages and allowed to acclimatize for a few days prior to performing any intervention. The rats' diet consisted of a 2016 Tekiad Global 16% Protein Rodent Diet. Close monitoring of the dietary intake was performed. Water was provided ad-libitum.

Figure 20:
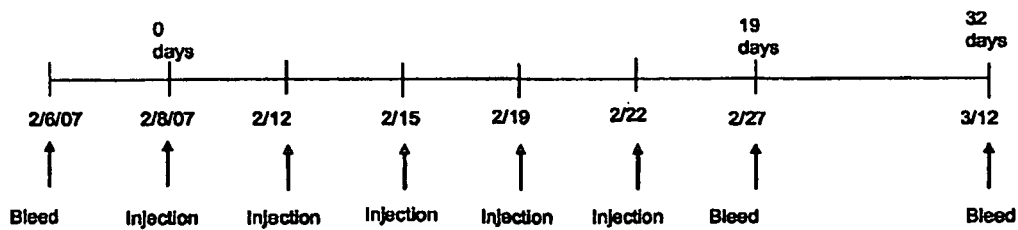
FIG. 20 shows the timeline of hE-4F, hE-Sc2F and L-4F administration to ZDF rats. Peptides were administered to the rats intravenously at a concentration of 5 mg/kg.

Rats were then divided into various groups (n=7-8/group): control (saline) and peptide. Animals were fasted overnight (12 h) prior to blood draws. Animals were individually administered one of the peptides (5 mg/Kg) or saline via the tail vein. (See FIG. 20 for a diagram of the timeline of administration). Any weight changes were monitored closely. Blood was obtained at baseline, and at pre-specified intervals. Plasma was separated and aliquoted.

Analysis on the blood extracted consisted of a cholesterol and an endocrine assay. The cholesterol assay was carried out using a colorimetric cholesterol assay. The assay was performed using a Cholesterol reagent (ThermoDMA, Arlington, Tex.). The endocrine assay was performed by Millipore, Inc using a Lincoplex multi-analyte rat endocrine kit. Rat adipnectin was measured by Millipore, Inc using mouse adiponectin RIA methodology.

Results

Figure 22:
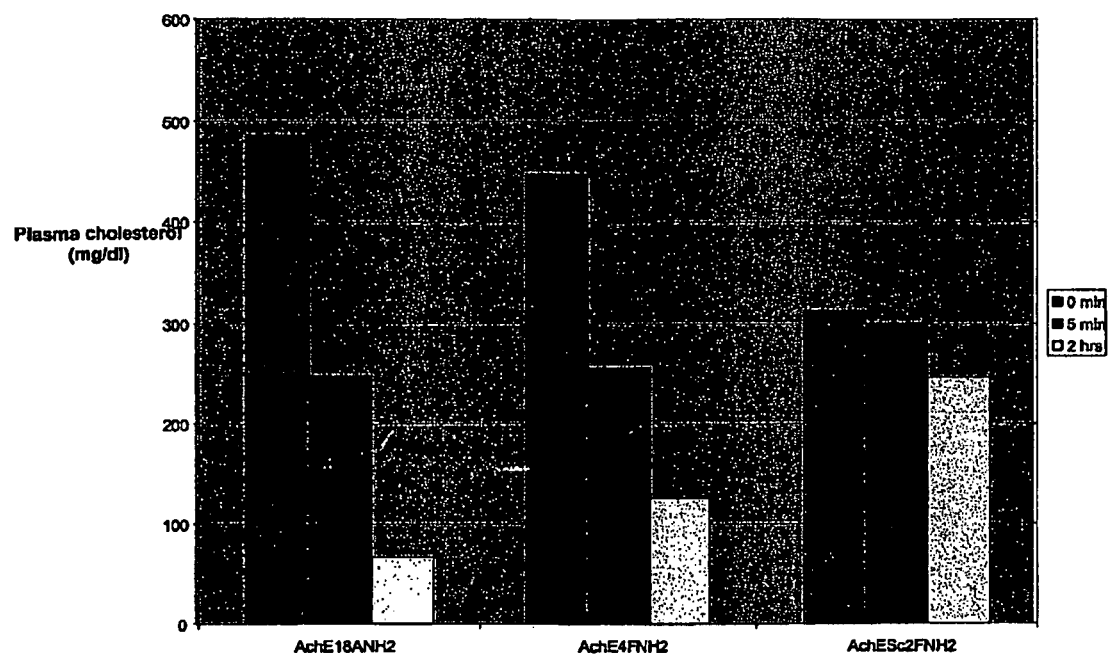
FIG. 22 shows the effect of three peptides on plasma cholesterol in apo E null mice at two different time points (5 minutes and 2 hours). The peptides represented are Ac-hE-18A-NH$_2$, Ac-hE4F-NH$_2$, and Ac-hE-Sc2F-NH$_2$. Peptides Ac-hE-18A-NH$_2$, Ac-hE-4F-NH$_2$ and Ac-hE-Sc18A were administered (i.v.) to apo E null mice (n=4) and plasma cholesterol values were determined at before administration (0 min), 5 min and 2 h after administration. While Ac-hE-18A-NH$_2$ and Ac-hE-4F-NH$_2$ show a higher reduction in plasma cholesterol levels at 2 h time point, peptide Ac-hE-Sc18A-NH$_2$ did not show much difference.

As described above, peptides Ac-hE-18A-NH$_2$, Ac-hE-4F-NH$_2$ and Ac-hE-Sc18A were administered (iv) to apo E null mice (n=4) and plasma cholesterol values were determined at before administration (0 min), 5 min and 2 h after administration. Results are shown in FIG. 22. While Ac-hE-18A-NH$_2$ and Ac-hE-4F-NH$_2$ showed a large reduction in plasma cholesterol levels at 2 h time point, peptide Ac-hE-Sc18A-NH$_2$ did not show such as great of a difference, however, plasma cholesterol levels were decreased.

What is claimed is:

1. A synthetic apolipoprotein E-mimicking peptide, consisting of: a receptor binding domain of apolipoprotein E comprising the amino acid sequence of SEQ ID NO: 15; and a lipid-associating peptide wherein said receptor binding domain is covalently linked to said lipid-associating peptide, wherein the lipid-associating peptide comprises a class A amphipathic-helical domain.

2. The synthetic apolipoprotein E-mimicking peptide of claim 1, wherein said lipid-associating peptide is SEQ ID NO: 4.

3. The synthetic apolipoprotein E-mimicking peptide of claim 1, wherein said lipid-associating peptide comprises the amino acid sequence of SEQ ID NO: 16.

4. The synthetic apolipoprotein E-mimicking peptide of claim 1, wherein said lipid-associating peptide comprises the amino acid sequence of SEQ ID NO: 17.

5. The synthetic apolipoprotein E-mimicking peptide of claim 1, wherein said synthetic peptide is protected using acetyl and amide groups at the N- and C-terminus, respectively.

6. A pharmaceutical composition, comprising the synthetic apolipoprotein E-mimicking peptide of claim 1 and a pharmaceutically acceptable carrier.

7. An isolated nucleic acid encoding the polypeptide of claim 1.

8. A vector comprising the nucleic acid of claim 7.

9. A host cell comprising the nucleic acid of claim 7.

10. An isolated nucleic acid encoding the polypeptide of claim 4.

11. A vector comprising the nucleic acid of claim 10.

12. A host cell comprising the nucleic acid of claim 10.

* * * * *

UNITED STATES PATENT AND TRADEMARK OFFICE
CERTIFICATE OF CORRECTION

PATENT NO.        : 8,557,767 B2           Page 1 of 1
APPLICATION NO.   : 12/675073
DATED             : October 15, 2013
INVENTOR(S)       : Anantharamaiah et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 578 days.

Signed and Sealed this

Fifteenth Day of September, 2015

Michelle K. Lee
*Director of the United States Patent and Trademark Office*